(12) United States Patent
Muller et al.

(10) Patent No.: US 9,452,182 B2
(45) Date of Patent: Sep. 27, 2016

(54) COLLATERAL GENE INACTIVATION BIOMARKERS AND TARGETS FOR CANCER THERAPY

(71) Applicants: Board of Regents, The University of Texas System, Austin, TX (US); Dana-Farber Cancer Institute, Inc., Boston, MA (US)

(72) Inventors: Florian L. Muller, Houston, TX (US); Eliot Fletcher-Sananikone, Houston, TX (US); Simona Colla, Houston, TX (US); Elisa Aquilanti, Boston, MA (US); Ronald DePinho, Houston, TX (US)

(73) Assignees: Board of Regents, The University of Texas System, Austin, TX (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/365,367

(22) PCT Filed: Dec. 14, 2012

(86) PCT No.: PCT/US2012/069767
§ 371 (c)(1),
(2) Date: Jun. 13, 2014

(87) PCT Pub. No.: WO2013/090732
PCT Pub. Date: Jun. 20, 2013

(65) Prior Publication Data
US 2014/0378529 A1 Dec. 25, 2014

Related U.S. Application Data

(60) Provisional application No. 61/570,366, filed on Dec. 14, 2011, provisional application No. 61/652,738, filed on May 29, 2012.

(51) Int. Cl.
| | | |
|---|---|---|
| *A61K 48/00* | (2006.01) |
| *C07H 21/02* | (2006.01) |
| *C07H 21/04* | (2006.01) |
| *A61K 31/713* | (2006.01) |
| *A61K 45/06* | (2006.01) |
| *A61K 31/191* | (2006.01) |
| *A61K 31/5685* | (2006.01) |
| *A61K 31/662* | (2006.01) |
| *A61K 31/198* | (2006.01) |
| *A61K 31/35* | (2006.01) |
| *A61K 31/352* | (2006.01) |
| *A61K 31/357* | (2006.01) |
| *G01N 33/50* | (2006.01) |
| *G01N 33/574* | (2006.01) |
| *C12Q 1/68* | (2006.01) |
| *A61K 31/661* | (2006.01) |
| *C12N 15/113* | (2010.01) |

(52) U.S. Cl.
CPC ........... *A61K 31/713* (2013.01); *A61K 31/191* (2013.01); *A61K 31/198* (2013.01); *A61K 31/35* (2013.01); *A61K 31/352* (2013.01); *A61K 31/357* (2013.01); *A61K 31/5685* (2013.01); *A61K 31/661* (2013.01); *A61K 31/662* (2013.01); *A61K 45/06* (2013.01); *C12N 15/1137* (2013.01); *C12Q 1/6886* (2013.01); *G01N 33/5038* (2013.01); *G01N 33/5743* (2013.01); *G01N 33/57407* (2013.01); *A61K 48/00* (2013.01); *C12N 2310/14* (2013.01); *C12N 2310/531* (2013.01); *C12N 2320/31* (2013.01); *C12Q 2600/106* (2013.01); *C12Q 2600/156* (2013.01); *C12Y 402/01001* (2013.01); *C12Y 402/01011* (2013.01); *G01N 2333/988* (2013.01); *G01N 2800/52* (2013.01)

(58) Field of Classification Search
CPC ............................. A61K 48/00; C12N 15/111
See application file for complete search history.

(56) References Cited

U.S. PATENT DOCUMENTS

| 6,046,002 A | 4/2000 | Davis et al. |
| 6,200,754 B1 | 3/2001 | Housman et al. |
| 2009/0137473 A1 | 5/2009 | Martin et al. |
| 2009/0175844 A1 | 7/2009 | Nakamura et al. |
| 2009/0324682 A1 | 12/2009 | Popowski |
| 2010/0189648 A1 | 7/2010 | Huang et al. |

FOREIGN PATENT DOCUMENTS

| WO | WO 98-41648 | 9/1998 |
| WO | WO 03-082187 | 10/2003 |
| WO | WO 2007/072219 | 6/2007 |

(Continued)

OTHER PUBLICATIONS

Anderson et al., "Reaction intermediate analogues for enolase," *Biochemistry*, 23:2779-2786, 1984.

(Continued)

*Primary Examiner* — Amy Bowman
(74) *Attorney, Agent, or Firm* — Parker Highlander PLLC

(57) ABSTRACT

Methods for treating a subject determined to have a cancer comprising a heterozygous inactivation of a housekeeping gene (or a homozygous deletion of a functionally redundant housekeeping gene) by treating the subject with an inhibitor of the gene. For example, a subject having a cancer with an ENO gene deletion can be treated with a glycolysis inhibitor, such as an enolase inhibitor. In some aspects, a subject having a cancer with an ARS gene deletion can be treated with an ARS inhibitor.

20 Claims, 48 Drawing Sheets

(56) References Cited

FOREIGN PATENT DOCUMENTS

| WO | WO 2008-102557 | 8/2008 |
|---|---|---|
| WO | WO 2009-002607 | 12/2008 |

OTHER PUBLICATIONS

Bagchi and Mills, "The quest for the 1p36 tumor suppressor," *Cancer Res.*, 68:2551-2556, 2008.

Basilion et al., "Selective killing of cancer cells based on loss of heterozygosity and normal variation in the human genome: a new paradigm for anticancer drug therapy," *Molecular Pharmacology*, 56:359-369, 1999.

Brookfield, "Genetic redundancy," *Adv Genet*, 36:137-155, 1997.

Costanzo et al., "The genetic landscape of a cell," *Science*, 327:425-431, 2010.

de A. S. Navarro et al., "Structural flexibility in Trypanosoma brucei enolase revealed by X-ray crystallography and molecular dynamics." *FEBS J.*, 274:5077-5089, 2007.

DeLuna et al., "Exposing the fitness contribution of duplicated genes," *Nat. Genet.*, 40:676-681, 2008.

Deutscher et al., "Multiple knockout analysis of genetic robustness in the yeast metabolic network," *Nat. Genet.*, 38(9):993-998, 2006.

Draper et al., "Mutations in the genes encoding 11β-hydroxysteroid dehydrogenase type 1 and hexose-6-phosphate dehydrogenase interact to cause cortisone reductase deficiency," *Nature Genetics*, 34(4):434-439, 2003.

Fong et al., "Inhibition of poly(ADP-ribose) polymerase in tumors from BRCA mutation carriers," *N Engl J Med*, 361:123-134, 2009.

Guha-Chowdhury et al., "Inhibition of purified enolases from oral bacteria by fluoride," *Oral Microbiol. Immunol.*, 12(2):91-97, 1997.

Henrich et al., "CAMTA1, a 1p36 tumor suppressor candidate, inhibits growth and activates differentiation programs in neuroblastoma cells," *Cancer Res.*, 71(8):3142-3151, 2011.

Hillenmeyer et al., "Systematic analysis of genome-wide fitness data in yeast reveals novel gene function and drug action," *Genome Biology*, 11:R30, 2010.

Joseph et al., "Enolase activity and isoenzyme distribution in human brain regions and tumors," *J. Neurochem.*, 66(6):2484-2490, 1996.

Nijhawan et al., "Cancer vulnerabilities unveiled by genomic loss," *Cell*, 150:842-854, 2012.

PCT International Preliminary Report on Patentability issued in International Application No. PCT/US2012/069767, mailed Jun. 26, 2014.

PCT International Search Report and Written Opinion issued in International Application No. PCT/US2012/069767, mailed Jun. 26, 2013.

Suter et al., "Yeast-based functional genomics and proteomics technologies: the first 15 years and beyond," *BioTechniques*, 40:625-644, 2006.

Vavouri et al., "Widespread conservation of genetic redundancy during a billion years of eukaryotic evolution," *Trends Genet.*, 24:485-488, 2008.

Wise et al., "Glutamine addiction: a new therapeutic target in cancer," *Trends Biochem. Sci.*, 35(8):427-433, 2010.

Office Action issued in Chinese Application No. 201280069681.6, mailed Jul. 20, 2015.

Chen et al., "Gene deletion chemoselectivity: codeletion of the genes for p16$^{INK4}$, methylthioadenosine phosphorylase, and the α- and β-interferons in human pancreatic cell carcinoma lines and its implications for chemotherapy," *Cancer Research*, 56:1083-1090, 1996.

Eisenberg et al., "Human housekeeping genes are compact," *Trends in Genetics*, 19(7):362-365, 2003.

Ferrari et al., "A lethal combination for cancer cells: synthetic lethality screenings for drug discovery," *European Journal of Cancer*, 46(16):2889-2895, 2010.

Godthelp et al., "Mammalian Rad51C contributes to DNA cross-link resistance, sister chromatid cohesion and genomic stability," *Nucleic Acids Research*, 30(10):2172-2182, 2002.

Kaelin, "The concept of synthetic lethality in the context of anti-cancer therapy," *Nature Reviews Cancer*, 5(9):689-698, 2005.

Kamb, "Consequences of nonadaptive alterations in cancer," *Molecular Biology of the Cell*, 14(6):2201-2205, 2003.

Muller et al., "Passenger deletions generate therapeutic vulnerabilities in cancer," *Nature*, 488(7411):337-342, 2012.

Onyango et al., "Molecular cloning and expression analysis of five novel genes in chromosome 1p36," *Genomics*, 50(2):187-198, 1998.

Partial Supplementary European Search Report issued in European Application No. 12858619.5, mailed Aug. 3, 2015.

Vaz et al., "Mutation of the RAD51C gene in a Fanconi anemia-like disorder," *Nature Genetics*, 42(5):406-409, 2010.

Aksoy et al., "Prediction of individualized therapeutic vulnerabilities in cancer from genomic profiles," *Bioinformatics*, 30(14):2051-2059, 2014.

Hoffman et al., "Functional epigenetics approach identifies BRM/SMARCA2 as a critical synthetic lethal target in BRG1-deficient cancers," *Proc Natl Acad Sci USA*, 111(8):3128-3133, 2014.

Oike et al., "A synthetic lethality-based strategy to treat cancers harboring a genetic deficiency in the chromatin remodeling factor BRG1," *Cancer Res.*, 73(17):5508-5518, 2013.

Shahmoradgoli et al., "Antisense oligonucleotides targeting ENO2 have selective anti-proliferative effects in Glioblastoma Cells with 1p36 genomic loss," Poster, AACR-NCI-EORTC International Conference, Molecular Targets and Cancer Therapeutics, Boston, MA, Nov. 2015.

Shahmoradgoli et al., "Antisense oligonucleotides targeting ENO2 have selective anti-proliferative effects in Glioblastoma Cells with 1p36 genomic loss," Presentation Abstract, AACR-NCI-EORTC International Conference, Molecular Targets and Cancer Therapeutics, Boston, MA, Nov. 2015.

Vangamudi et al., "The SMARCA2/4 ATPase Domain Surpasses the Bromodomain as a Drug Target in SWI/SNF-Mutant Cancers: Insights from cDNA Rescue and PFI-3 Inhibitor Studies," *Cancer Res.*, 75(18):3865-3878, 2015.

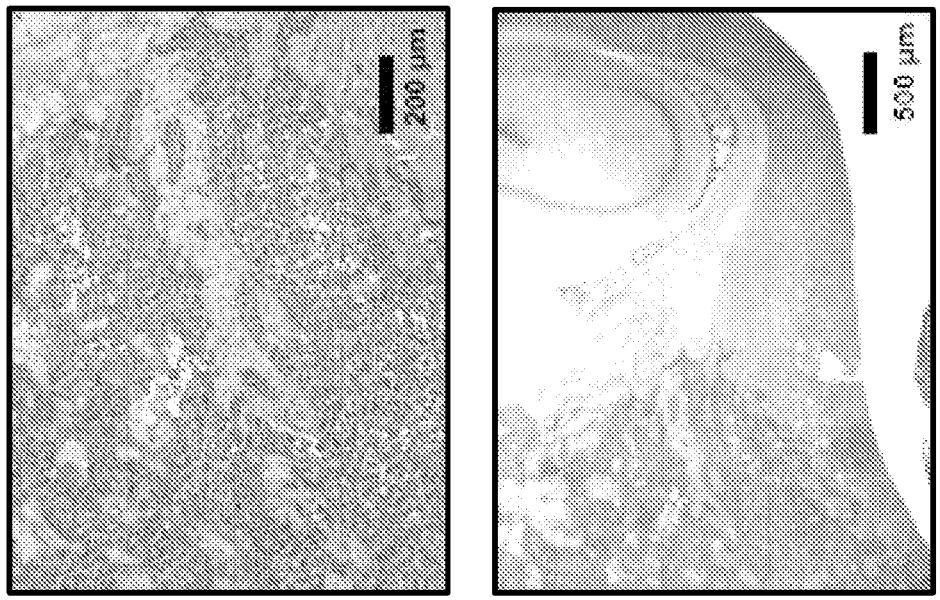
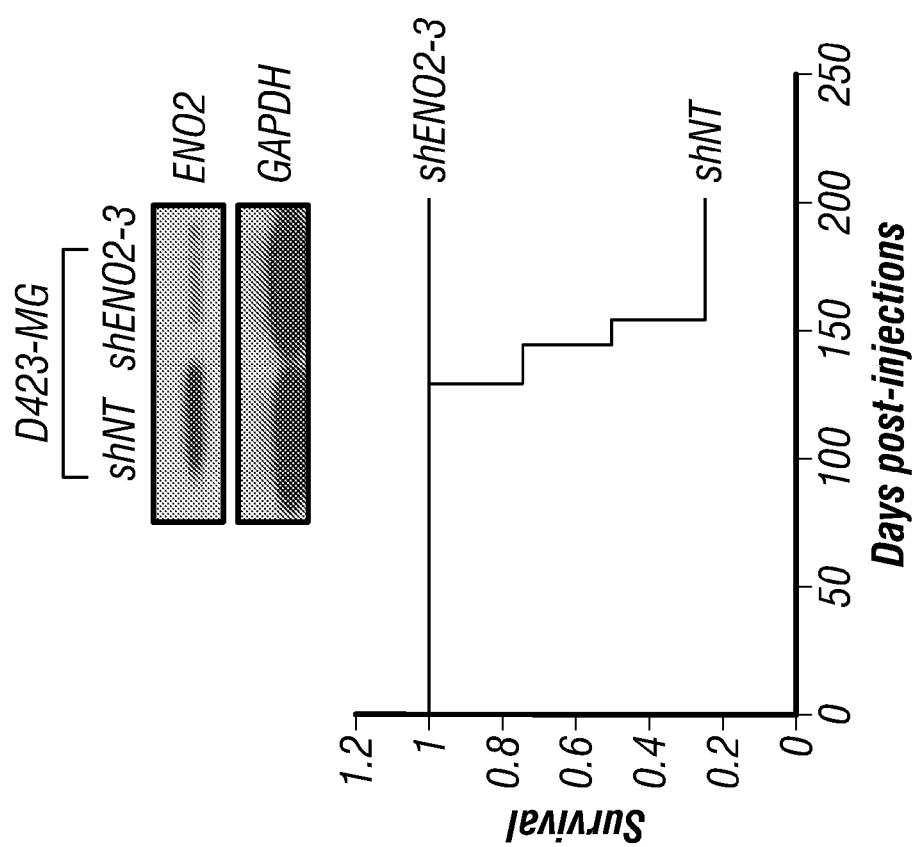
FIG. 1E

|   |   |   |   |            |
|---|---|---|---|------------|
| − | − | + | + | shENO2-4   |
| + | + | − | − | shENO2-3   |
| − | + | − | + | Doxycycline |
D423-MG (ENO1 null)
Enolase 2
Vinculin
A1207 (ENO1 WT)
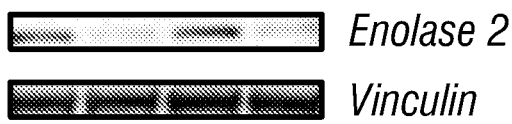
Enolase 2
Vinculin
U87 (ENO1 WT)
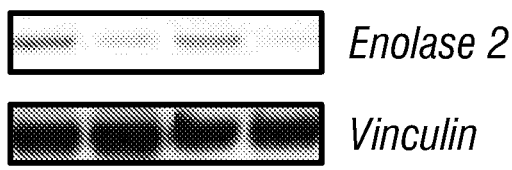
Enolase 2
Vinculin
LN319 (ENO1 WT)
Enolase 2
Vinculin
*FIG. 2A*

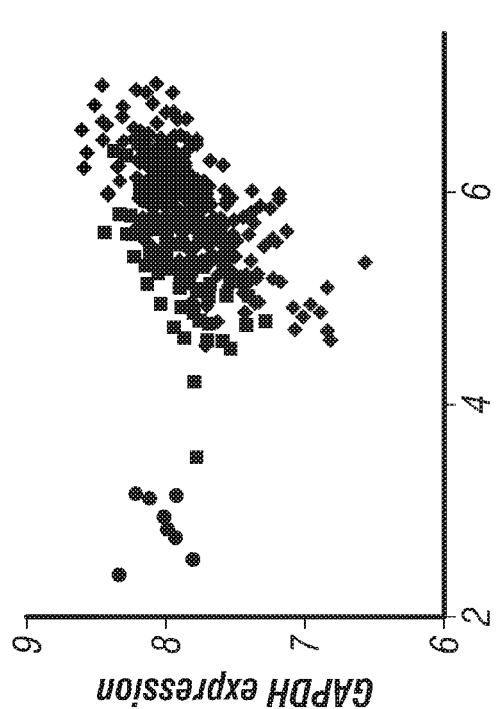
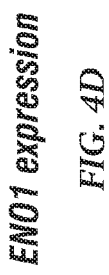
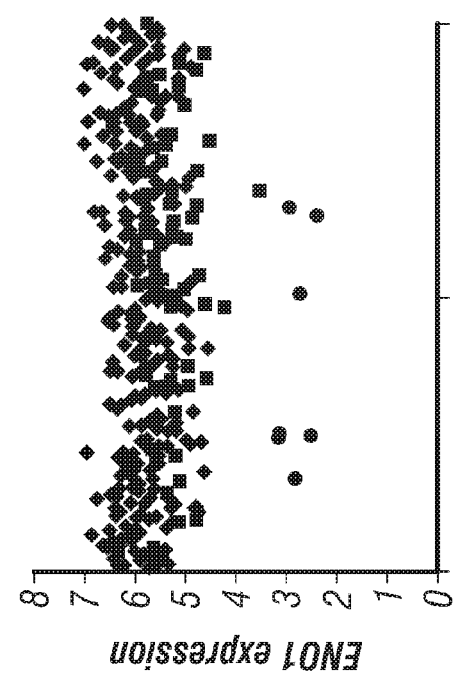
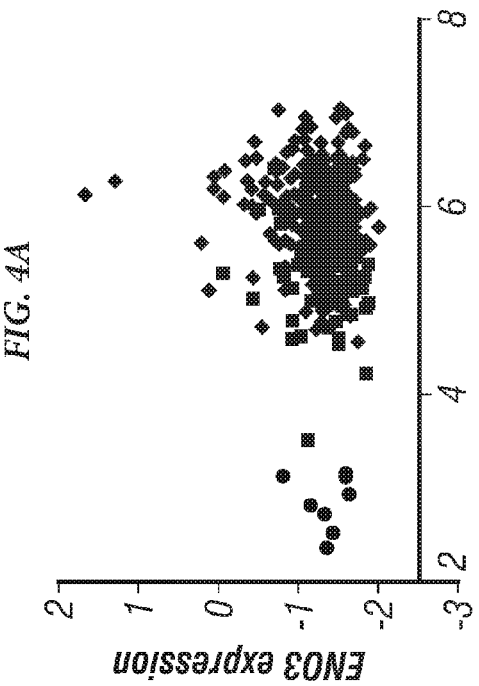

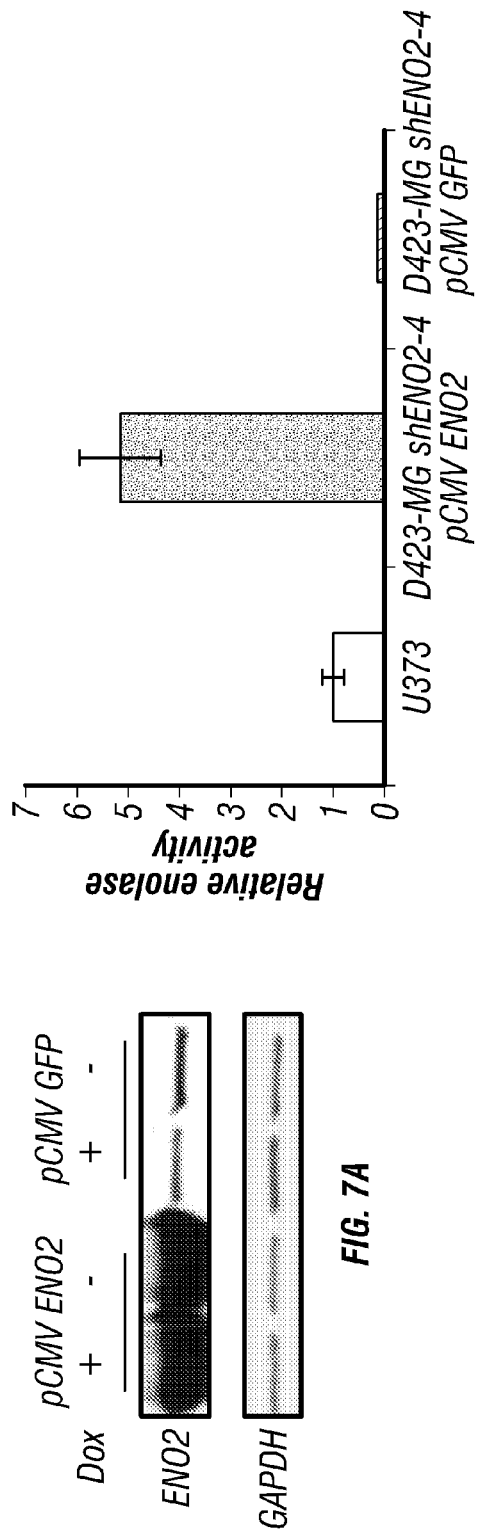
FIG. 7A
FIG. 7B
FIG. 7C
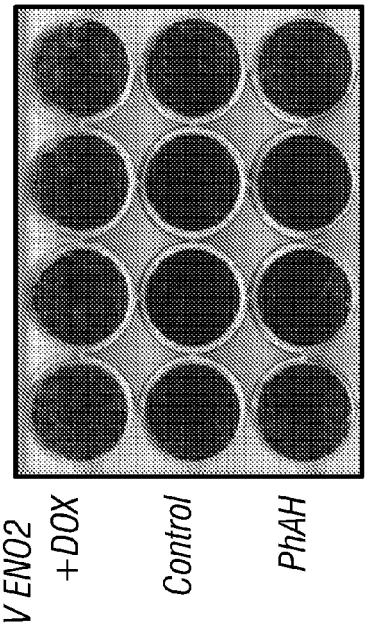
FIG. 7D

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
caagggagtc atcaaggaca a                                                    21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
cgcctggcta ataaggcttt a                                                    21

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
cggccttcaa cgtgatcaa                                                       19

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
gggactgaga acaaatcc                                                        18
```

COLLATERAL GENE INACTIVATION BIOMARKERS AND TARGETS FOR CANCER THERAPY

This application is a national phase application under 35 U.S.C. §371 of International Application No. PCT/US2012/069767, filed Dec. 14, 2012, which claims the benefit of U.S. Provisional Patent Application Nos. 61/570,366, filed Dec. 14, 2011, and 61/652,738, filed May 29, 2012, all of which are incorporated herein by reference in their entirety.

The invention was made with government support under Grant No. P01CA95616 awarded by the National Institutes of Health. The government has certain rights in the invention.

The sequence listing that is contained in the file named "UTFCP1138WO_ST25.txt", which is 2 KB (as measured in Microsoft Windows®) and was created on Dec. 14, 2012, is filed herewith by electronic submission and is incorporated by reference herein.

BACKGROUND OF THE INVENTION

1. Field of the Invention

The present invention relates generally to the field of molecular biology and oncology. More particularly, it concerns methods for identifying and treating cancers that have one copy of an essential gene functionally inactivated (e.g., by deletion or mutation of all or part of the gene coding sequence, epigenetic silencing of a locus, among other mechanisms).

2. Description of Related Art

Successful treatment of cancer has remained elusive despite rapid advances in the field in recent years. One major complicating factor in effective treatment is that conventional diagnostic analyses for tumor characterization (e.g., by pathological examination) offer limited guidance as to what types of anti-cancer therapy may be successful for treating any given cancer. In fact, cancer cells exhibit a wide range of resistance/susceptibility to various anti-cancer therapies, thus it has been difficult to predict whether a particular cancer will be resistant or susceptible to a given therapy. To address this issue genetic analysis of tumor cells has recently been be used to further characterize the specific cancer cells in patients. However, the results of such analyses typically show a plethora of genetic changes in the cancer and often do not provide a useful guide for therapeutic intervention. For example, heterozygous deletion of large regions of the genome is a prototypic somatic event in cancer. In many cases, the genetic instability exhibited by cancer cells drives tumor genesis by ablating the function of critical tumor suppressor genes. However, deletions are often large and can encompass neighboring genes with no known role in cancer pathogenesis. To date there has been no guidance as to how such mutations in tumor cells could be harnessed to improve cancer diagnosis or therapy.

SUMMARY OF THE INVENTION

Embodiments of the invention are based upon the discovery that some cancers have homozygous deletions in redundant housekeeping genes, and that this can be therapeutically exploited by targeting the non-deleted redundant homologue. Likewise, it has been recognized that cancers comprising heterozygous deletions in housekeeping genes are also rendered susceptible to therapeutic treatment targeting the non-deleted copy of the housekeeping gene. In still a further embodiment it is contemplated that cancer cells comprising heterozygous deletions in two (or more) housekeeping genes are rendered susceptible to, and can be treated with, therapeutic treatment targeting the non-deleted copy of each of the housekeeping genes that comprise the heterozygous deletion.

In one aspect, embodiments of the invention provide methods of treating a cancer in a subject. The cancer has a homozygous deletion in a housekeeping gene and the housekeeping gene has a functionally redundant homologue. The subject is treated by contacting the cell with an inhibitor of the redundant homologue in an amount sufficient to inhibit the activity of the redundant homologue.

In another aspect, embodiments of the invention provide methods of impairing cell proliferation and or inducing cell death of a cell. The cell has a homozygous deletion in a housekeeping gene and the housekeeping gene has a functionally redundant homologue. Cell proliferation and/or cell death is induced by contacting the cell with an inhibitor of the redundant homologue in an amount sufficient to inhibit the activity of the redundant homologue.

Optionally, the cell is further contacted with a chemotherapeutic agent. In some embodiments the chemotherapeutic agent interferes with DNA homeostasis.

The inhibitor can be, for example, a nucleic acid that inhibits the expression or activity of the redundant homologue, an antibody that specifically binds the redundant homologue or a small molecule. Inhibitors include for example phosphonoacetohydroxamate, dehydroepiandrosterone, Np2AD, Np4AD, Nap4AD, fluorocitrate or hopantenate or derivatives thereof.

In some aspects, the housekeeping gene is endolase 1 (ENO1) and the redundant homologue is endolase 2 (ENO2); the housekeeping gene is hexose-6-phosphate dehydrogenase (H6PD) and the redundant homologue is glucose-6 dehydrogenase (G6PD); the housekeeping gene is kinesin family member 1B (KIF1B) and the redundant homologue is a kinesin family member 1A (KIF1A) or kinesin family member 1C (KIF1A); the housekeeping gene is Nicotinamide nucleotide adenylyl transferase 1 (NMNAT1) and the redundant homologue is Nicotinamide nucleotide adenylyl transferase 2 (NMNAT2) or nicotinamide nucleotide adenylyl transferase 3 (NMNAT3); the housekeeping gene is ubiquitination factor E4B (UBE4B) and the redundant homologue is ubiquitination factor 4A (UBE4A); the housekeeping gene is aconitase 1 (ACO1) and the redundant homologue is aconitase 2 (ACO2) or aconitase 3 (ACO3); the housekeeping gene is kelch-like 9 (KLHL9) and the redundant homologue is kelch-like 13 (KLHL13); the housekeeping gene is pantothenate kinase 1 (PANK1) and the redundant homologue is pantothenate kinase 3 (PANK3); or the housekeeping gene is kinase family member 20B (KIF20B) and the redundant homologue is kinase family member 20A (KIF20A).

Also provided by embodiments of the invention are methods of assessing the effectiveness of a treatment regimen in a subject treated by the method according to the invention by measuring the level of one or more metabolites of the metabolic pathway of the housekeeping gene in a sample from the subject. An accumulation of the metabolite indicates that the treatment is efficacious. For example when the housekeeping gene is enolase and the metabolite is glycerate.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

In a further embodiment there is provided method for treating a subject having a cancer comprising administering at least a first glycolysis inhibitor to the subject, wherein it was determined that cells of the cancer comprise a heterozygous mutation that inactivates one copy of the Enolase 1 (ENO1) gene. Thus, in some aspects, a method is provided for treating a subject having a cancer comprising (a) selecting a subject determined to comprise cancer cells having a heterozygous mutation that inactivates one copy of the ENO1 gene; and (b) administering at least a first glycolysis inhibitor to the subject.

In a further embodiment, a method is provided for selecting a subject having a cancer for a glycolysis inhibitor therapy (i.e., therapy with a first glycolysis inhibitor) comprising determining whether cancer cells of the subject comprise a heterozygous mutation that inactivates one copy of the ENO1 gene, wherein if the cancer cells comprise the heterozygous mutation, then the subject is selected for a glycolysis inhibitor therapy. In a further aspect a method is provided for selecting a subject having a cancer for a glycolysis inhibitor therapy comprising (a) determining whether cancer cells of the subject comprise a heterozygous mutation that inactivates one copy of the ENO1 gene; and (b) selecting a subject for a glycolysis inhibitor therapy if cancer cells of the subject comprise the heterozygous mutation.

In still a further embodiment, a method is provided for predicting a response to a glycolysis inhibitor therapy in a subject having a cancer comprising determining whether cancer cells of the subject comprise a heterozygous mutation that inactivates one copy of the ENO1 gene, wherein if the cancer cells comprise the heterozygous mutation, then the subject is predicted to have a favorable response to a glycolysis inhibitor therapy. In a further aspect, there is provided a method for predicting a response to a glycolysis inhibitor therapy in a subject having a cancer comprising (a) determining whether cancer cells of the subject comprise a heterozygous mutation that inactivates one copy of the ENO1 gene; and (b) identifying the subject as predicted to have a favorable response to a glycolysis inhibitor therapy, if cancer cells from the subject comprise the heterozygous mutation; or identifying the subject as not predicted to have a favorable response to a glycolysis inhibitor therapy, if cancer cells from the subject do not comprise the heterozygous mutation.

In still a further embodiment there is provided method for treating a subject having a cancer comprising administering at least a t-RNA synthetase (ARS) inhibitor to the subject, wherein it was determined that cells of the cancer comprise a heterozygous mutation that inactivates one copy of an ARS gene. Thus, in some aspects, a method is provided for treating a subject having a cancer comprising (a) selecting a subject determined to comprise cancer cells having a heterozygous mutation that inactivates one copy of an ARS gene; and (b) administering at least a first ARS inhibitor to the subject.

In a further embodiment, a method is provided for selecting a subject having a cancer for an ARS inhibitor therapy (i.e., therapy with a first ARS inhibitor) comprising determining whether cancer cells of the subject comprise a heterozygous mutation that inactivates one copy of an ARS gene, wherein if the cancer cells comprise the heterozygous mutation, then the subject is selected for an ARS inhibitor therapy. In a further aspect a method is provided for selecting a subject having a cancer for an ARS inhibitor therapy comprising (a) determining whether cancer cells of the subject comprise a heterozygous mutation that inactivates one copy of an ARS gene (or two or more ARS genes); and (b) selecting a subject for an ARS inhibitor therapy if cancer cells of the subject comprise the heterozygous mutation.

In still a further embodiment, a method is provided for predicting a response to an ARS inhibitor therapy in a subject having a cancer comprising determining whether cancer cells of the subject comprise a heterozygous mutation that inactivates one copy of an ARS gene, wherein if the cancer cells comprise the heterozygous mutation, then the subject is predicted to have a favorable response to an ARS inhibitor therapy. In a further aspect, there is provided a method for predicting a response to an ARS inhibitor therapy in a subject having a cancer comprising (a) determining whether cancer cells of the subject comprise a heterozygous mutation that inactivates one copy of an ARS gene; and (b) identifying the subject as predicted to have a favorable response to an ARS inhibitor therapy, if cancer cells from the subject comprise the heterozygous mutation; or identifying the subject as not predicted to have a favorable response to an ARS inhibitor therapy, if cancer cells from the subject do not comprise the heterozygous mutation.

In a further embodiment there is provided method for treating a subject having a cancer comprising administering at least a first phosphogluconate dehydrogenase inhibitor to the subject, wherein it was determined that cells of the cancer comprise a heterozygous mutation that inactivates one copy of the phosphogluconate dehydrogenase (PGD) gene. Thus, in some aspects, a method is provided for treating a subject having a cancer comprising (a) selecting a subject determined to comprise cancer cells having a heterozygous mutation that inactivates one copy of the PGD gene; and (b) administering at least a first phosphogluconate dehydrogenase inhibitor (e.g., 6-aminonicotinamide) to the subject.

In a further embodiment, a method is provided for selecting a subject having a cancer for a phosphogluconate dehydrogenase inhibitor therapy (i.e., therapy with a first phosphogluconate dehydrogenase inhibitor) comprising determining whether cancer cells of the subject comprise a heterozygous mutation that inactivates one copy of the PGD gene, wherein if the cancer cells comprise the heterozygous mutation, then the subject is selected for a phosphogluconate dehydrogenase inhibitor therapy. In a further aspect a method is provided for selecting a subject having a cancer for a phosphogluconate dehydrogenase inhibitor therapy comprising (a) determining whether cancer cells of the subject comprise a heterozygous mutation that inactivates one copy of the PGD gene; and (b) selecting a subject for a phosphogluconate dehydrogenase inhibitor therapy if cancer cells of the subject comprise the heterozygous mutation.

In still a further embodiment, a method is provided for predicting a response to a phosphogluconate dehydrogenase inhibitor therapy in a subject having a cancer comprising determining whether cancer cells of the subject comprise a heterozygous mutation that inactivates one copy of the PGD gene, wherein if the cancer cells comprise the heterozygous mutation, then the subject is predicted to have a favorable response to a phosphogluconate dehydrogenase inhibitor therapy. In a further aspect, there is provided a method for predicting a response to a phosphogluconate dehydrogenase inhibitor therapy in a subject having a cancer comprising (a) determining whether cancer cells of the subject comprise a heterozygous mutation that inactivates one copy of the PGD gene; and (b) identifying the subject as predicted to have a favorable response to a phosphogluconate dehydrogenase inhibitor therapy, if cancer cells from the subject comprise the heterozygous mutation; or identifying the subject as not predicted to have a favorable response to a phosphogluconate dehydrogenase inhibitor therapy, if cancer cells from the subject do not comprise the heterozygous mutation.

In a further embodiment there is provided method for treating a subject having a cancer comprising administering at least a first glycolysis inhibitor to the subject, wherein it was determined that cells of the cancer comprise a heterozygous mutation that inactivates one copy of the GAPDH, ENO2 and/or TPI genes (each located at 12p13). Thus, in some aspects, a method is provided for treating a subject having a cancer comprising (a) selecting a subject determined to comprise cancer cells having a heterozygous mutation that inactivates one copy of the GAPDH, ENO2 and/or TPI genes; and (b) administering at least a first glycolysis inhibitor to the subject.

In a further embodiment, a method is provided for selecting a subject having a cancer for a glycolysis inhibitor therapy (i.e., therapy with a first glycolysis inhibitor) comprising determining whether cancer cells of the subject comprise a heterozygous mutation that inactivates one copy of the GAPDH, ENO2 and/or TPI genes, wherein if the cancer cells comprise the heterozygous mutation, then the subject is selected for a glycolysis inhibitor therapy. In a further aspect, a method is provided for selecting a subject having a cancer for a glycolysis inhibitor therapy comprising (a) determining whether cancer cells of the subject comprise a heterozygous mutation that inactivates one copy of the GAPDH, ENO2 and/or TPI genes; and (b) selecting a subject for a glycolysis inhibitor therapy if cancer cells of the subject comprise the heterozygous mutation.

In still a further embodiment, a method is provided for predicting a response to a glycolysis inhibitor therapy in a subject having a cancer comprising determining whether cancer cells of the subject comprise a heterozygous mutation that inactivates one copy of the GAPDH, ENO2 and/or TPI genes, wherein if the cancer cells comprise the heterozygous mutation, then the subject is predicted to have a favorable response to a glycolysis inhibitor therapy. In a further aspect, there is provided a method for predicting a response to a glycolysis inhibitor therapy in a subject having a cancer comprising (a) determining whether cancer cells of the subject comprise a heterozygous mutation that inactivates one copy of the GAPDH, ENO2 and/or TPI genes; and (b) identifying the subject as predicted to have a favorable response to a glycolysis inhibitor therapy, if cancer cells from the subject comprise a heterozygous mutation; or identifying the subject as not predicted to have a favorable response to a glycolysis inhibitor therapy, if cancer cells from the subject do not comprise one of the heterozygous mutations.

Certain aspects of the embodiments concern cancers that comprise a heterozygous mutation that inactivates one copy an essential gene, such as one copy of the ENO1, an ARS gene, the PGD gene, the GAPDH gene, the ENO2 gene and/or the TPI gene. As used herein a "heterozygous mutation" refers to a mutation in only one of the two copies of the gene (in a diploid cell or of the loss of one in a triploid cell, or more broadly, loss of all but one copy in a polyploid cell).

For example, the heterozygous mutation can be a deletion, substitution, inversion, rearrangement or insertion that functionally inactivated one copy of ENO1. In some aspects, the mutation is a deletion, such as a loss of heterozygosity at chromosome 1p36. Thus, in certain aspects, a heterozygous deletion can encompass more than ENO1 gene, such as a deletion that inactivates ENO1 as well as RERE, CA6 and/or SLC2A7. For example, in some aspects a method of the embodiments can involve determining a deletion 5' and 3' of ENO1 and thereby determine that ENO1 is inactivated (deleted) indirectly. Examples of genes position 5' to ENO1 include, without limitation, NPHP4, KCNAB2, CHD5, RPL22, RNF207, C1orf211, GPR153, ICMT, HES3, ACOT7, TNFRSF25, PLEKHG5, DNAJC11, HES2, ESPN, MIR4252, NOL9, TAS1R1, ZBTB48, KLHL21, PHF13, THAP3, CAMTA1, VAMP3, PER3, UTS2, TNFRSF9, TRNA_Pseudo, PARK7, AX747125, ERRFI1, SLC45A1, RERE and BC113958. Non-limiting examples of genes position 3' to ENO1 include, CA6, SLC2A7, SLC2A5, GPR157, mir-34, MIR34A, H6PD, SPSB1, 5S rRNA, SLC25A33, TMEM201, PIK3CD, C1orf200, BC038541, CLSTN1, CTNNBIP1, LZIC, NMNAT1, RBP7, UBE4B, KIF1B, APITD1-CORT, PEX14, CASZ1, Mir 584, PGD, APITD1, CORT, DFFA, C1orf127, TARDBP, MASP2, SRM, MTOR, ANGPTL7, EXOSC10, UBIAD1, PTCHD2, FBXO2, FBXO44, FBXO6, MAD2L2, C1orf187, AK125437, AGTRAP, C1orf167, MTHFR, CLCN6, NPPA-AS1, NPPA, NPPB, KIAA2013, PLOD 1 and MFN2. In certain aspects, a cancer comprises a heterozygous mutation wherein an entire arm of chromosome 1 is lost. In certain cases, a heterozygous deletion of ENO1 can be determined by cytogenetic chromosome spreads or copy number analysis of random DNA fragments upstream and downstream of the ENO1 gene.

In some aspects, the heterozygous mutation can be a deletion, substitution, inversion, rearrangement or insertion that functionally inactivated one copy of GAPDH, ENO2 and/or TPI genes. In some aspects, the mutation is a deletion, such as a loss of heterozygosity at chromosome 12p13. Thus, in certain aspects, a heterozygous deletion can encompass more than GAPDH, ENO2 and/or TPI genes, such as a deletion that inactivates two or all three of the genes.

In a further example, the heterozygous mutation can be a deletion, substitution, inversion, rearrangement or insertion that functionally inactivated one copy of an ARS gene, such one copy of the EPARS (aka EPRS), VARS, IARS, CARS, SARS, YARS, AARS, KARS, LARS, HARS, RARS or TARS gene. In some aspects, the mutation is a deletion, such as a loss of heterozygosity at a chromosomal locus comprising the gene. For example, a cancer cell can comprise a loss of heterozygosity at 5q13, 1q41, 6p21, 9q24, 11p15, 1p13, 1p35, 16q13, 16q24, 5q31, 5q32 or 5q35. Thus, in certain aspects, a heterozygous deletion can encompass more than one ARS gene, such as a deletion that inactivates SARS as well as YARS; AARS and KARS; LARS and HARS or LARS HARS and RARS.

In still a further example, the heterozygous mutation can be a deletion, substitution, inversion, rearrangement or insertion that functionally inactivated one copy of a PGD gene. In some aspects, the mutation is a deletion, such as a loss of heterozygosity at a chromosomal locus comprising the gene, e.g., comprising 1p36.22. In certain aspects, a deletion can encompass additional portions of the chromosome 1p. For example, a cancer cell can comprise a deletion that comprises ENO1 and PGD. Thus, in some aspects, a cancer identified as comprising an inactivation of one copy of both ENO1 and PGD can be treated with at least a first glycolysis inhibitor in conjunction with a PGD inhibitor, such as 6-aminonicotinamide.

Some aspects of the embodiments concern administration at least a first glycolysis inhibitor to a subject (e.g., a subject having a mutation in one copy of an ENO1 gene). Examples of glycolysis inhibitors include, with limitation inhibitors of pyruvate kinase (e.g., PKLR1 or PKM2), enolase (e.g., ENO1, ENO2 or ENO3), phosphoglycerate mutase (e.g., PGM1, PGM2, PGM2L1, PGM3 or PGM5), phosphoglycerate kinase (e.g., PGK1 or PGK2), glyceraldehydes phosphate dehydrogenase (GAPDH), triosephosphate isomerase (TPI), fructose biphosphate aldolase (e.g., Aldoa, Aldob or Aldoc), phosphofructokinase (PFKL, PFKM or PFKP), phosphoglucose isomerase (GPI) and hexokinase (e.g., HK1, HK2 or HK3). In further aspects, the inhibitor is an inhibitor of the mitochondrial electron transport chain. In some aspects, the glycolysis inhibitor is an inhibitory polynucleotide (e.g., an siRNA, shRNA or miRNA) such as an inhibitory polynucleotide complementary to all or part of a gene encoding a pyruvate kinase, enolase (e.g., ENO1), phosphoglycerate mutase, phosphoglycerate kinase, glyceraldehydes phosphate dehydrogenase, triosephosphate isomerase, fructose biphosphate aldolase, phosphofructokinase, phosphoglucose isomerase and hexokinase. In still further aspects, the glycolysis inhibitor is a small molecule inhibitor or a prodrug thereof. Examples, of glycolysis inhibitors for use according to embodiments include, without limitation, 2-deoxyglucose, 6-aminonicotinamide, tetrose diphosphate, koningic acid and MJE3.

In certain preferred aspects, a glycolysis inhibitor for use as a therapeutic is selected based on the heterozygous gene inactivation identified in the cancer. For example, if the cancer cell comprises a heterozygous inactivation of ENO1 then the glycolysis inhibitor therapy can comprise an enolase inhibitor. Likewise, in the case of a cancer has a heterozygous inactivation of a GAPDH, ENO2 or TPI gene, a glycolysis inhibitor therapy can comprise a GAPDH, enolase or TPI inhibitor, respectively. In certain aspects, a cancer cell comprises a heterozygous inactivation of two or genes in the glycolysis pathway and a glycolysis inhibitor therapy comprises an inhibitor of each of the genes subject to the heterozygous deletion.

In some preferred aspects, a glycolysis inhibitor for use according to the embodiments is an enolase inhibitor, such as an enolase 1 inhibitor. For example, the enolase 1 inhibitor can be an inhibitory polynucleotide, such as a siRNA, shRNA or miRNA complementary to all or part of an ENO1 gene (e.g., complementary to all or part of an enolase 1 coding mRNA, see, e.g., NCBI accession nos. NM_001201483.1 or NM_001428.3). In still further aspects, the enolase inhibitor is a small molecule enolase inhibitor or a prodrug thereof. Examples of small molecule enolase inhibitors include, without limitation, D-tartronate semialdehyde phosphate; 3-aminoenolpyruvate-2-phosphate; phosphonoacetohydroaxamate (PhAH); 2-fluoro-2-phosphonoacetohydroxamate; (3-hydroxy-2-nitropropyl) phosphonate; (nitroethyl)phosphonate; d-(phosphonoethyl) nitrolate; fluorides and prodrugs of any of the foregoing.

Examples of ARS inhibitors for use according to the embodiments include, without limitation Borrelidin or produgs thereof. In still further aspects the ARS inhibitor is a febrifugine derivative, such as halofuginone (see, e.g., Sundrud et al., 2009 and Keller et al., 2012, incorporated herein by reference). In some aspects, the ARS inhibitor is antimicrobial ARS inhibitor. In still further aspects the ARS inhibitor can be an inhibitory polynucleotide, such as a siRNA, shRNA or miRNA complementary to all or part of an ARS gene. In certain aspects, an ARS inhibitor is administered in conjunction with a further inhibitor of protein synthesis or an activator of amino acid starvation response.

Examples of PGD inhibitors for use according to the embodiments include, for example, 6-aminonicotinamide or produgs thereof. In some aspects, the PGD inhibitor can be an inhibitory polynucleotide, such as a siRNA, shRNA or miRNA complementary to all or part of the PGD gene (see, e.g., NCBI accession no. NM_002631.2).

Targeted inhibitors therapies (e.g., glycolysis PGD or ARS inhibitors) for administration according to the embodiments are typically formulated in a pharmaceutically acceptable carrier. Such a therapy may be delivered, for example, intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, via inhalation (e.g. aerosol inhalation), by injection or by infusion. The route of delivery can depend, for example, upon the type of cancer to be treated and the type of inhibitor that is used. In further aspects, an inhibitor, such as a glycolysis, PDG or ARS inhibitor, can be administer two or more times (e.g., 3, 4, 5, 6, 7, 8, 9 or 10 times). The timing between doses of such a therapy can be varied and can include, without limitation, about 1, 2 or 3 days, about 1, 2, or 3 weeks or 1 month or more between doses.

In yet a further embodiment, there is provided a method for treating a subject having a cancer, comprising administering a targeted inhibitor therapy (e.g., a glycolysis, PDG or ARS inhibitor therapy) to the subject in conjunction with at least a second therapy. For example, the second therapy may be administered before, after or during the targeted inhibitor therapy. The timing between a targeted inhibitor therapy and a second therapy can be varied and can include, without limitation, about 1, 2 or 3 days, about 1, 2, or 3 weeks or 1 month or more between the therapies. The second anticancer therapy may be, without limitation, a surgical therapy, chemotherapy, cancer cell-targeted therapy, radiation therapy, cryotherapy, hyperthermia treatment, phototherapy, radioablation therapy, hormonal therapy, immunotherapy, small molecule therapy, receptor kinase inhibitor therapy, anti-angiogenic therapy, cytokine therapy or a biological therapy such as treatment with a monoclonal antibody, siRNA, antisense oligonucleotide, ribozyme or gene therapy. In still further aspects, the second therapy can comprise administration of a further, different, glycolysis inhibitor, such as an inhibitor that targets a different glycolysis pathway component relative to the first glycolysis inhibitor. In further aspects, the second therapy comprises administration of a mitochondrial electron transport chain inhibitor (e.g., mubritinib or oligomycin) or an inhibitor of the transcription factor Hiflα.

Some aspects of the embodiments involve a subject, such as a subject having a cancer. As used herein a subject can be human or non-human animal subject (e.g., a dog, cat, mouse, horse, etc). In certain aspects, the subject has a cancer, such as an oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, neuroendocrine tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In some aspects, the cancer is a glioma, a glioblastoma, oligodendroglioma or a large cell neuroendocrine lung tumor. In further aspects, the cancer can be a melanoma, such as an ocular/uveal melanoma. In still further aspects, the cancer is a metastatic cancer or a cancer that is resistant to a least a first chemotherapy.

Some aspects of the embodiments, concern determining whether cancer cells of a subject comprise a heterozygous mutation that inactivates one copy of the ENO1 gene. Examples of methods that can be used to determine whether cancer cells of the subject comprise the heterozygous mutation include, without limitation, DNA sequencing, polymerase chain reaction (PCR), nucleic acid hybridization (e.g., Southern blot or in situ hybridization) or DNA restriction analysis to detect an inactivating mutation (e.g., a deletion, rearrangement, substitution, insertion or inversion). In further aspects, a method of the embodiments can comprise measuring an enolase expression or enolase activity. For example, expression of an enolase 1 mRNA or protein can be measured and compared to reference expression level to determine whether cancer cells of a subject comprise a heterozygous mutation that inactivates one copy of the ENO1 gene. Methods for measuring RNA expression include, without limitation, nucleic acid hybridization (e.g., Northern blot, in situ hybridization or array hybridization) and quantitative reverse transcription PCR. Non-limiting examples of methods for measuring enolase 1 protein expression include performing an ELISA, an immunoassay, a radioimmunoassay (RIA), Immunohistochemistry, an immunoradiometric assay, a fluoroimmunoassay, a chemiluminescent assay, a bioluminescent assay, a gel electrophoresis, a Western blot analysis, flow cytometry, positron emission tomography (PET), or single photon emission computed tomography (SPECT) imaging. Likewise, in some aspects, enolase 1 activity can be measured (e.g., by measuring substrate catalysis) and compared to reference expression level to determine whether cancer cells of a subject comprise a heterozygous mutation that inactivates one copy of the ENO1 gene.

In some aspects, a biological sample (e.g., a sample comprising cancer cells or metabolites or nucleic acid therefrom) is obtained from a patient for analysis according to the embodiments. For example, the biological sample can be, without limitation, a blood, tissue (e.g., biopsy), urine, stool or saliva sample. In some aspects, the sample is a tumor biopsy sample.

In some aspects, a method of the embodiments further comprises reporting whether cancer cells of the subject comprise a heterozygous mutation that inactivates one copy of the ENO1 gene or an ARS gene. In still further aspects, a method can comprise reporting whether a subject was identified as predicted or not predicted to have a favorable response to a glycolysis inhibitor therapy (e.g., an enolase inhibitor therapy) or an ARS inhibitor therapy. For example, such reporting can be by providing a written, electronic or oral report. In some aspects, a report is provided to the subject. In still further aspects, the report is provided to a third party, such an insurance company or health care provider (e.g., a doctor or hospital).

Certain aspects of the embodiments concern predicting whether or not a subject will with have a favorable response to a glycolysis inhibitor therapy or an ARS inhibitor therapy. For example, a favorable response can be a reduction in tumor size or burden, blocking of tumor growth, reduction in tumor-associated pain, reduction in cancer associated pathology, reduction in cancer associated symptoms, cancer non-progression, increased disease free interval, increased time to progression, induction of remission, reduction of metastasis, increased patient survival or an increase in the sensitivity of the tumor to an anticancer therapy.

In yet a further embodiment there is provided a kit comprising at least a first glycolysis inhibitor (e.g., an enolase inhibitor) and at least a first reagent for testing cells for a heterozygous mutation that inactivates one copy of the ENO1 gene. For instance the glycolysis inhibitor can be any of those known in the art or detailed herein. In some aspects, the glycolysis inhibitor is an enolase inhibitor. Examples of reagents for use in testing cells include, without limitation, a nucleic acid molecule that bind with-in or adjacent to the ENO1 gene (e.g., an oligonucleotide primer), an anti-enolase 1 antibody and an enolase enzyme substrate (such as a labeled substrate).

Likewise, in a further embodiment, there is provided a kit comprising an ARS inhibitor and a reagent for testing cells for a heterozygous mutation that inactivates one copy of an ARS gene. Examples of reagents for use in testing cells include, without limitation, a nucleic acid molecule that bind with-in or adjacent to an ARS gene (e.g., an oligonucleotide primer), an anti-ARS antibody and an ARS enzyme substrate (such as a labeled substrate).

In yet a further embodiment, there is provided a method for monitoring the effectiveness of an enolase inhibitor therapy comprising determining the levels of glycerate and/or 1,3 dihydroxyacetone in a sample from a subject treated with an enolase inhibitor, wherein if the levels of glycerate or 1,3 dihydroxyacetone are not elevated as compared to a reference level the subject is in need of additional enolase inhibitor therapy and if the levels of glycerate or 1,3 dihydroxyacetone are elevated as compared to a reference level the subject is not in need of additional enolase inhibitor therapy. In some aspects a method is provided for monitoring the effectiveness of an enolase inhibitor therapy comprising (a) determining the levels of glycerate or 1,3 dihydroxyacetone in a sample from a subject treated with an enolase inhibitor; and (b) identifying the subject as in need of additional enolase inhibitor therapy if the levels of glycerate or 1,3 dihydroxyacetone are not elevated as compared to a reference level; or identifying the subject as not in need of additional enolase inhibitor therapy if the levels of glycerate or 1,3 dihydroxyacetone are elevated as compared to a reference level. In some aspects, a method of the embodiments further comprises administering an additional enolase inhibitor therapy to a subject based on the levels of glycerate or 1,3 dihydroxyacetone. In some further aspects, an additional enolase inhibitor therapy is an additional administration of an enolase inhibitor therapy or the administration of a higher dose of an enolase inhibitor. In yet further aspects, a method of the embodiments further comprises reporting a glycerate or 1,3 dihydroxyacetone level for a subject or reporting whether a subject is in need of additional enolase inhibitor therapy.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-E: Homozygous deletion of the 1p36 locus in GBM results in loss of ENO1 expression in primary tumors and cell lines. a, Affymetrix aCGH data from TCGA show four primary GBMs with log 2 copy number <−1 (actual values in white), indicating homozygous deletion of the 1p36 locus. b, DNA copy number correlates strongly with mRNA expression across primary GBMs; expression is highest in tumors with n=2 copies (WT, gray) and lowest in tumors with n=0 copies (null) of ENO1. c, The D423-MG cell line was identified as homozygously deleted by using SNP arrays from the Wellcome Trust Sanger Institute data set. d, The complete absence of enolase 1 protein in D423-MG and Gli56 cells was confirmed by western blotting. e, shRNA knock-down of ENO2 in D423-MG ENO1 null cells ablated intracranial tumorigenesis in vivo.

FIGS. 2A-B: shRNA ablation of ENO2 affects ENO1-null but not ENO1-WT GBM cells. a, shRNA ablation by two independent doxycycline (Dox)-inducible TRIPZ hairpins against ENO2 (shENO2-3, shENO2-4) resulted in >70% reduction in enolase 2 protein levels in both ENO1 WT (A1207, U87, LN319) and ENO1-null (D423-MG) cell lines. b, Ablation of ENO2 dramatically inhibited growth of ENO1-null but not ENO1 WT cells, whereas non-targeting shRNA against luciferase (shLuc) had no effect in any cell line. Representative plates at the last time point of growth for cells infected with shLuc, shENO2-3, or shENO2-4, with or without Dox induction, are shown alongside growth curves for each cell line.

FIGS. 4A-D: No overall reduction in glycolysis-related transcripts despite dramatic reduction of ENO1 mRNA expression in ENO1 homozygously deleted primary tumors. a, Affymetrix U133 microarray data (log 2 absolute mRNA expression plotted on the y axis) from the TCGA GBM data set show lowest ENO1 expression in ENO1 homozygously deleted primary tumors (red circles) and intermediate expression in heterozygously deleted tumors (green squares). b, expression of the major glycolysis gene GAPDH (y axis) versus ENO1 expression (x axis). c,d, Expression of ENO3 and ENO2 versus ENO1 expression; ENO3 expression is extremely low (note the differences in scale on the y axis). The major conclusion from these data is that there is no dramatic compensatory upregulation of ENO2 or ENO3 nor major alterations in GAPDH in ENO1-deleted tumors. This finding suggests that no major bioenergetic remodeling occurs in ENO1-null tumors.

FIGS. 7A-D: Expression of a hairpin-resistant ENO2 cDNA construct restores enolase activity and prevents the deleterious effects of shENO2 and PhAH in ENO1-null cells. a,b, A construct expressing hairpin-resistant ENO2 (or GFP as a control) was used to infect D423-MG cells already transduced with pTRIPZ shENO2-4, resulting in strong expression of enolase 2 protein irrespective of hairpin activation by doxycycline (a) as well as strong increase in overall enolase activity (b). c,d, Re-expression of hairpin-resistant ENO2 but not GFP prevented the deleterious effects of shENO2-4 induction by doxycycline. Note that the degree of growth inhibition by shENO2-4 in the control GFP experiment was somewhat lower than that yielded by the same cell clone in previous experiments before pCMV GFP infection (FIG. 3). This is attributed to the loss of ENO2 knockdown (compare the level of ENO2 knockdown in (a) with FIG. 3) during continuous culturing. Re-expression of ENO2 also conferred complete resistance to the enolase inhibitor PhAH (by restoring overall enolase activity to levels even higher than those in WT cells).

(Ink/arf) are well known to exhibit frequent and recurrent homozygous deletions in a number of different cancers. The FIG. shows SNP-array (copy number) changes around the 10q23 locus in multiple primary tumors. The deletions range widely in size and boundaries but are all anchored on PTEN. This type of pattern "minimally common region" has been extensively studied as a flag for the critical tumor suppressor gene targeted by the deletions (Maser et al., 2007). What has receive considerably less attention is that some of these deletions can be quite large and remove a number of non-target, non-tumor suppressor genes ("passenger") which may play an important, if redundant role in the cell. While most of these passenger deleted genes are irrelevant and not expressed in tumor tissue (e.g. Interferons, defensins), a number of ubiquitously expressed metabolic genes are co-deleted with PTEN, decreasing in frequency with increasing distance from PTEN. These include ATAD1 (a highly conserved mitochondrial AAA ATPase of unknown function), MINPP1 (An inositol polyphosphate phosphatase playing a role in glycolysis, riboflavin and carbohydrate metabolism, Cho et al., 2008) and PANK1 (Pantothenate kinase, the first step in the biosynthesis of Coenzyme A, an essential co-factor for acetyl transfer reactions, fatty acid oxidation and lipid biosynthesis, see e.g., Leonardi et al., 2010a and Leonardi et al., 2010b, incorporated herein by reference).

Figures 18A, 18B:
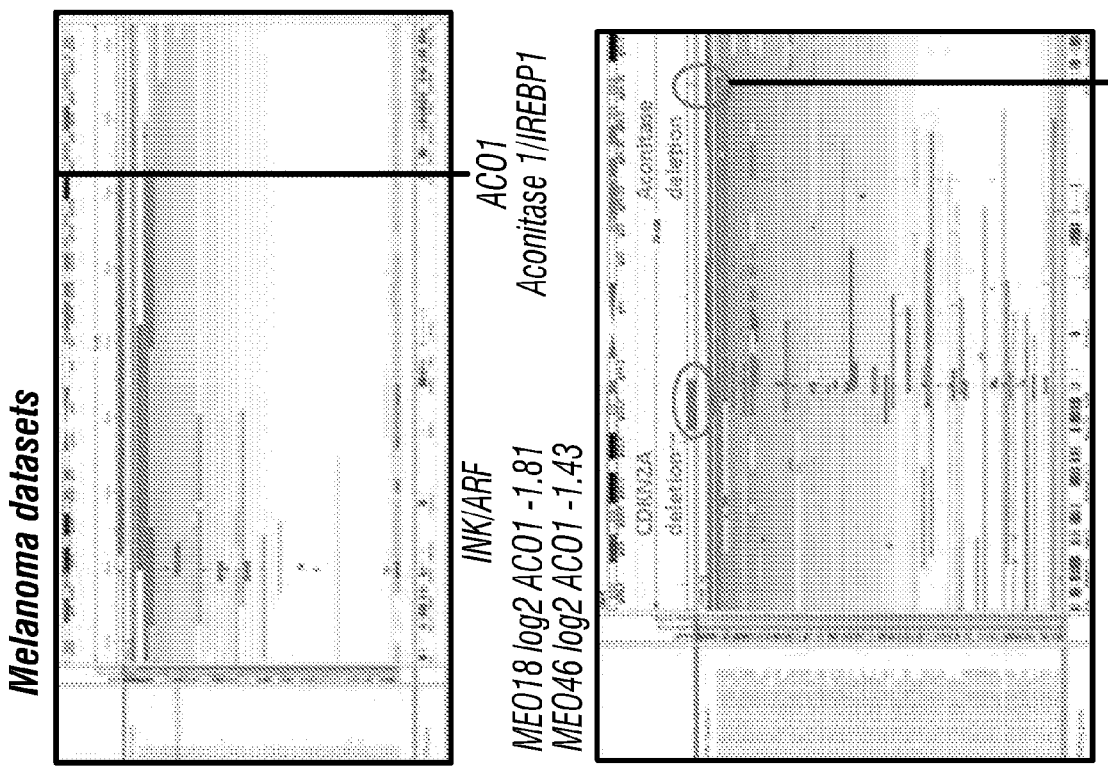

FIGS. 18A-B: Another example of essential redundant housekeeping genes deleted with major tumor suppressors. This figure shows copy number changes on chromosome 9 around the INK/ARF locus, a major tumor suppressor. In this case the gene ACO1, encoding for the TCA cycle enzyme aconitase 1 is deleted together with INK4a/ARF. Panel a shows that in two separate melanoma datasets ACO1 is homozygously deleted in two patient samples. Panel b shows that this homozygous deletion also occurs in 2/356 glioblastoma patients. Aconitase 1 is another important housekeeping gene which is a promising target for our therapeutic strategy.

Figure 19A:
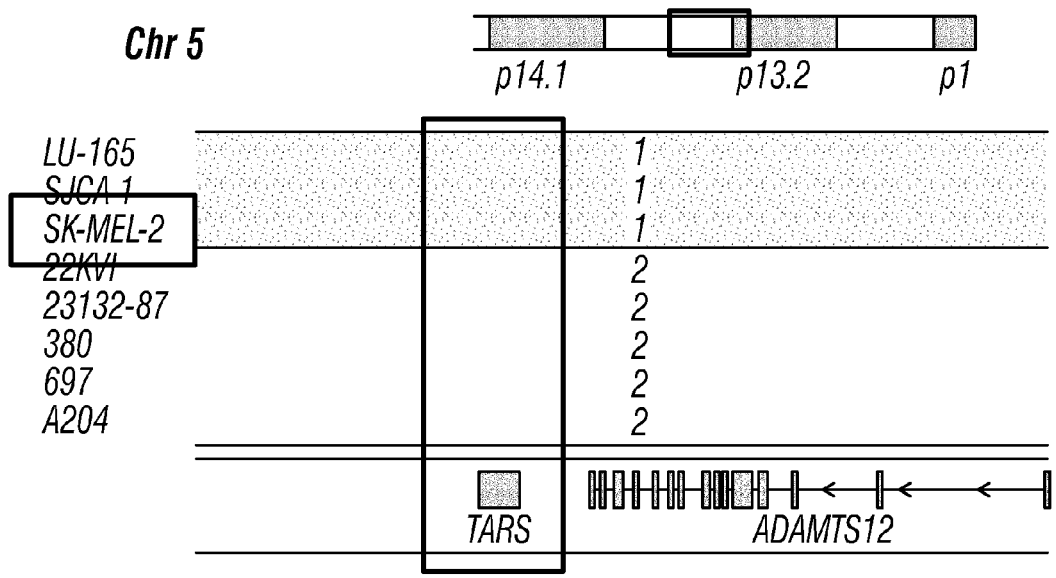
Figure 19B:
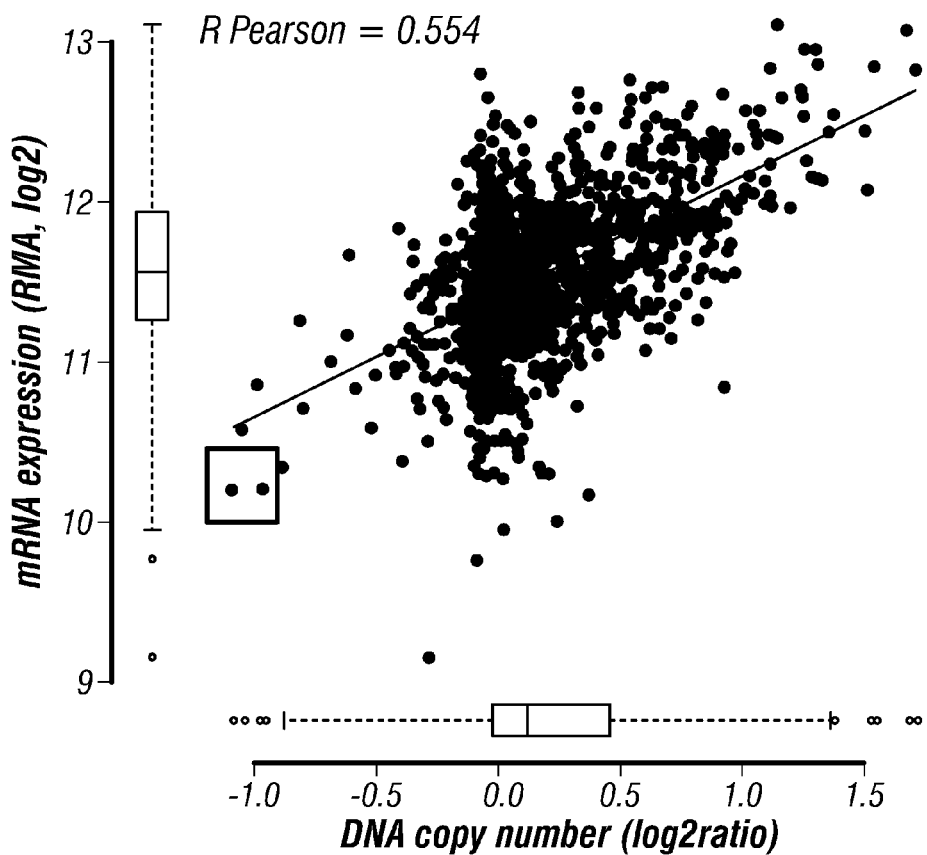
Figure 19C:
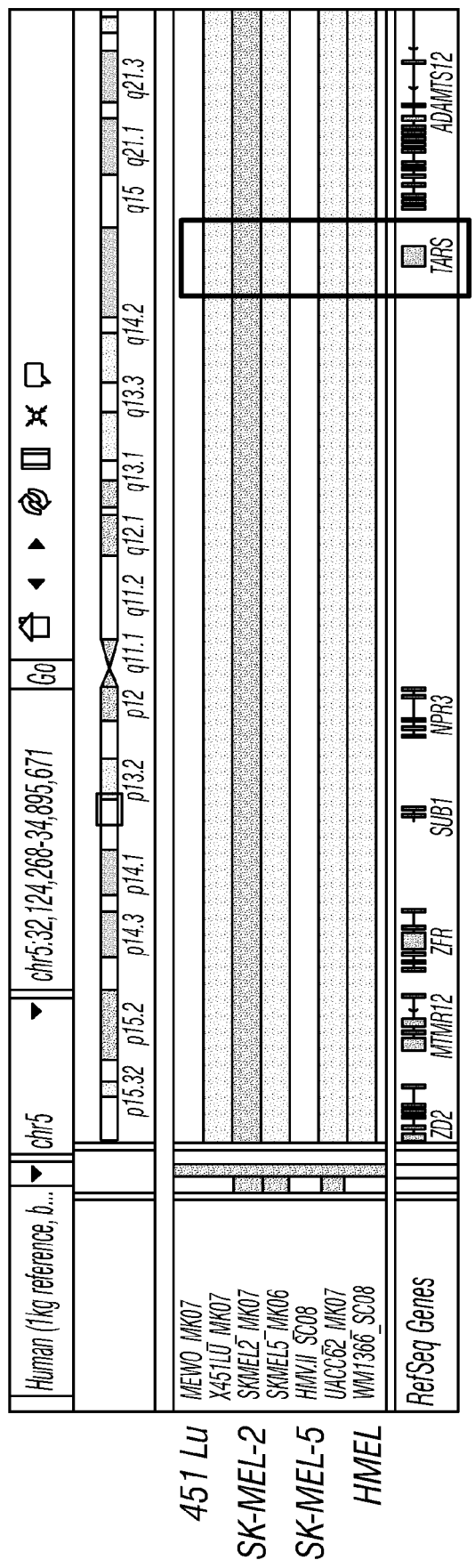

FIGS. 19A-C: Genomic copy number correlates with expression of TARS. c Genomic copy number data retrieved from the Sanger COSMIC website (a) and confirmed by expereimental studies (c), showing heterozygous deletion of TARS in the SK-MEL-2 cell line. The numbers in (a) indicate DNA copy number. b, DNA copy number correlates with mRNA expression of TARS. Black box indicates the SK-MEL-2 cell line.

Figure 20A:
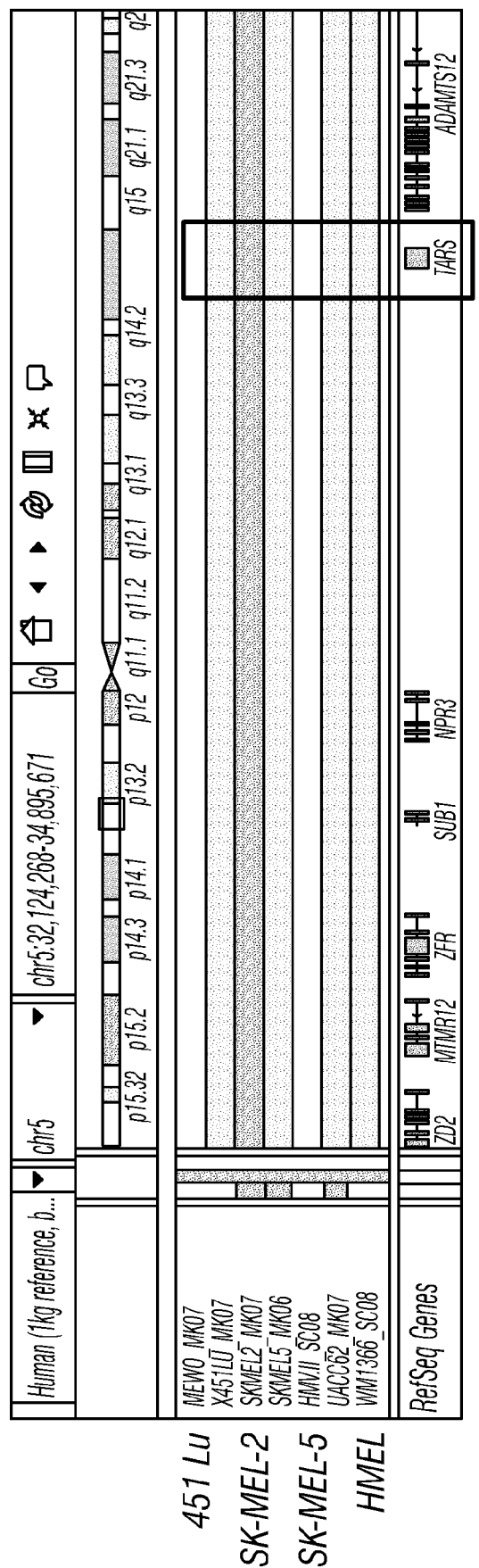
Figure 20B:
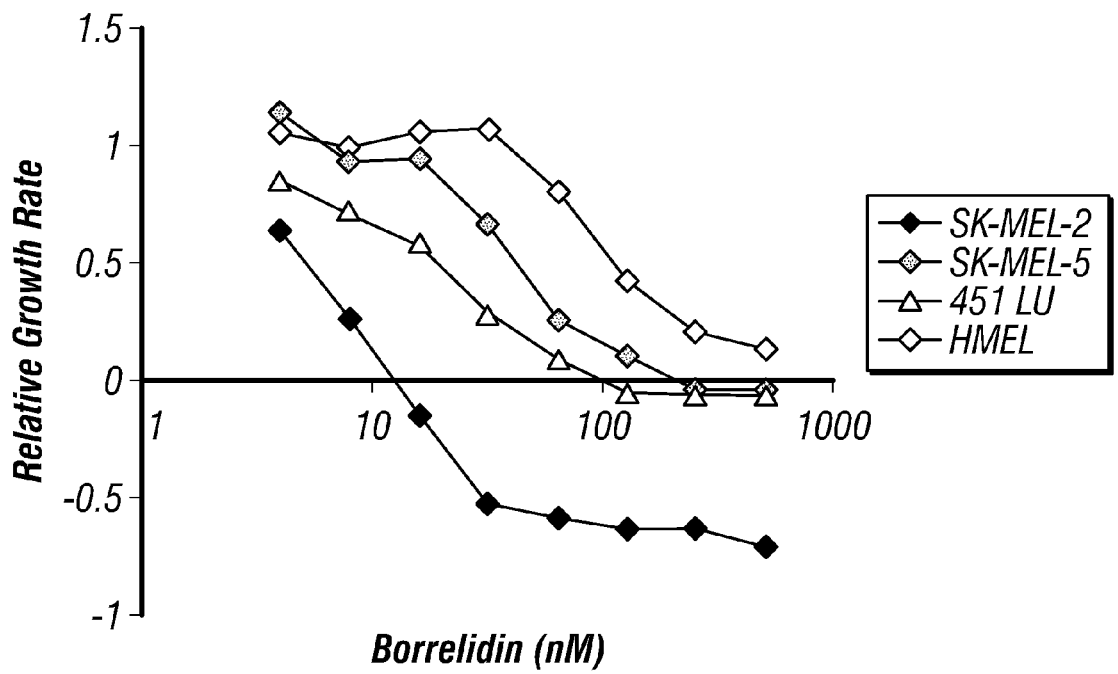
Figure 20C:
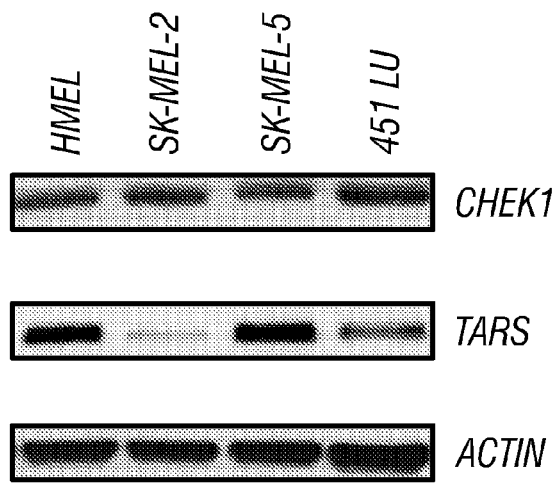

FIGS. 20A-C: Increased sensitivity to the TARS inhibitor Borrelidin in TARS deficient melanoma cells. a, The SK-MEL-2 cell line was identified as having a heterozygous deletion for TARS; the 451 Lu cell line was identified as being deficient for TARS; and the SK-MEL-5 and HMEL cell lines were identified as being wild-type for the TARS-gene (Data retrieved from the CCLE-Broad website). b, Borrelidin treatment had minimal effect on the growth of HMEL and SK-MEL-5 cells at low concentrations. In contrast, low concentrations of Borrelidin stalled the growth of SK-MEL-2 cells. 451 Lu cells showed intermediate sensitivity to Borrelidin treatment. c, The expression level of TARS was confirmed by western blotting, showing a strong correlation with the sensitivity to borrelidin.

Figure 21:
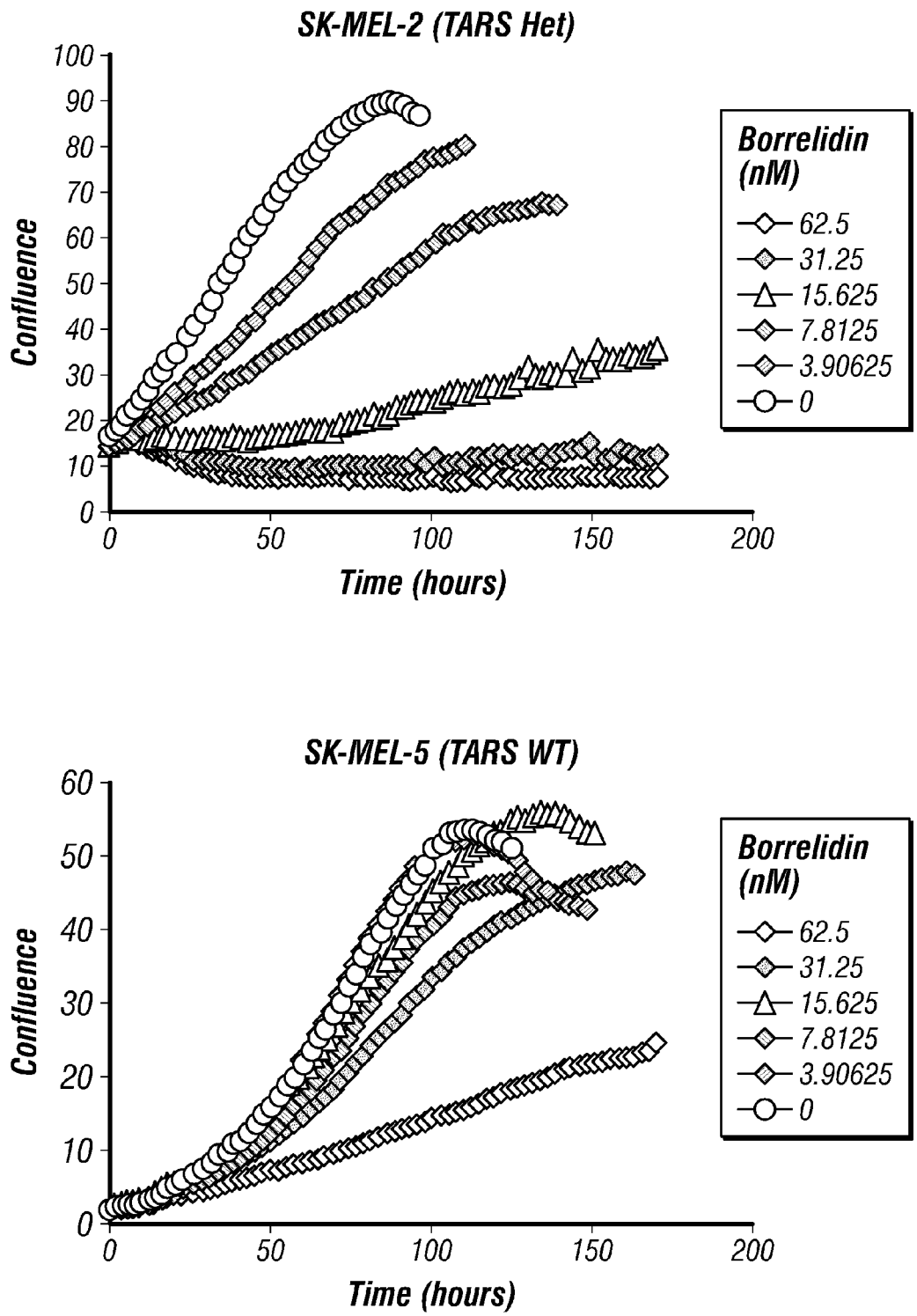
Figure 21:
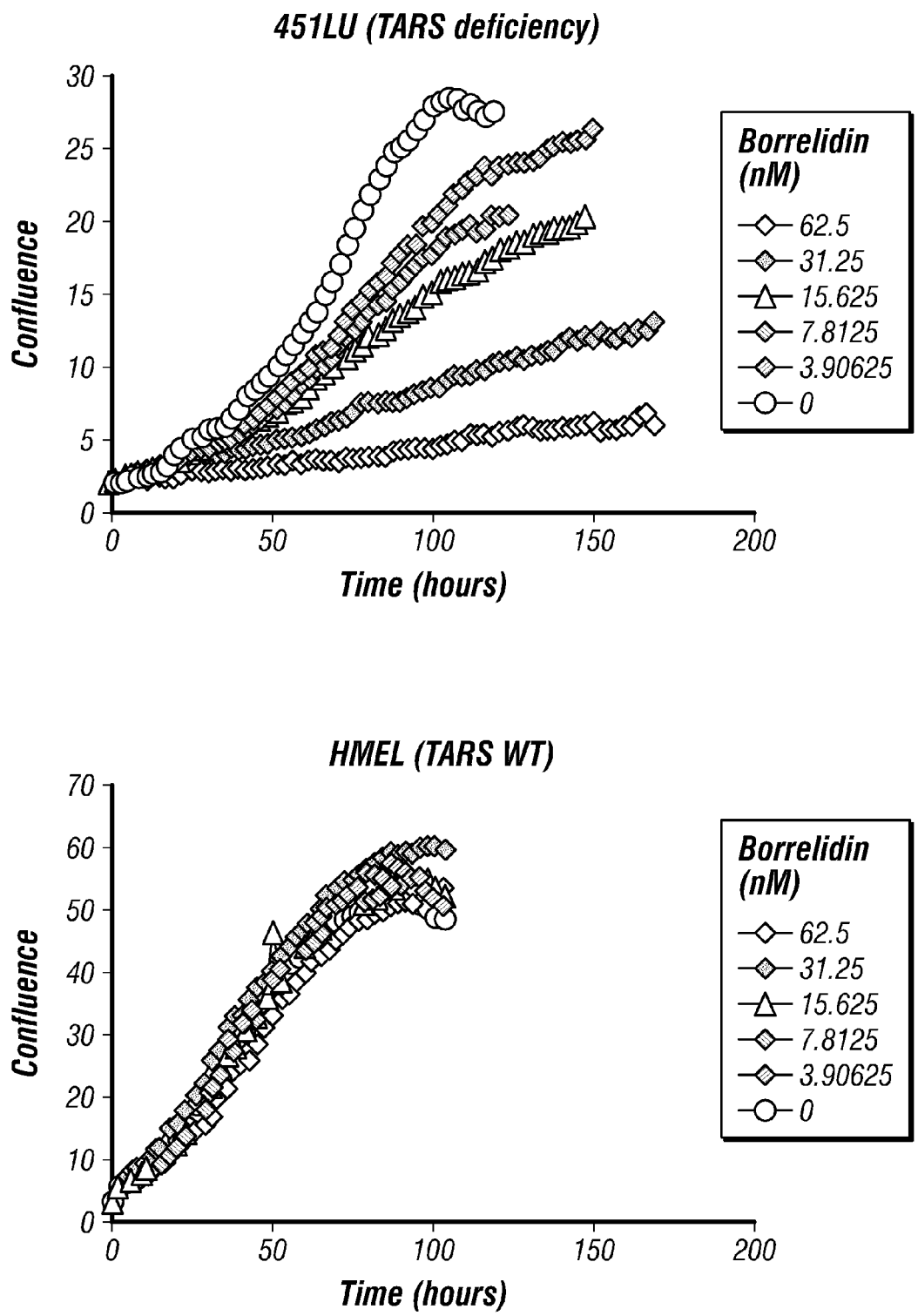

FIG. 21: Live growth curves (low initial cell density for SK-MEL-2) showing increased sensitivity to the TARS inhibitor Borrelidin in TARS deficient melanoma cells. SK-MEL-2 (TARS Het); SK-MEL-5 (TARS WT); 451 Lu (TARS deficient); HMEL (TARS WT).

Figure 22:
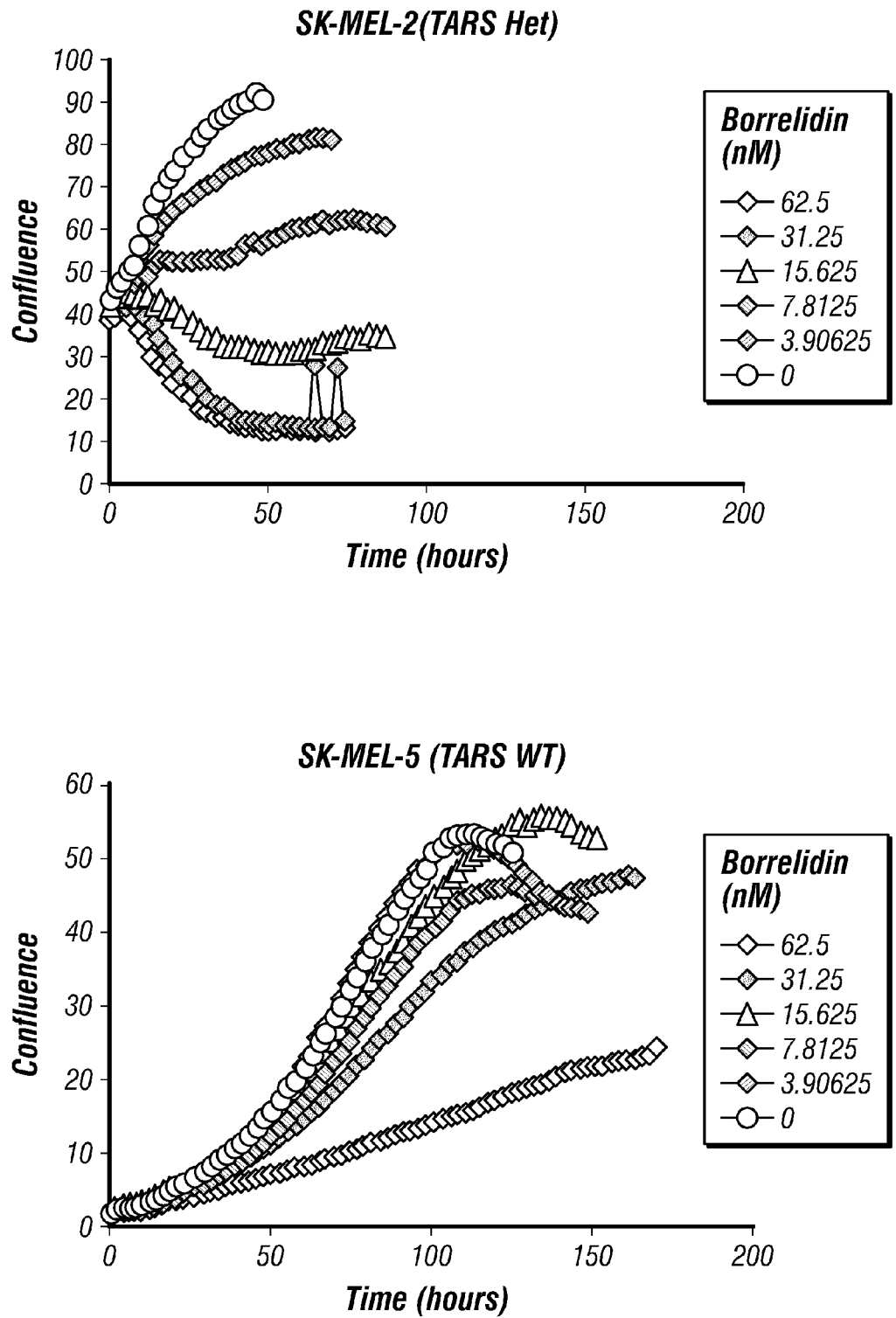
Figure 22:
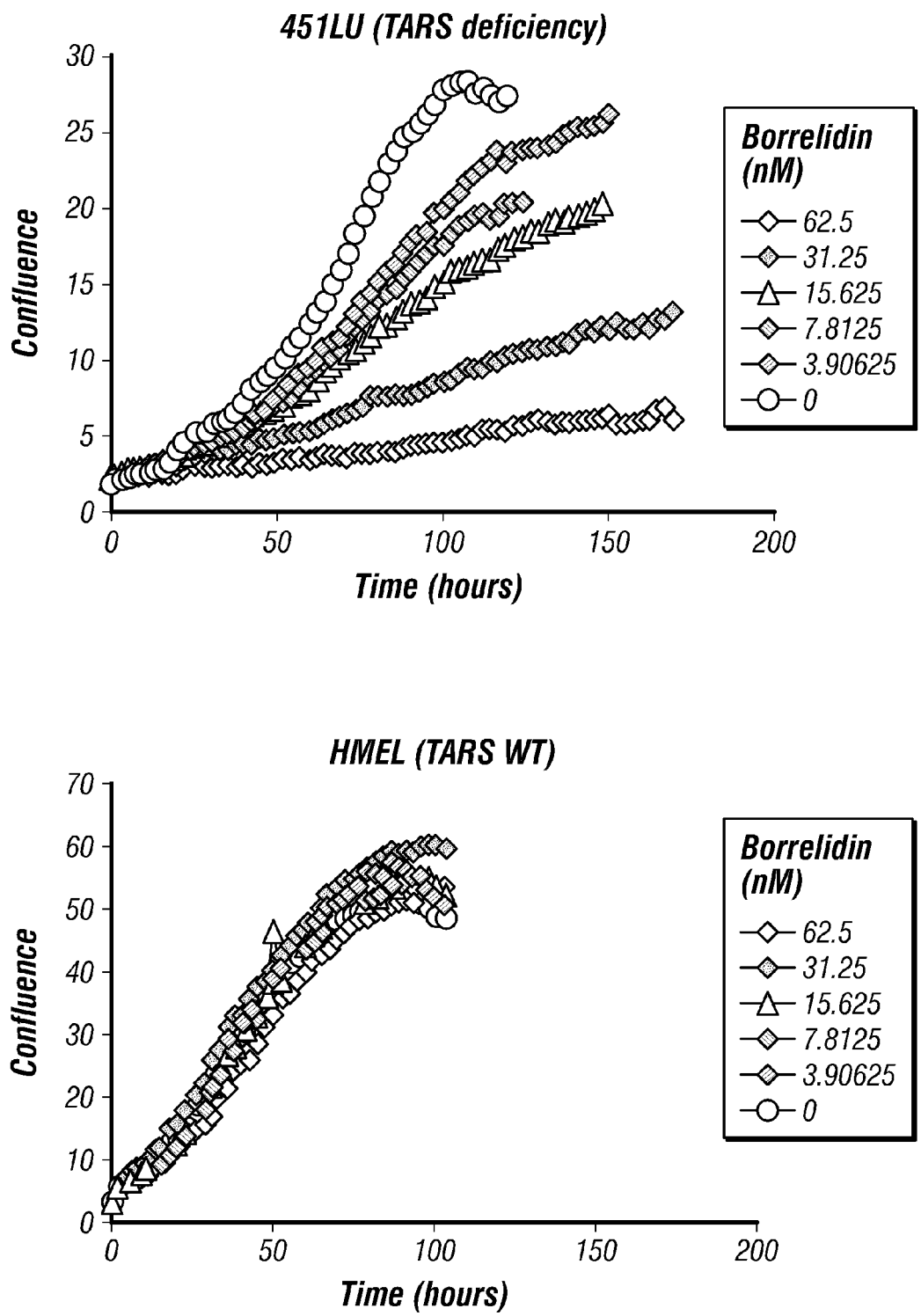

FIG. 22: Live growth curves (high initial cell density for SK-MEL-2) showing increased cytotoxicity of Borrelidin in TARS deficient melanoma cells. SK-MEL-2 (TARS Het); SK-MEL-5 (TARS WT); 451 Lu (TARS deficient); HMEL (TARS WT).

FIGS. 23A-D: Increased sensitivity to Borrelidin is reversed by ectopic overexpression of TARS in TARS deficient melanoma cells. a, b, Ectopic expression of TARS but not GFP or CHEK1 prevents the toxic effects caused by Borrelidin in SK-MEL-2 cells. a, A pCMV lentiviral construct expressing GFP was used to infect SK-MEL-2 cells. b, A pCMV lentiviral construct expressing TARS was used to infect SK-MEL-2 cells. c, The sensitivity of SK-MEL-2 cells to Borrelidin was reversed by ectopic expression of TARS but not GFP or CHEK1. d, Western blot showing that infection with a pCMV lentiviral construct containing TARS yielded high levels of TARS expression in SK-MEL-2 cells.

Figure 24A:
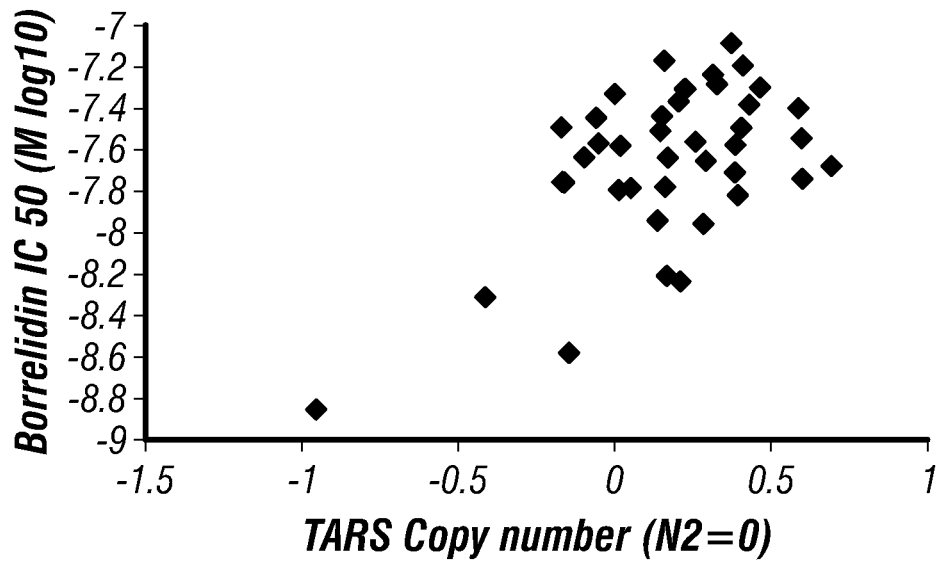
Figure 24B:
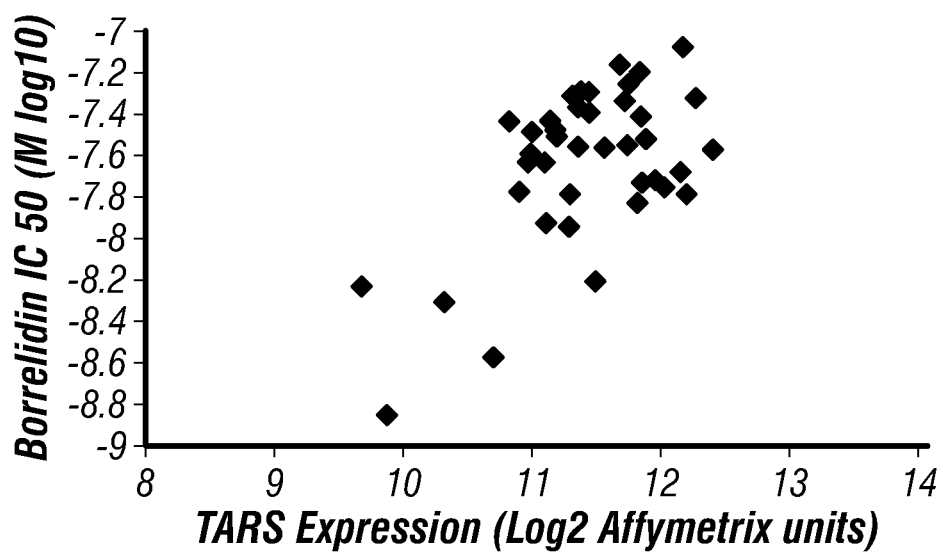
Figure 24C:
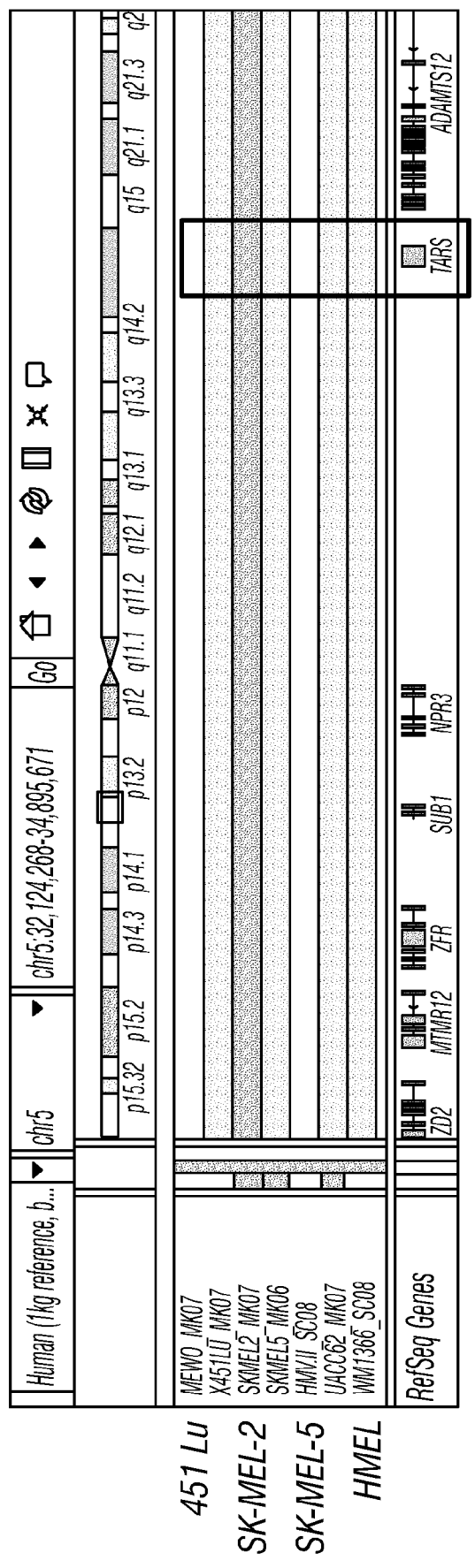
Figure 25A:
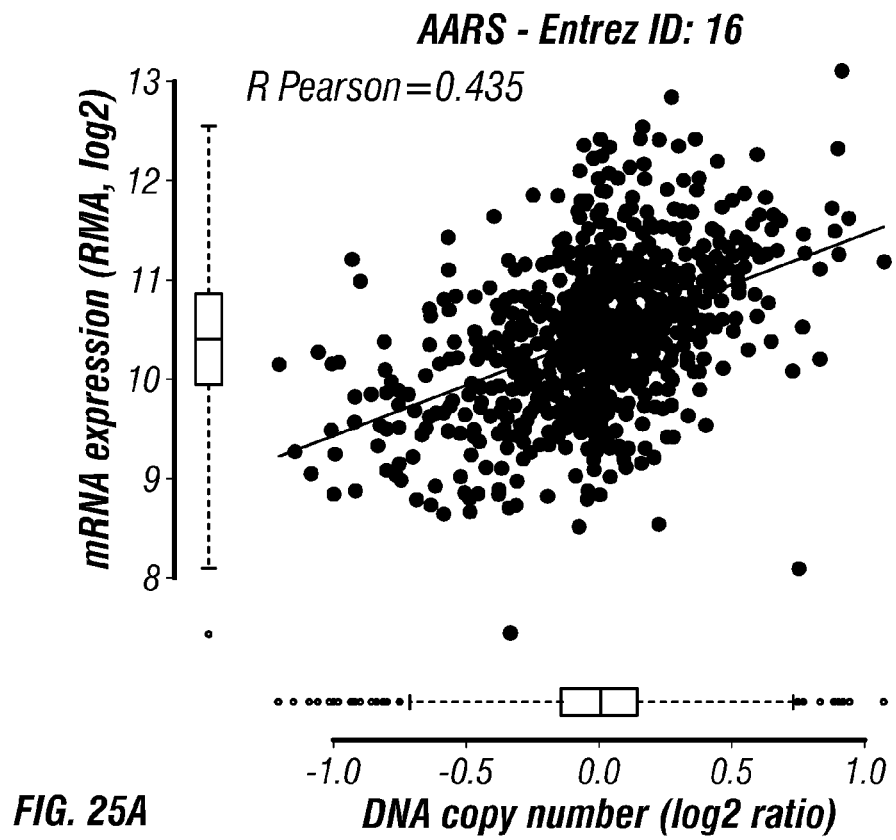
Figure 25B:
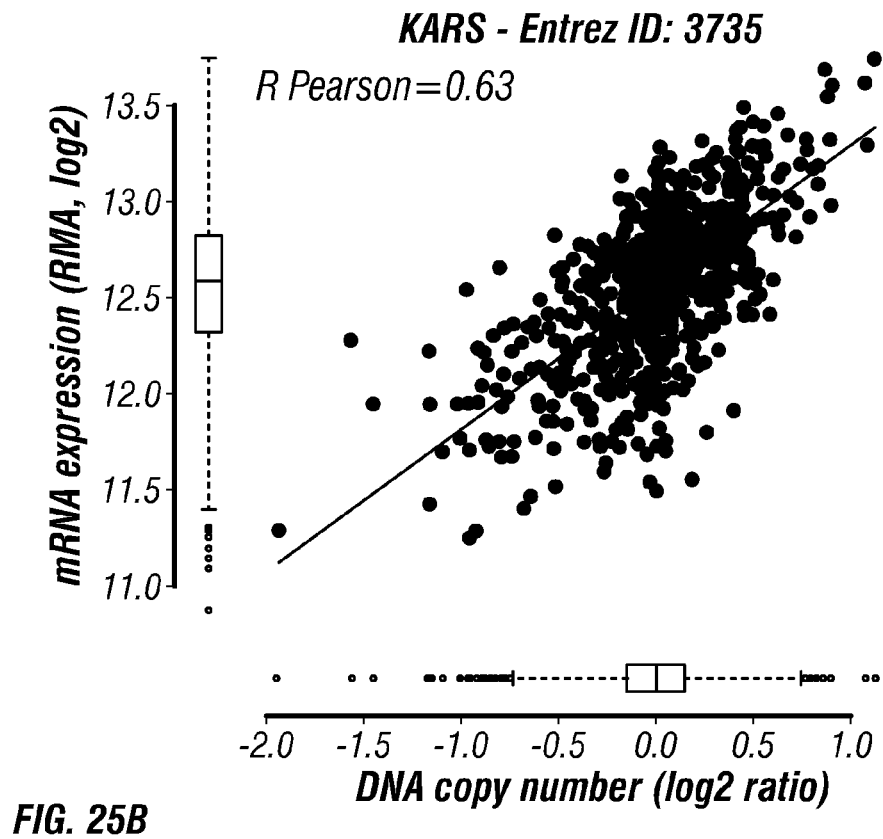
Figure 25C:
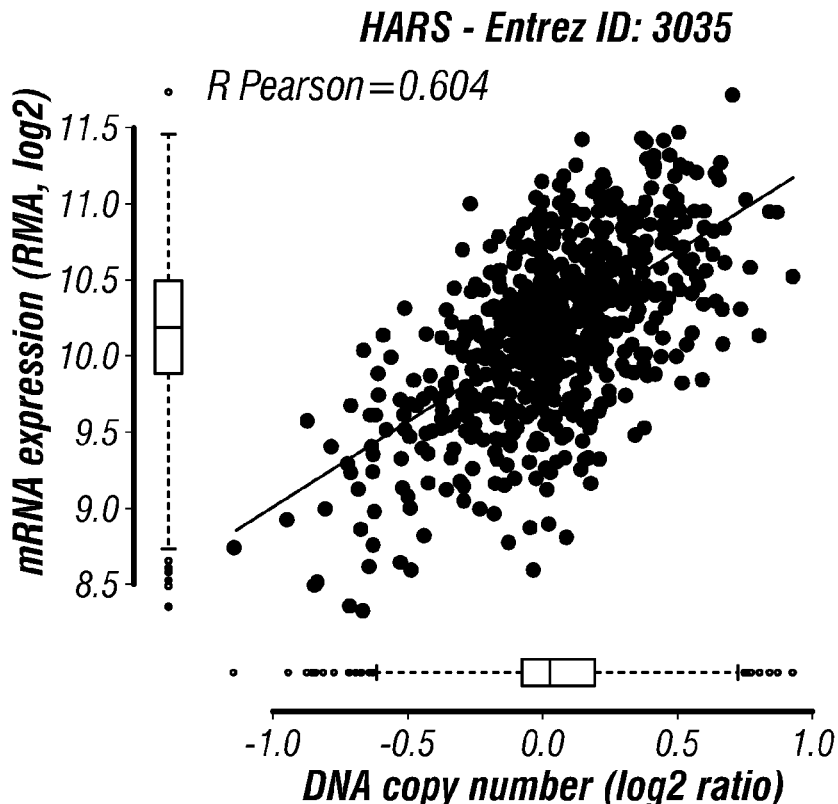
Figure 25D:
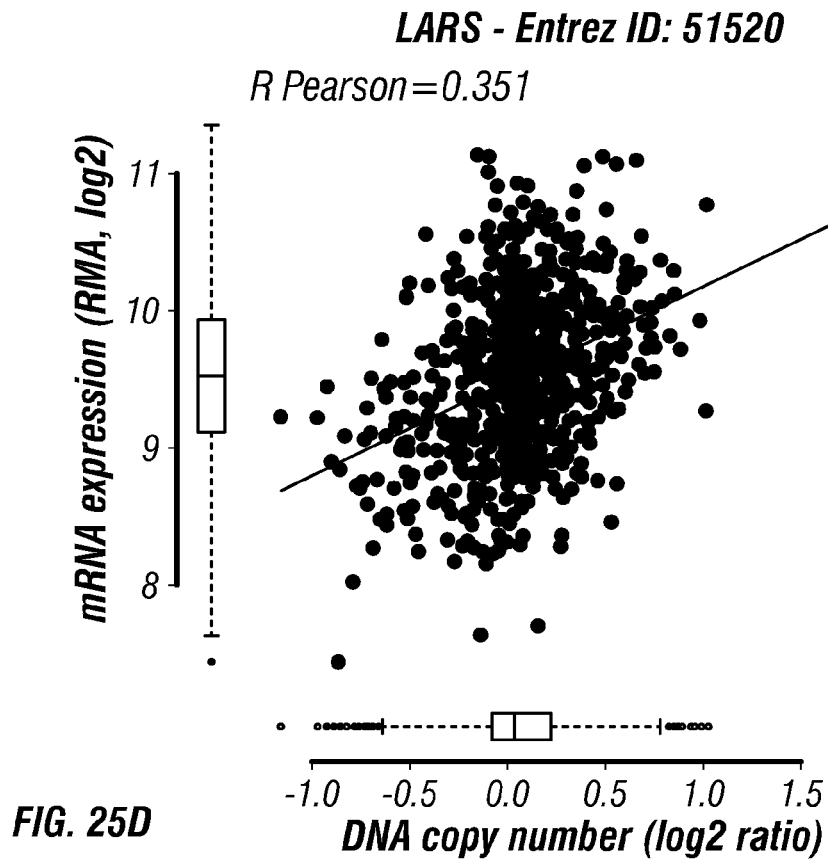

FIGS. 24A-C: Strong correlation between TARS copy number/mRNA expression with sensitivity to Borrelidin. Sensitivity to borrelidin ($IC_{50}$, in $\log_{10}$ M, y-axis) of a panel of cancer cell lines was taken from the NCI-60 database and was plotted as a function of TARS genomic copy number (A, x-axis) or mRNA expression (B, x-axis) obtained from the CCLE-Broad dataset. The SK-MEL-2 cell line (dark shading) has the lowest copy number and second low expression of TARS mRNA, and concordingly, the lowest $IC_{50}$ (greatest sensitivity) to borrelidin. Copy number based on addymetrix aCGH data generated experimental studies confirms copy number loss of TARS in SK-MEL-2 (C)

FIGS. 25A-D: Genomic copy number correlates with expression level for a wide range of ARS genes. Graphs show that DNA copy number correlates with mRNA expression of AARS (a), KARS (b), HARS (c) and LARS (d).

FIGS. 26A-D: CHEK1 protein expression does not correlate with genomic copy number and overexpression of CHEK1 does not confer resistance to the CHEK1 inhibitor, AZD7762. A, Genomic copy number from COMIC (Sanger Center) shows that CHEK1 (boxed) on chromosome 11 has only one copy in the cell line SK-MEL-2. B, Microarray expression and array CGH copy number data show a good correlation between mRNA levels and genomic copy of CHEK1 in ~900 cell lines (SK-MEL-2 is indicated by the box). C, However, SK-MEL-2 cells do not express lower levels of CHEK1 protein by western blot. D, Overexpression of CHEK1 in SK-MEL-2 cells does not confer resistance to AZD7762, a CHEK1 inhibitor.

DESCRIPTION OF ILLUSTRATIVE EMBODIMENTS

I. The Present Invention

Deletion (e.g., heterozygous deletion) of large regions of the genome is a prototypic somatic event in cancer, which drives tumorigenesis by ablating the function of critical tumor suppressor genes. These deletions often encompass neighboring genes with no known role in cancer pathogenesis which in many instances include essential genes encoding essential metabolic enzymes. However, the loss of a portion of enzymatic activity (e.g., a 50% loss) in tumor cells is typically tolerated even in the case of essential, housekeeping genes. One reason for this is because most metabolic enzymes are present in vast excess and toxicity is dependent upon loss of expression below a critical threshold. Typically far greater than a 50% loss in activity is required to have any effect on the cancer cells.

Studies presented here demonstrate that heterozygous inactivation of one copy of the ENO1 gene renders cancer cells exquisitely sensitive to glycolysis pathway inhibitors.

Figure 3A:
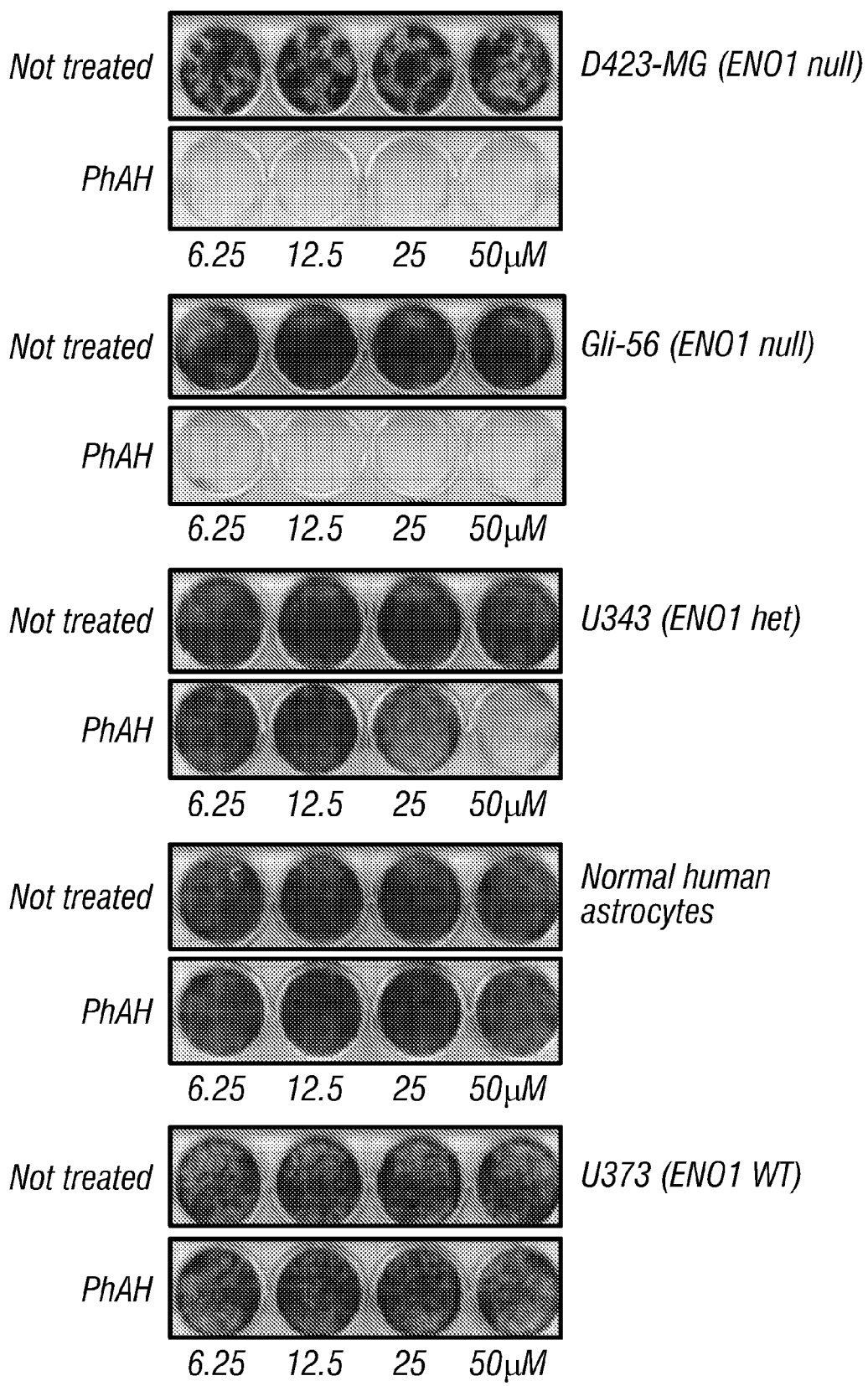
FIGS. 3A-D: Extreme sensitivity of ENO1-null cells to the pan-enolase inhibitor PhAH. a, Crystal violet stained plates of cell lines after treatment with varying concentrations of PhAH showing acute toxicity to D423-MG and Gli56 ENO1-null but to none of ENO1 WT cell lines and normal astrocytes. b, The sensitivity of GBM lines to PhAH treatment broadly correlated with their overall enolase activity. Pre-incubation of the lysates with 1 µM PhAH inhibited enolase enzymatic activity by >95%. c, PhAH treatment had minimal effect on the growth of ENO1 WT GBM cells and normal astrocytes except at concentrations higher than 50 µM. In contrast, even low concentrations of PhAH are sufficient to stall the growth of ENO1-null cells. ENO1 heterozygous cells (D502-MG and U343) showed intermediate sensitivity to PhAH treatment. d, shows a representative view image of crystal violet stained plates of additional GBM cell lines and normal astrocytes in the absence (on the left) or presence of PhAH (25 µM, on the right) after 15 days in culture.
Figure 11:
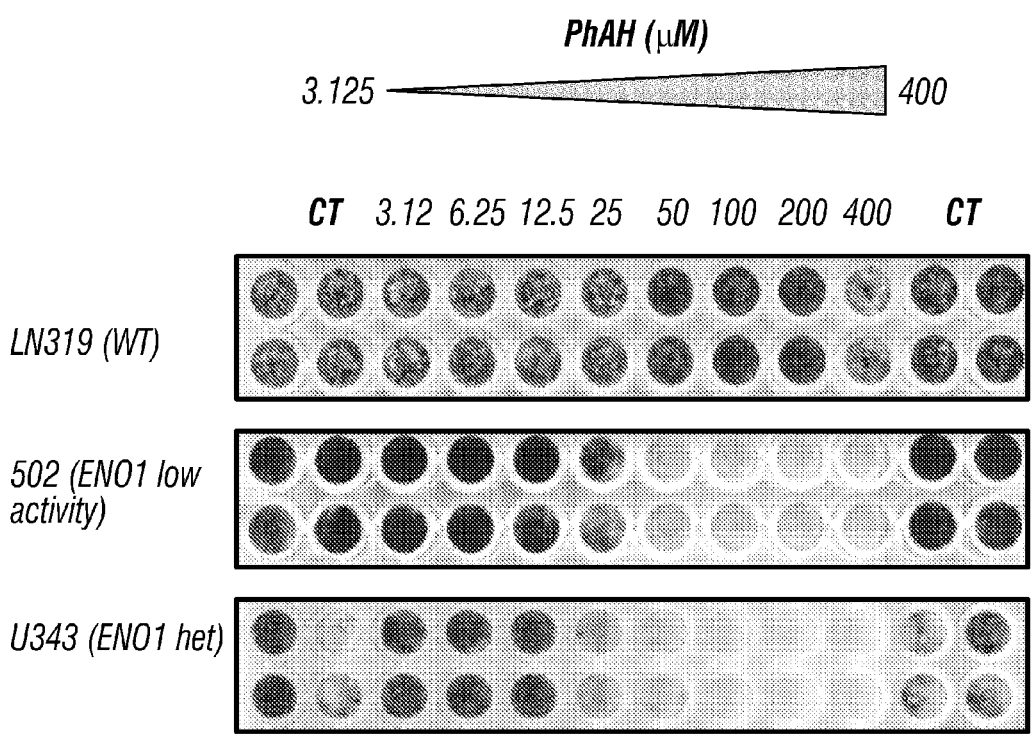
FIG. 11: Sensitivity of ENO1 heterozygous cells to the pan-enolase inhibitor PhAH. Crystal violet stained plates of WT (LN319) or ENO1 heterozygous (502 or U343) cell lines after treatment with increasing concentrations of PhAH. Even low concentrations of PhAH are sufficient to inhibit the growth of ENO1 heterozygous cells (D502-MG and U343).
Figure 12A:
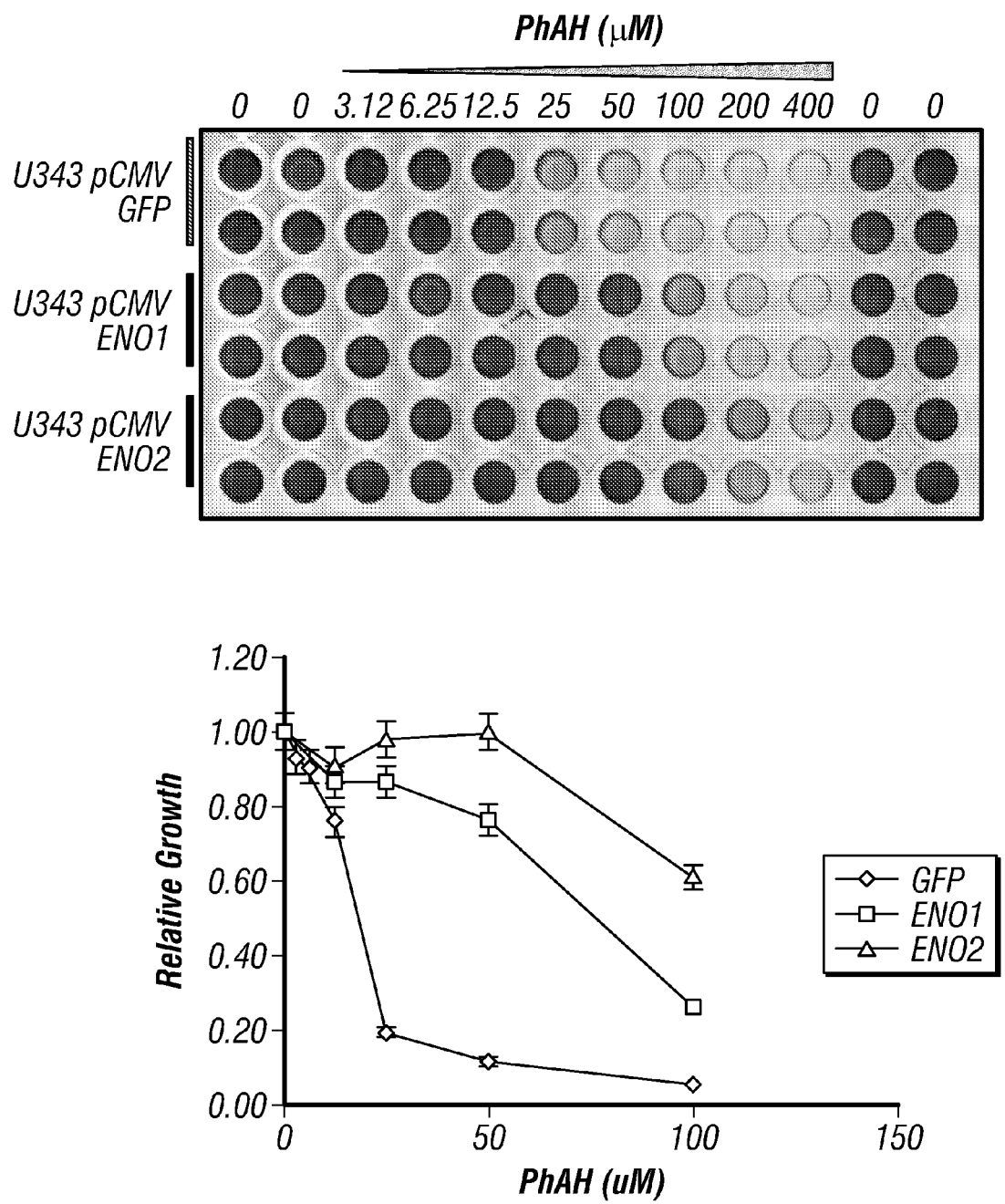
FIGS. 12A-B: Sensitivity of U343 cells to PhAH is due to reduced ENO1 expression. a, sensitivity of ENO1 heterozygous cells (U343) to PhAH was partially reversible by ectopic ENO1 or ENO2 expression. b, The sensitivity of ENO1 heterozygous cells (U343) to PhAH was enhanced in presence of the ATP synthase inhibitor oligomycin (10 nM). While oligomycin on its own had minimal effects, the combination with PhAH was highly toxic to U343 cells. Again, this effect was largely reversed by complementation with ectopic ENO1 or ENO2 expression.
Figure 12B:
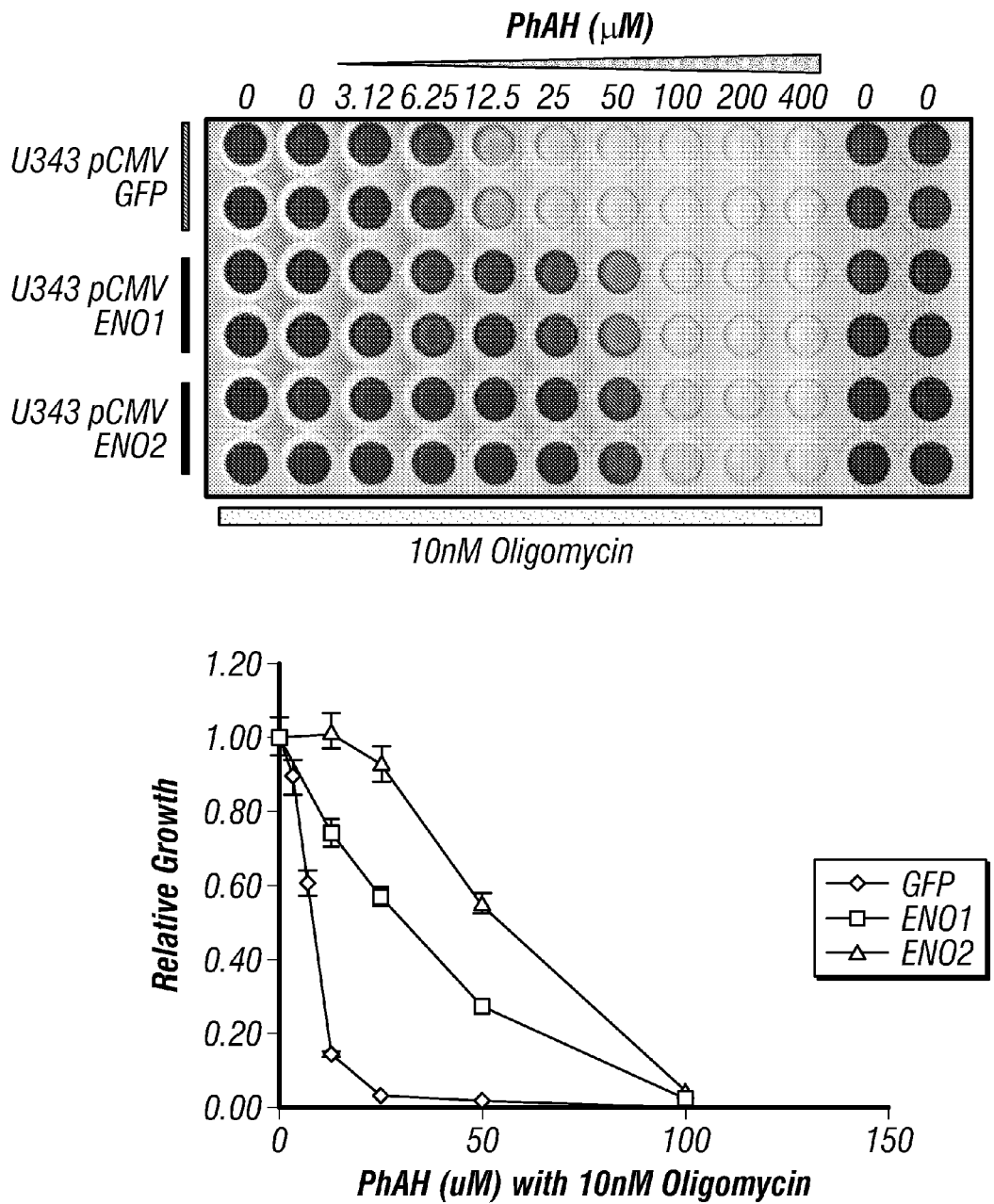
Figure 13A:
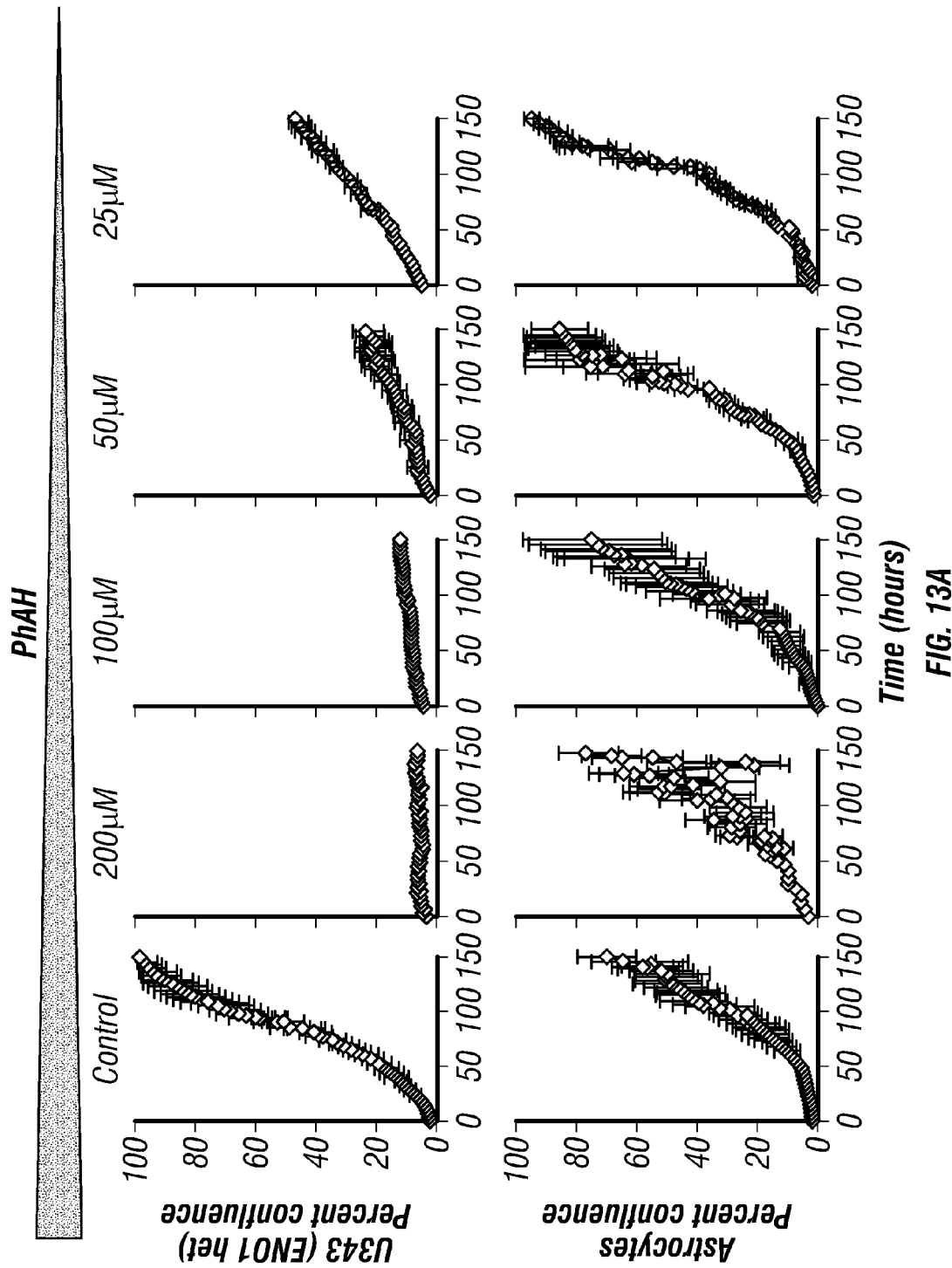
FIGS. 13a-b: Increased sensitivity of U343 cells to PhAH with or without oligomycin compared to normal human astrocytes. U343 ENO1 heterozygous cells require about 8-times lower doses of PhAH to achieve similar growth inhibition as compared to normal human astrocytes, (a) growth curves of normal human astrocytes and U343 cells in response to increasing doses of PhAH, and (b) in combination with the mitochondrial electron transfer chain inhibition, oligomycin (2.5 nM).
Figure 13A:
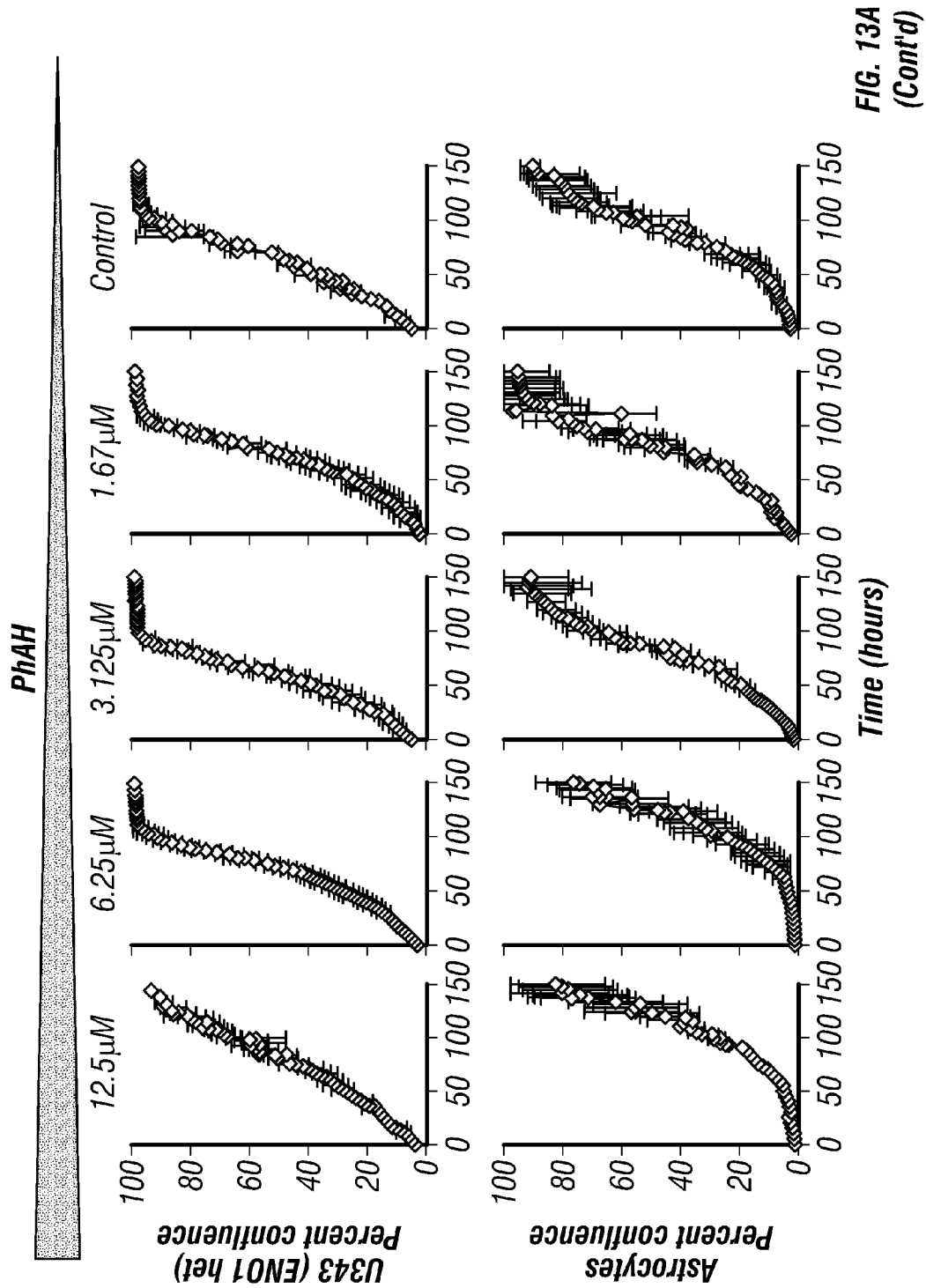
Figure 13B:
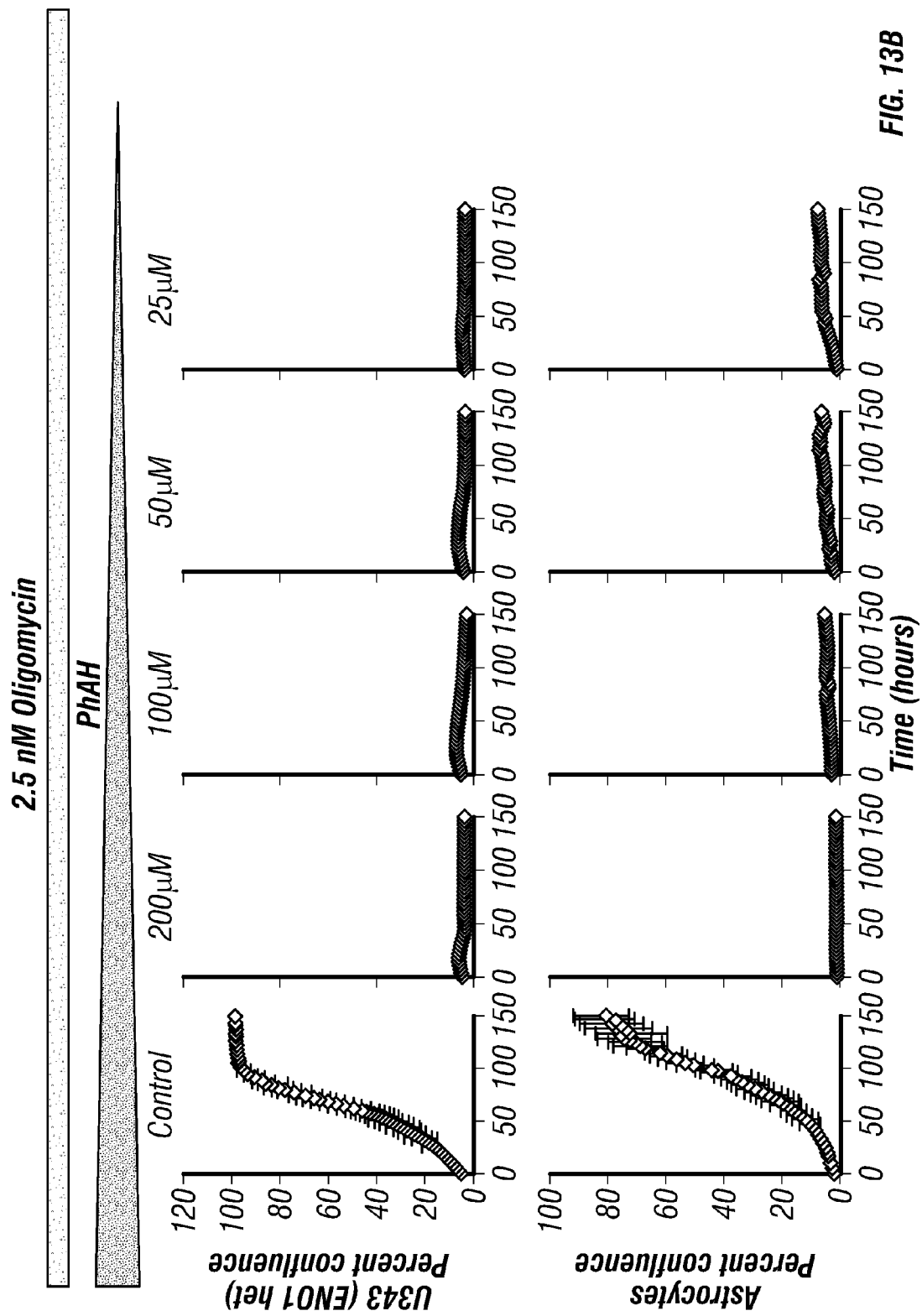
Figure 13B:
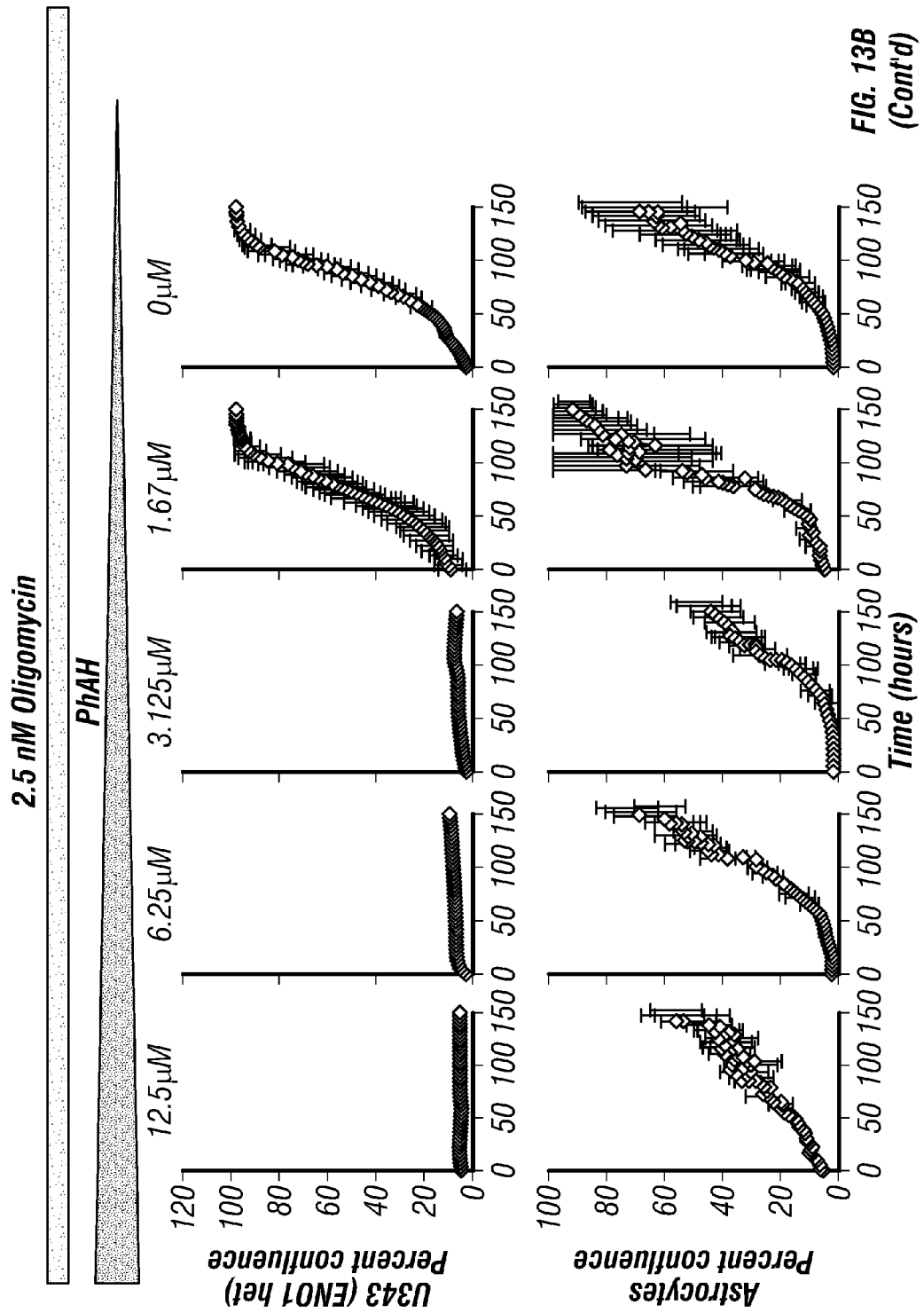

Conversely, in cancer cells that retain both copies of ENO1 very high levels of glycolysis inhibitors are need to have any effect on cancer cell growth. Thus, cancer cells with a heterozygous ENO1 inactivation can be effectively treated with far lower concentrations of glycolysis inhibitors than would otherwise be required. For example, glioblastoma cells showing heterozygous deletion of ENO1 (U343 and D502-MG), are 2-8 fold more sensitive to the enolase inhibitor, Phosphoacetohydroxamate (PhAH) as compared to ENO1-WT glioblastoma cell lines and normal human astrocytes (see, FIG. 3b-c and FIG. 11). This effect was at least partially reversible by complementing the cells with a vector for expression of ENO1 or ENO2, demonstrating that the effect is due the reduced level of enolase expression in the cancer cells. Importantly, the sensitivity of cells to PhAH could be further enhanced by co treatment with oligomycin (FIG. 12).

In view of these studies, heterozygous inactivation of housekeeping genes such as ARS, PDG or ENO1 can serve as biomarker for guiding anticancer therapy. For example, a cancer patient determined to have such a heterozygous deletion of ENO1 could be treated with a glycolysis inhibitor (e.g., an enolase inhibitor) or a prodrug of such an inhibitor. Likewise patients determined to have such a heterozygous deletion of an ARS gene could be treated with a an ARS inhibitor. Preferably, these patients are treated in conjunction with a second therapy (e.g., a second glycolysis inhibitor or a mitochondrial transport inhibitor in the case of ENO1 or a protein synthesis inhibitor in the case of ARS) thereby further enhancing the efficacy of the specific inhibitor upon the cancer cells. Likewise, cancer cells from a patient can be analyzed for a heterozygous inactivation of ENO1 or ARS to predict whether the patient is likely to respond to a specific inhibitor therapy or even to estimate the dosage of the therapy that should be applied. These methods allow anticancer therapy to be tailored to particular patient and the particular cancer in that patient. Accordingly, the therapy should not only prove more effective, but side effects can be significantly reduced by identifying the therapies that will be effective rather than merely applying "standard" treatment with many side effects and untested efficacy.

Embodiments of the present invention exploit the genetically determined metabolic differences between normal and cancerous tissue to generate cancer cell specific treatment. Specifically, aspects of the invention are based in part upon the surprising discovery that the homozygous deletion of redundant essential housekeeping genes create cancer-specific vulnerabilities. Complete loss of activity of proteins encoded by these genes and cell death is obtained by administering a selective inhibitor for the non-deleted homolog or a compound targeting both homologs at doses that discriminate between deleted and non-deleted tissues. Using this method, the health of normal cells where both genes are intact and expressed is not effected.

Figure 16A:
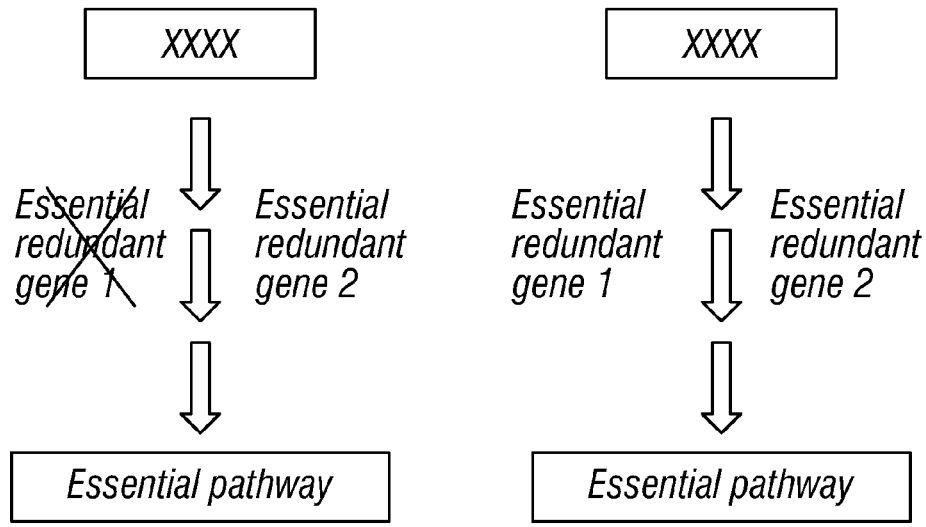
FIGS. 16A-D: Homozygous deletions in essential metabolic/housekeeping genes sensitize tumors to molecular targeting of redundant homologues. Many essential metabolic processes are executed by redundant genes, such that incidental homozygous deletion during tumor development of one member causes minimal disruption to the system (Panel a). Nevertheless, if the second redundant homologue is targeted by a specific inhibitor, the essential metabolic process is compromised in the tumor with the deletion, but the normal genetically intact tissue is not affected because the tumor-specifically deleted homologue is still functional (Panel b). A specific example of this general concept is the case of ENO1 homozygous deletion in glioblastoma. ENO1 homozygous deletion is tolerable to the tumor because ENO2 is still expressed (Panel c), however a specific inhibitor of ENO2 should completely abrogate enolase activity in ENO1 null tumor cells (hence blocking glycolysis and ATP synthesis) but leave genomically intact normal tissues unaffected (Panel d).

Cancer genomes are characterized by numerous amplifications and deletions targeting driver oncogenes and tumor suppressor genes, respectively. These copy number alterations targeting cancer genes nearly always involve changes in the copy number of neighboring genes that have no direct role in oncogenic process. Here, these collateral events are exploited in a strategy designed to assess potential unique vulnerabilities in cancer cells that have incurred homozygous deletion of essential housekeeping genes. A large body of genetic interaction studies in invertebrates as well as mice indicates that many essential cellular housekeeping functions are carried out by multiple homologous genes encoding overlapping function that enables cell viability in the face of loss of one homologue but complete lethality upon loss of multiple homologues (see, e.g., FIG. 16 and Deutscher et al., 2006; DeLuna et al., 2008; Costanzo et al., 2010; Vavouri et al., 2008; and Brookfield et al., 1997, each of which is incorporated herein by reference). On this conceptual framework, it was envisioned that the homozygous deletion of redundant essential housekeeping genes could create cancer-specific vulnerabilities whereby pharmacological inactivation of the second non-deleted homologue would result in complete loss of activity in tumor cells carrying the deletion, but not compromise the health of normal cells where both genes are intact and expressed (FIG. 16a). To search for such genes, the high-resolution comprehensive TCGA dataset of GBM was examined (Table 1 and The Cancer Genome Atlas Research Network 2008).

Figure 1A:
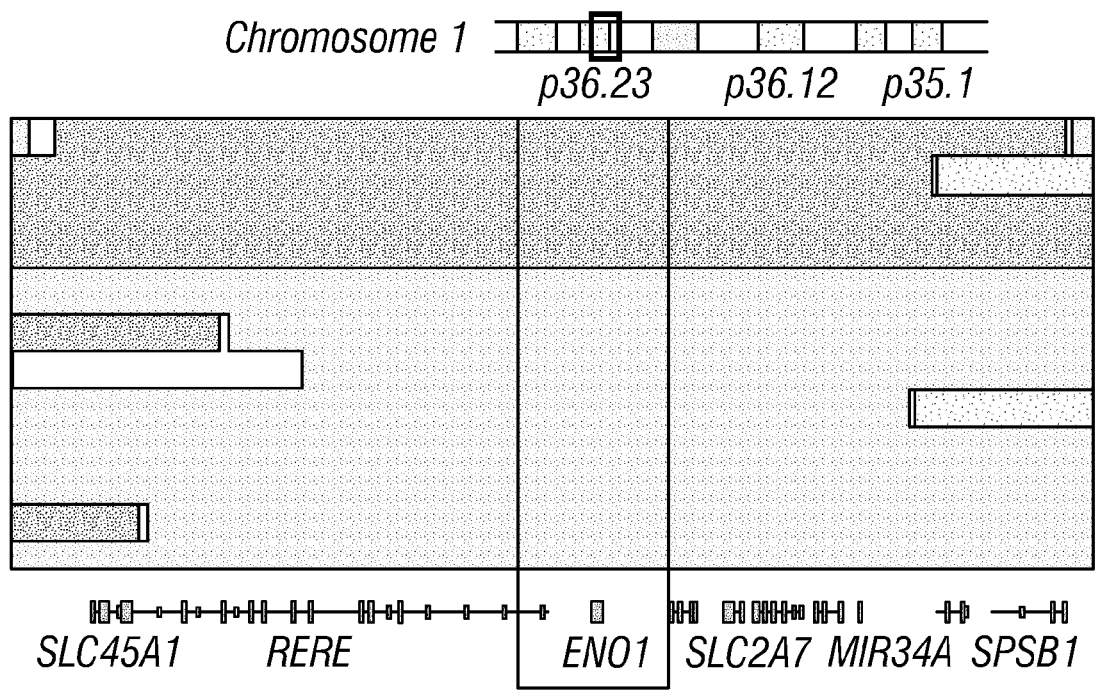
Figure 16B:
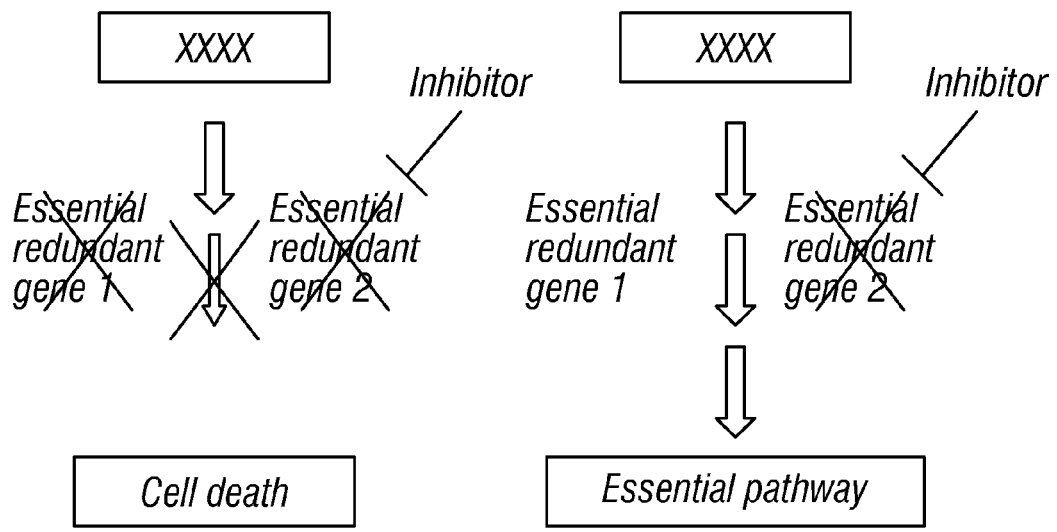
Figure 16C:
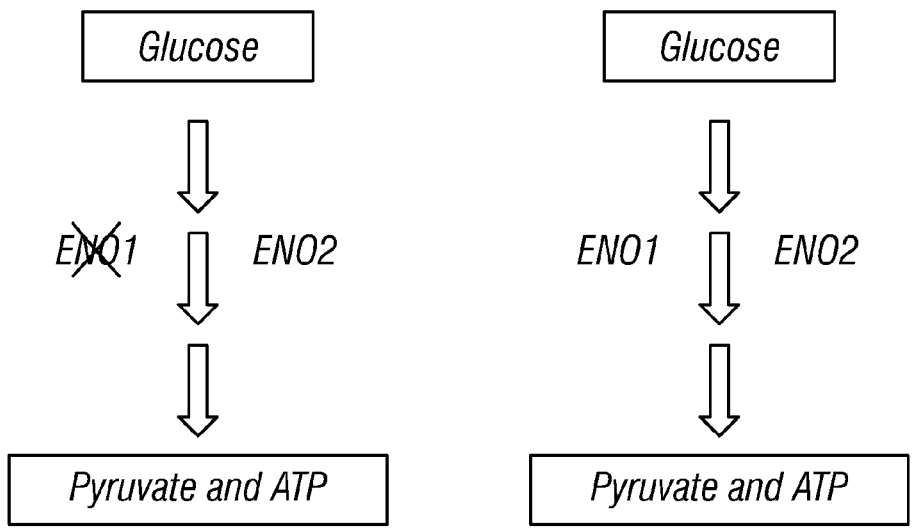
Figure 16D:
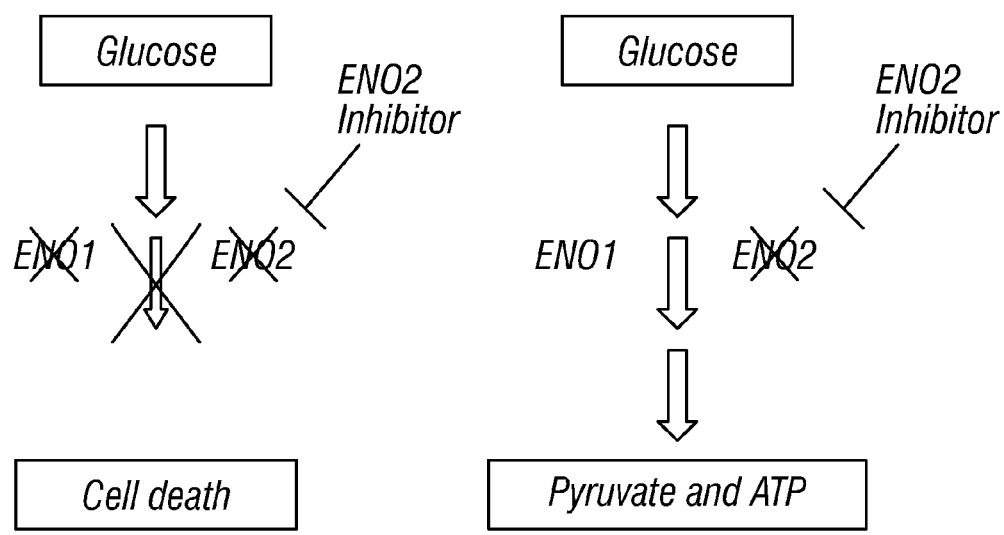

Genetic and pharmacologic proof of concept of the "collateral-vulnerability" approach is presented herein with the ENO1 gene which resides at the 1p36 locus, a region subject to frequent deletion in GBMa with several candidate tumor suppressor genes including CHD5 and CAMTA1 (FIG. 1a; Henrich et al., 2011 and Bagchi et al. 2008). The 1p36 locus is homozygously deleted in 1-5% of GBMs (as well as oligodendrogliomas and large cell neuroendocrine lung tumors, see e.g., The Cancer Genome Atlas Research Network 2008; Yin et al., 2009; Duncan et al., 2010; Kotliarov et al., 2006; and Peng et al., 2005) and often involves homozygous deletion of the ENO1 gene. Enolase, encoded by three homologous genes, is an essential enzyme that catalyzes the second to last step of glycolysis, converting 2-phosphoglyceric acid into phosphoenolpyruvate (Poyner et al., 1992). In mammals, enolase activity is encoded by three genes, ENO1 which is ubiquitously expressed, ENO2 which is expressed exclusively in neural tissues, and ENO3 which is expressed in muscle tissues (Table 2). Thus, given the critical importance of glycolysis to energy generation in normal and especially tumor cells (Wise et al., 2010), GBM tumors homozygous null for ENO1 would be predicted to be highly sensitive to inhibition of enolase 2, while normal neuronal tissues would be rescued by the functional redundancy of enolase 1 (FIG. 16b). Correspondingly, Eno2 knockout mice are viable and fertile, suggesting that pharmacological inhibition of enolase 2 is likely to be well tolerated (Table 2). Moreover, *S. cerevisiae* which possesses several enolase-homologues shows weak phenotypes with single mutants and incurs cell lethality only when all homologues are deleted (Deutscher et al., 2006; DeLuna et al., 2008; and Costanzo et al., 2010). *C. elegans* and *Drosophila* possess only one gene encoding enolase activity and its deletion is lethal (Buszczak et al., 2007 and Sonnichsen et al., 2005).

The genetic and pharmacological results described herein demonstrate that, enolase 2 inhibition is lethal in cells with 1p36 homozygous deletion with collateral loss of ENO1, while ENO1 intact cells can rely on Enolase 1 to undergo glycolysis and support survival. Given that several homozygously deleted housekeeping genes can occur in the same "deleton" on 1p36 (e.g. H6PD, Table 1), it may be possible to further increase the effectiveness and cancer-cell specific killing by combining the inhibition of ENO2 with that of another homologue of simultaneously deleted housekeeping gene.

Figure 17:
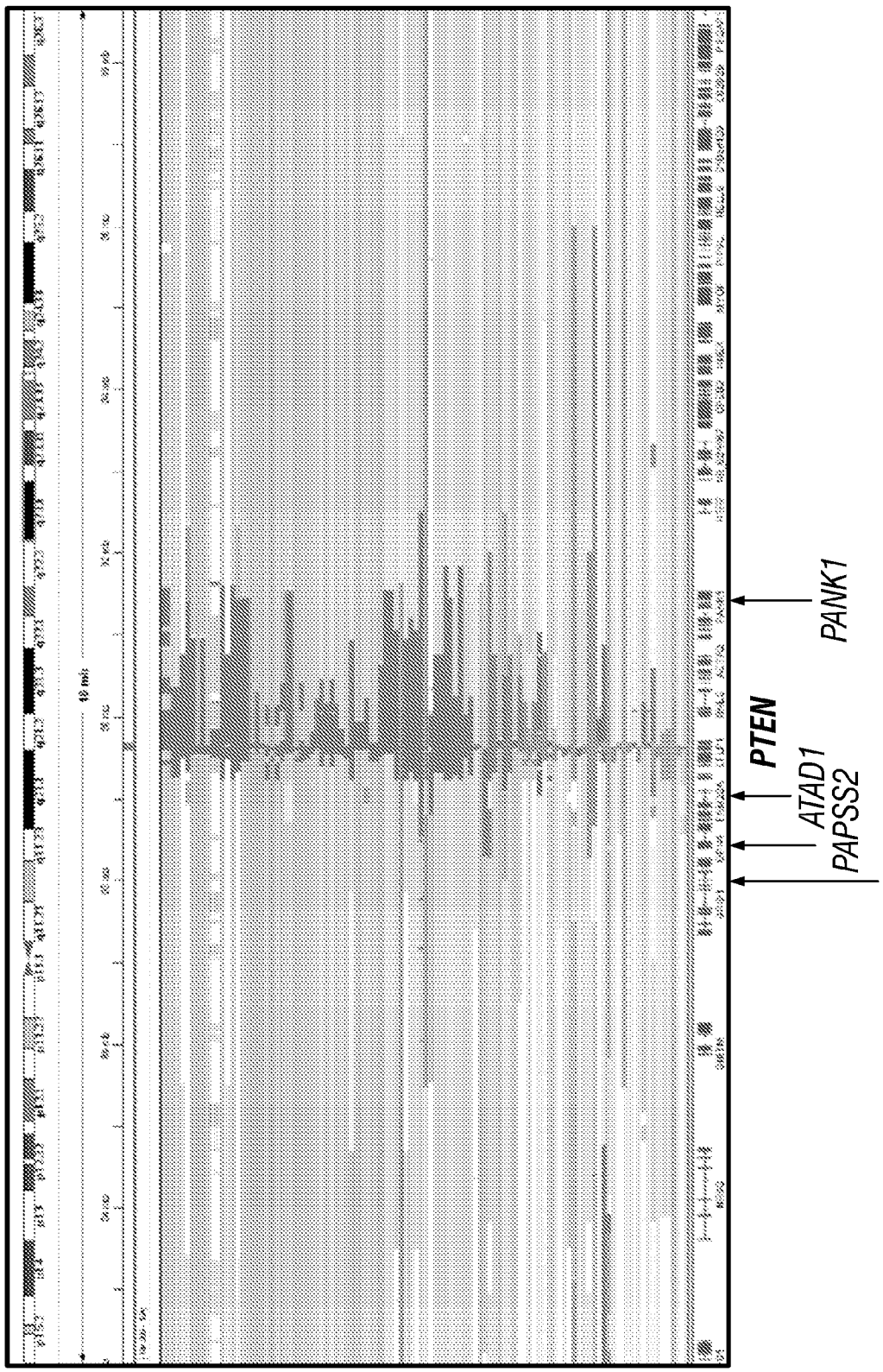
FIG. 17: Homozygous deletions targeting major tumor suppressors can include essential metabolic/housekeeping genes. Several loci, including 10q23 (PTEN) and 9p21

Indeed, collateral vulnerability may be expanded to other passenger-homozygously deleted housekeeping genes, besides ENO1. The major homozygously deleted loci in GBM, 9p21 (CDKN2A) and 10q23 (PTEN), encompass a significant number of deleted passenger genes that are members of functionally-redundant housekeeping gene families (Table 1, FIG. 17). Importantly, many of these compounds are completely novel molecular entities with regards to the treatment of cancer. By one estimate, 11% of all protein coding genes in the human genome are deleted in human cancers (Bignell et al., 2010). Thus, given the large number of homozygous deletions across many different cancers types spanning many hundreds of genes (Bignell et al., 2010; Taylor et al., 2010; Cox et al., 2005; and Tonon et al., 2005), the paradigm described here for GBM should be applicable to the development of personalized treatments of many additional cancer types.

Specific inhibitors of non-deleted homologs can be found either by chemical modifications of already available pan-enzymatic inhibitors (Table 3) or by high throughput screening using available small molecule libraries. Inhibition can be detected using specific activity assays for each enzyme. For example, for enolase this involves following NADH oxidation using a Pyruvate Kinase and LDH coupled assay. For H6PD this can be done by measuring NADPH production (Clarke et al., 2003, incorporated herein by reference). Aconitase activity can be measured by monitoring NAPD+ reduction in an isocitrate dehydrogenase coupled reaction (Bulteau et al., 2005, incorporated herein by reference). Panthotenate Kinase activity can be measured by incubating the enzyme with $^{14}C$ labeled panthotenate and quantifying the radioactive product by scintillation counting (Zheng et al., 2008, incorporated herein by reference). KIFactivity can be measured using an ATPase assay.

Tumors with homozygous deletions in essential metabolic housekeeping genes can be diagnosed post-surgery or biopsy using copy number analysis or enzymatic assays of the tumor tissue. In the case of enolase, for example, it is possible to run enolase 1 and 2 activity assays (Poyner et al., 1992) on tumor and normal tissues. Tumors that are appropriate therapeutic targets will be identified as having nearly undetectable enolase 1 activity with normal enolase 2 activity. This can be extended to other metabolic enzymes. For proteins that do not have such readily available enzymatic assays, copy number analysis of tumor samples can be used as a diagnostic approach. In our present studies we showed that for enolase 1 this is an effective way to detect true homozygous deletions, as samples that show homozygous deletions based on copy number also have nearly undetectable levels of enolase 1 expression.

Figure 14A:
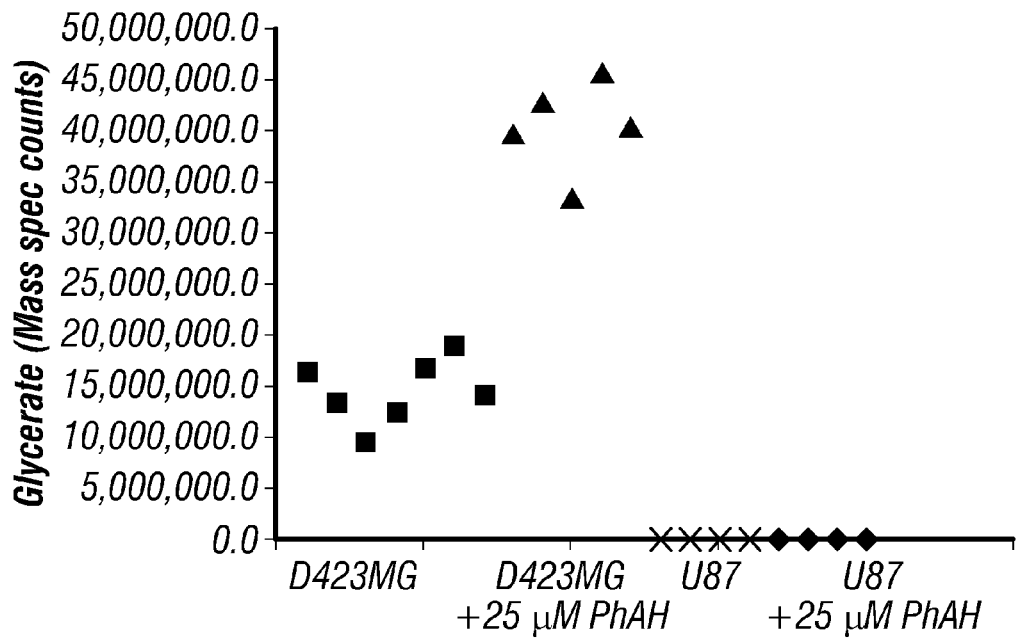
FIGS. 14A-D: Various metabolites are potential biomarkers to monitor treatment effectiveness when ENO1 deleted tumors are treated with an enolase 2 inhibitor. Metabolonics analysis of cell lysates reveals that upon treatment with the enolase inhibitor PhAH, glycerate and ethanolamine levels increase in ENO1 null cells D423MG, while their levels do not change in U87 cells, which are ENO1 wild type (panels a b and c) These metabolytes may accumulate in the serum of patients during treatment and could be used as a non-invasive way to assess for disease regression. Lactate levels decrease when enolase 2 is knocked down in ENO1 null cells (D423MG) using two independent hairpins (Panel d). Lactate is another potential biomarker used to monitor treatment response. Lactate leves in the tumor can be detected using MR spectroscopy imaging and a decrease in the lactate peak may correlate with tumor cell death.
Figure 14B:
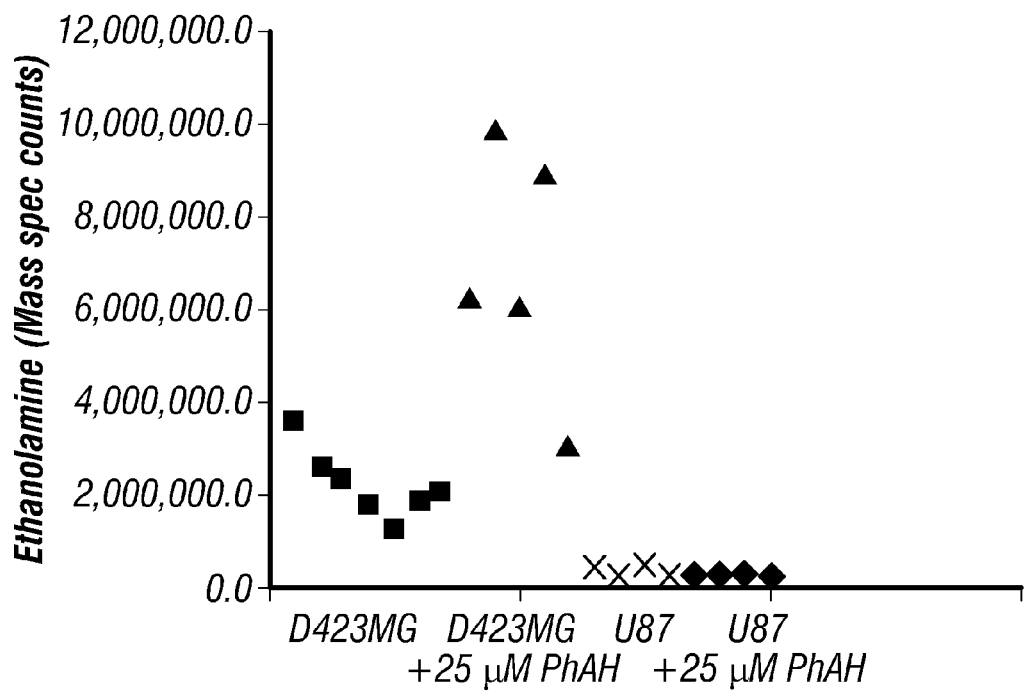
Figure 14D:
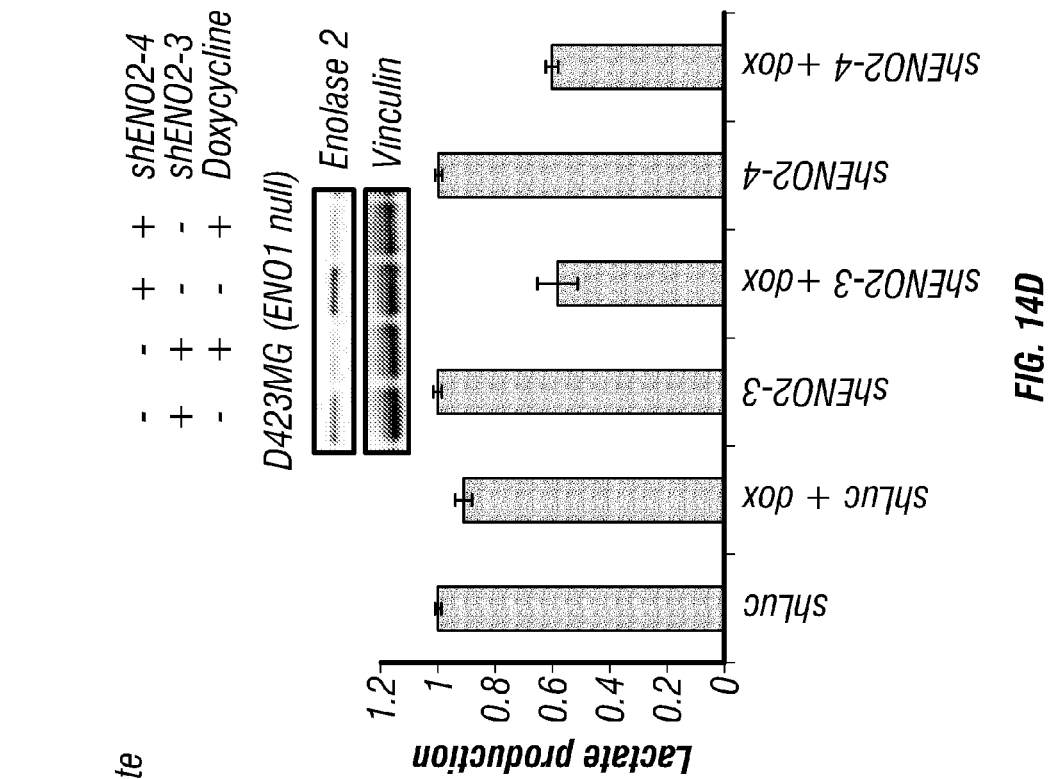
Figure 14C:
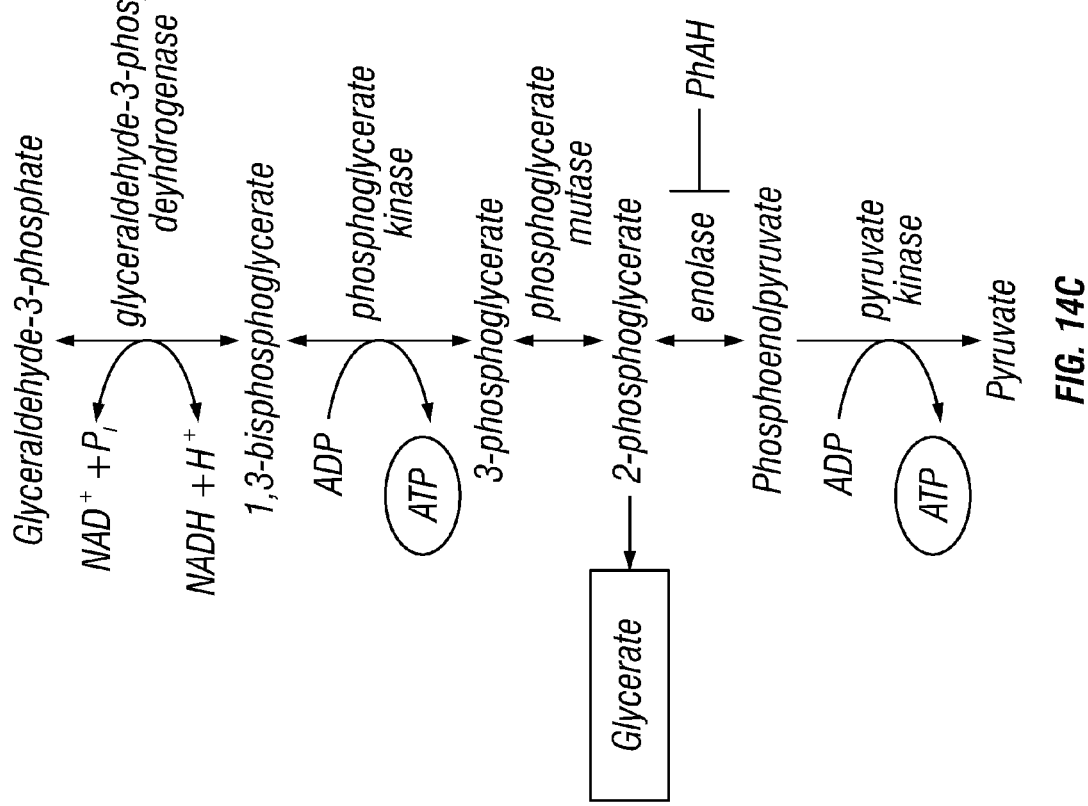

During treatment, response can be monitored either by non-ivasive imaging or by metabolic profiling. In the case of enolase inhibition in glioblastoma, for example, MR spectroscopy imaging (MRSI) could be an effective tool to use. This technique has been used to differentiate between brain tumor types and it also has potential applications for staging and predicting prognosis (Nelson et al.). It combines MRI with NMR spectroscopy to provide information about tissue metabolic profiles by detecting levels and spatial distribution of various metabolites, among which choline, creatine, N-acetylaspartate, lactate and lipid (Nelson et al.). A lactate peak corresponds to areas of anaerobic metabolism and in multiple studies it has been found to be markedly pronounced in glioblastomas (Moller-Hartmann et al.; Law). The data presented here shows that lactate levels decrease significantly after enolase 2 inhibition in ENO1 deleted cells in vitro (FIG. 14c). This may indicate that patients exhibiting a successful response to treatment will have decreased tumor lactate levels compared to baseline. Alternatively, it may be possible to analyze serum metabolites before and after treatment. Previous studies have shown that cancer patients can be differentiated from healthy patients with benign conditions based on their serum or urine metabolic profiles. This holds true for a wide variety of cancers, from ovarian cancer to hepatocellular carcinoma (Chen et al.; Odunsi; Spratlin et al.). Tumor metabolic changes upon treatment may be detected as changes in serum metabolites, in particular those that are upstream or downstream of the target protein. This way a specific biomarker can be found and used to monitor treatment effectiveness. The initial metabolic characterization of D423MG ENO1 null cells treated with PhAH indicates a profound upregulation of Glycerate (FIG. 14a). Glycerate is likely produced as a consequence of the spontaneous hydrolysis of 2-phosphoglycerate and 3-phosphoglycerate, the intermediates expected to accumulate immediately upstream of the enolase block (FIG. 14c). Glycerate is stable and of low abundance in normal serum and cerebrospinal fluid, hence may be a potential marker of inhibitor effectiveness.

Figure 15:
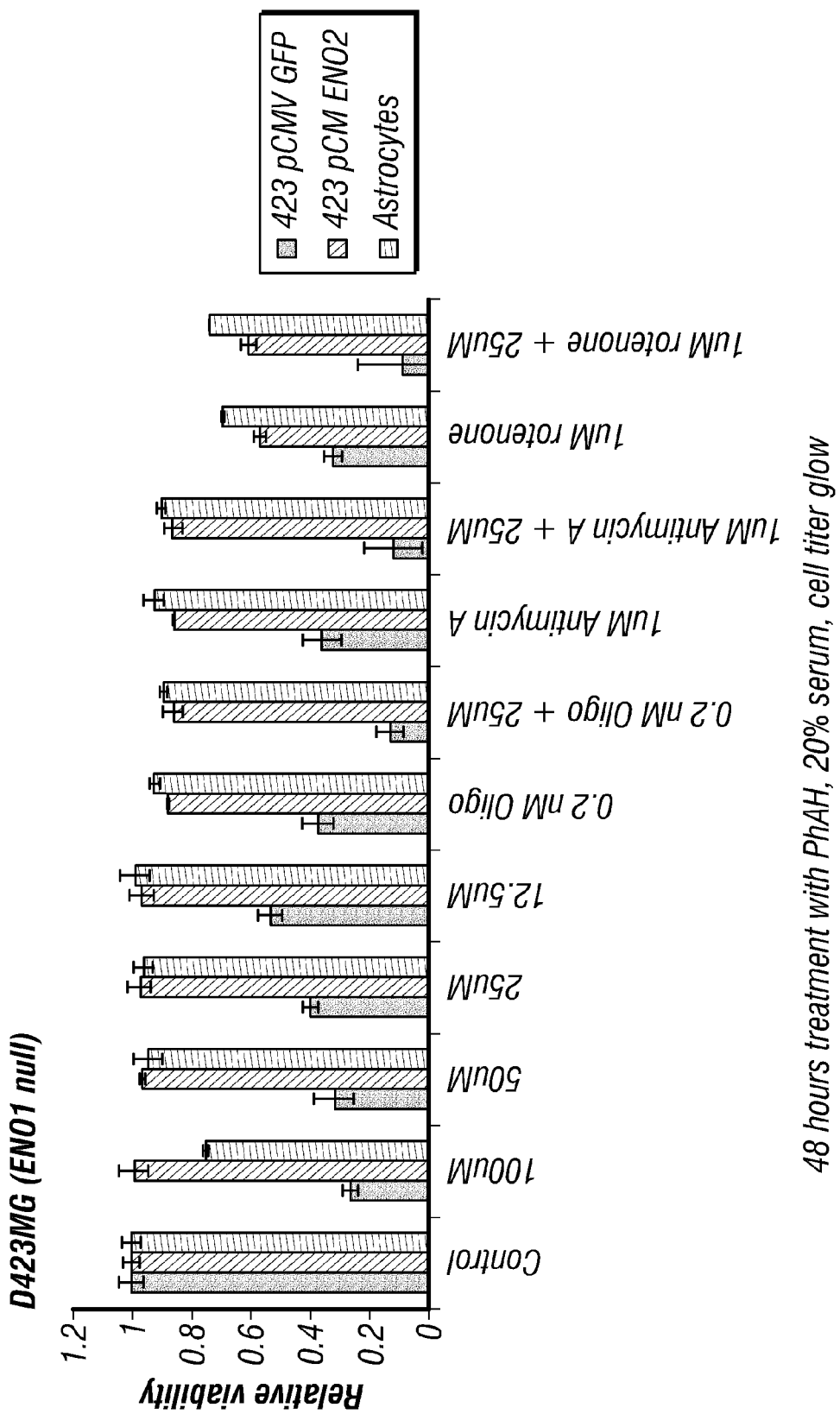
FIG. 15: The enolase inhibitor PhAH exerts a synergistic effect on ENO1 null cell death with inhibitors of mitochondrial metabolism such as oligomycin, antimycin A and rotenone. ENO1 null cells are more sensitive than human astrocytes to treatment with PhAH and the mitochondrial inhibitors. Cell viability of the D423MG line, as measured by a luciferase assay, is considerably lower when the mitochondrial inhibitors are used in combination with PhAH than when either of them is used alone. This effect is rescued by overexpression of enolase 2 in ENO1 null cells. This effect is also not seen in human astrocytes. This finding raises the interesting possibility of using an enolase inhibitor in combination with mitochondrial inhibitors to treat tumors with ENO1 homozygous deletions. Cells tested in each treatment were 423 pCMV GFP (ENO1 null)); 423 pCMV ENO2 (ENO1 null cells in which Enolase activity was restored by high overexpression of ENO2); and Astrocytes (from left to right).

Furthermore, inhibitors of homozygously deleted housekeeping genes may be used in combination with other chemotherapeutic treatments. It may be possible to use two compounds that act on similar pathways leading to a synergistic effect on cell death. The data shows that, for example, in ENO1 null cells an enolase inhibitor has a synergistic effect with inhibitors of mitochondrial metabolism such as oligomycin, antimycin A and rotenone (FIG. 15). This effect is not seen in cells that are ENO1 wild type and it is rescued by overexpression of enolase 2 in ENO1 null cells. An additional list of putative synergistic interactions is shown in Table 3.

Accordingly, the invention provides methods of treating cancer or inducing cell death in a cell that has a homozygous deletion in a housekeeping gene that has functionally redundant homologue by administering to the subject or contacting the cell with an inhibitor of the redundant homologue or an inhibitor of both homologs at appropriate doses, whereby cells lacking one of the two homologues require lower levels of the inhibitor (than healthy genomically intact) to reach therapeutically relevant inhibition level of the pathway.

II. Definitions

"Housekeeping gene" is meant a gene that is required for the maintenance of basic cellular function.

"Homozygous deletion", as used herein means that both alleles of a gene are deleted.

"Heterozygous deletion" as used herein means that one of the alleles of a gene is deleted.

As used herein a "functionally redundant homologue" or "functionally redundant homolog" of a given gene refers to a gene that can perform substantially the same function as the given gene. For example, in the case of a gene encoding an enzyme, the functionally redundant homologue would encode an enzyme that acts on the same substrate(s) at the same step in a metabolic pathway (e.g., enzymes having the same EC number).

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

Thus, treating may include suppressing, inhibiting, preventing, treating, or a combination thereof. Treating refers inter alia to increasing time to sustained progression, expediting remission, inducing remission, augmenting remission, speeding recovery, increasing efficacy of or decreasing resistance to alternative therapeutics, or a combination thereof. "Suppressing" or "inhibiting", refers inter alia to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. The symptoms are primary, while in another embodiment, symptoms are secondary. "Primary" refers to a symptom that is a direct result of the proliferative disorder, while, secondary refers to a symptom that is derived from or consequent to a primary cause. Symptoms may be any manifestation of a disease or pathological condition.

The "treatment of cancer or tumor cells", refers to an amount of small molecule or nucleic acid, described throughout the specification, capable of invoking one or more of the following effects: (1) inhibition of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer to shrink rr or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head and neck, kidney, lung, non-small cell lung, melanoma, mesothelioma, ovary, sarcoma, stomach, uterus and Medulloblastoma. Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, glioma, neuroblastoma, esophageal cancer, genitourinary tract cancer, malignant hypercalcemia, cervical cancer, endometrial cancer, adrenal cortical cancer, and prostate cancer.

A "proliferative disorder" is a disease or condition caused by cells which grow more quickly than normal cells, i.e., tumor cells. Proliferative disorders include benign tumors and malignant tumors. When classified by structure of the tumor, proliferative disorders include solid tumors and hematopoietic tumors.

The terms "patient" "subject" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, the term "administering to a cell" (e.g., an expression vector, nucleic acid, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

III. Further Housekeeping Genes

A Housekeeping gene in the context of the present invention is any gene that is required for the maintenance of basic cellular function. A large body of genetic interaction studies in invertebrates as well as mice indicates that many essential cellular housekeeping functions are carried out by multiple homologous genes (i.e., redundant homologues) encoding overlapping function that enables cell viability in the face of loss of one homologue but complete lethality upon loss of multiple homologues. (Deutscher et al. 2006; Costanzo et al. 2010; Vavouri et al. 2008; Brookfield et al. 1997)

Exemplary, housekeeping genes and their redundant homologue useful in the methods of the invention are described in Table 1. Housekeeping genes include for example but are not limited to endolase 1 (ENO1), hexose-6-phosphate dehydrogenase (H6PD), kinesin family member 1B (KIF1B), nicotinamide nucleotide adenylyl transferase 1 (NMNAT1), ubiquitination factor E4B (UBE4B), aconitase 1 (ACO1), kelch-like 9 (KLHL9), pantothenate kinase 1 (PANK1), and kinase family member 20B (KIF20B).

Table 1 shows a curated list of metabolic/housekeeping genes homozygously deleted in glioblastoma for which invertebrate-based evidence exists for essentiality as well as redundancy. Starting with a full list of homozygously deleted genes in the GBM-TCGA dataset (log 2 copy number <−1), we applied several filters to determine whether or not said deleted gene is an essential redundant housekeeping genes, i.e. ultimately, whether pharmacological inhibition of a homologue would result in tumor-specific cellular compromised function. In order to determine whether a deleted gene serves a housekeeping function, we first queried expression intensity and patterns in tumor and normal tissue as well as the general function of the gene. Second, we asked how conserved the gene is across phylogeny, and whether knockout data was available in invertebrate models (Saccharomyces Genome Database (SGD), Wormbase (WB), Flybase (FB). Third, we asked whether a known genetic interaction resulting in cell inviability was already documented in invertebrates or mice (using the databases SGD, Wormbase, Flybase, MGI). Fourth, we asked whether a small molecular inhibitor was available, that might be modified to selectively hit one homologue over the other. Fifth, we searched for available cell lines with the deleted genes in order to test the redundancy hypothesis. Finally, we searched MGI to determine whether knockout of the drug target-homologue is deleterious, in order to have some idea on how well a potential drug would be tolerate by the patient. The strongest candidates to emerge from this analysis are in decreasing order, ENO1/ENO2; PANK1/PANK3, ACO1/ACO3 and to a lesser extent, KIF20B/KIF20A pairs.

Pantothenate kinase is the first step in the biosynthesis of Coenzyme A, an essential co-factor for acetyl transfer reactions, fatty acid oxidation and lipid biosynthesis. Coenzyme A cannot be imported and must be synthesized in a cell autonomous manner. In yeast, flies and worms, there is only one isoform of the enzyme, and the knockout is lethal (Zhou et al. 2001) indicating that it is an essential gene. In mice and humans, there are three genes encoding PANK activity, the most widely expressed being PANK1 and PANK3 (Leonardi et al. 2010a; Leonardi et al. 2010b). Knockout of either PANK1 or 3 results in viable mice, whereas PANK1/3 double knockout mice are lethal during very early embryonic development (S. Jackowski, St Jude Children's Research Hospital, Memphis, Tenn., personal communications). An inhibitor of PANK, Hopantenate, showing some preference for PANK3 already exists, and has been used clinically in humans (Zhang 2007). Thus, inhibition of PANK3 (with a derivative of Hopantenate) in PANK1 null tumors should severely compromise the tumor cell growth but leave normal tissue untouched (given that PANK3 null mice are viable and more or less normal).

Aconitase 1 (ACO1) is a dual function enzyme playing an essential but redundant role in both iron metabolism and fueling mitochondrial respiration via generation of isocitrate from citrate. ACO2 is a mitochondrial isoform that does not control iron metabolism but is responsible for converting citrate into isocitrate in the Krebs cycle. In yeast, ACO1 and ACO2 single null mutants are viable with only the double null being lethal (Deutscher et al. 2006). Aco2$^{-/-}$ mice have not been reported, but Aco1$^{-/-}$ and Aco3$^{-/-}$ mice are viable and fertile. ACO3 is enzymatically inactive but like ACO1, regulates iron metabolism via binding of IRE in mRNA. Aco1$^{-/-}$Aco3$^{-/-}$ null mice unable to survive past E6.5 (Smith et al. 2006) as a consequence of massive iron deficiency. Thus, ACO1 homozygous deletion opens the tumor to two vulnerabilities: a) specific inhibition of ACO2 which would lead to inability of citrate/isocitrate conversion with implications for both bioenergetics and fatty acid production (Deutscher et al. 2006) and b) specific inhibition of ACO3/IREB2 which would lead to iron-starvation (Smith et al. 2006).

KIF20B (a.k.a. M-phase phosphoprotein 1) is kinesin motor enzyme initially thought to be required for completion of cytokinesis (Abaza et al. 2003). There are two KIF20 family members in mammals (KIF20A and KIF20B), but no direct 1:1 homologue in yeast. In *C. elegans* and *Drosophila*, one direct 1:1 homologue of KIF20 is present with genetic deletion resulting in early larval lethality (Moore et al. 1994) with evidence of massive cell death, suggesting that the mammalian homologues KIF20A and B may act redundantly. Indeed, just as for KIF20B, KIF20A has also been thought to be essential for cytokinesis (Hill et al. 2000) and both are highly upregulated during mitosis. Kinesins are ATP-dependent enzymes that are known to be "druggable" and have been explored with regards to cancer treatment (Parrish et al. 2007). A specific inhibitor of KIF20A, Paprotrain, was recently described (Tcherniuk et al. 2010). Furthermore, KIF20A has been explored as a "general" cancer drug target by siRNA in pancreatic cancer (Taniuchi et al. 2005).

ARS genes are essential and (in humans) non-redundant genes that are required for protein synthesis. Specifically, the genes are required for production of amino acid-loaded t-RNAs that can be utilized by ribosomes for polypeptide chain elongation. Examples of ARS genes that may be heterozygously inactivated in cancer cells include, without limitation, TARS (5q13); EPARS (1q41); VARS (6p21); IARS (9q24); CARS (11p15); SARS (1p13); YARS (1p35); AARS (16q23); KARS (16q24); LARS (5q31); HARS (5q32); and RARS (5q35) (notation in parenthesis indicate the chromosomal locations of the genes). Thus, in some cases, a cancer cell for treatment according to the embodiments may comprise a heterozygous deletion of two or more ARS genes (e.g., SARS and YARS; AARS and KARS; or LARS, HARS and RARS).

Other suitable housekeeping genes and redundant homologues are readily identifiable by those skilled in the art (see, e.g., Nijhawan et al., 2012, incorporated herein by reference).

IV. Detecting Mutations

Certain embodiments concern detecting, either in vivo or in a sample, a heterozygous inactivation of one copy of a gene, such as ENO1 or an ARS. For example, in some embodiments, an inactivation can be detected by detecting or measuring a change (a mutation) in the nucleic acid sequences of a cancer cell. In yet further aspects, gene inactivation is detected indirectly by detecting a reduced expression or reduced enolase activity associated with a cancer cell.

A. Nucleic Acid Detection

In some embodiments, assessing the presence of a heterozygous mutation, can involve detecting or quantifying a coding nucleic acid, such as an RNA or DNA encoding a gene product (e.g., ARS or ENO1. For example, in some aspects all or a portion of cancer cell genome is sequenced to detect the presence of a mutation (e.g., a substitution, deletion, inversion or insertion) in one copy of a gene. In some aspects, polymerase chain reaction (PCR) may be used to amplify all or part of an ENO1 or ARS sequence.

In further embodiments, a mutation in a gene coding sequence can be detected by determining the sequence of all or part of a coding RNA. For instance, reverse transcription PCR can be employed to determine the sequence of an ENO1 or ARS coding sequence. In still further aspects quantitative PCR or RT PCR can be employed to determine whether cells comprise a reduced amount of an enolase 1 coding sequence (e.g., corresponding to the inactivation of one copy of the gene).

In some embodiments, PCR products described above may be subjected to sequence analysis to identify specific kinds of variations using standard sequence analysis techniques. Within certain methods, exhaustive analysis of genes is carried out by sequence analysis using primer sets designed for optimal sequencing. The present embodiments provide methods by which any or all of these types of analyses may be used. Using the known sequence of the human genome (or cDNAs derived therefrom), oligonucleotide primers may be designed to permit the amplification of sequences throughout the ENO1 gene (or ARS gene) and surrounding sequence. Likewise, in some cases, DNA sequencing may be used to detect and/or quantify enolase 1 coding nucleic acids. Methods for such sequence include, but are not limited to, reversible terminator methods (e.g., used by Illumina® and Helicos® BioSciences), pyrosequencing (e.g., 454 sequencing from Roche) and sequencing by ligation (e.g., Life Technologies™ SOLiD™ sequencing).

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. Thus, these methods can be employed to detect ENO1 or ARS sequences that are heterozygously deleted in a cell or to detected a reduced overall expression of enolase 1 coding sequence.

In some embodiments, nucleic acids are detected or quantified following gel separation and staining with ethidium bromide and visualization under UV light. In some embodiments, if the nucleic acid results from a synthesis or amplification (e.g., by PCR) using integral radio- or fluorometrically-labeled nucleotides, the products can then be exposed to x-ray film or visualized under the appropriate stimulating spectra, following separation.

In some embodiments, visualization is achieved indirectly. Following separation of nucleic acids, a labeled nucleic acid is brought into contact with the target sequence. The probe is conjugated to a chromophore or a radiolabel. In another embodiment, the probe is conjugated to a binding partner, such as an antibody or biotin, and the other member of the binding pair carries a detectable moiety. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present embodiments.

Mutations in a gene can further be assessed by hybridization techniques. Northern and Southern blotting techniques are, for instance, well known to those of skill in the art. Northern and Southern blotting involves the use of RNA or DNA, respectively, as a target. Briefly, a probe is used to target an RNA or DNA species that has been immobilized on a suitable matrix, often a filter of nitrocellulose. The different species should be spatially separated to facilitate analysis. This often is accomplished by gel electrophoresis of nucleic acid species followed by "blotting" on to the filter. Subsequently, the blotted target is incubated with a probe (such as a labeled probe) under conditions that promote denaturation and rehybridization. Because the probe is designed to base pair with the target, the probe will binding a portion of the target sequence under renaturing conditions. Unbound probe is then removed, and detection is accomplished. Similarly, a labeled probe can be used for in situ hybridization to detect the presence of heterozygous mutations in (or the absence of one copy of) ENO1 or ARS. For example, fluorescence in situ hybridization (FISH) may be employed.

B. Detection Reduced Enolase 1 Protein Expression or Activity

In some aspects, methods of the embodiments concern detection of the expression or activity of enolase 1 proteins. For example, immunodetection methods for binding, purifying, removing, quantifying and/or otherwise generally detecting enolase 1 proteins can be employed. Antibodies prepared in accordance with the present embodiments may be employed to detect and/or quantify enolase 1 in a subject or sample, e.g., a tumor biopsy. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

1. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful.

In some embodiments, the anti-enolase 1 antibodies of the embodiments are immobilized onto a selected surface exhibiting protein affinity, such as a well in a polystyrene microtiter plate. Then, a test composition suspected of containing the protein antigen, such as a clinical sample, is added to the wells. After binding and/or washing to remove non-specifically bound immune complexes, the bound protein antigen may be detected. Detection is generally achieved by the addition of another anti-enolase 1 antibody that is linked to a detectable label. This type of ELISA is a simple "sandwich ELISA". Detection and quantification may also be achieved by the addition of a second anti-enolase 1 antibody, followed by the addition of a third antibody that has binding affinity for the second antibody, with the third antibody being linked to a detectable label.

In some embodiments, the samples suspected of containing the enolase 1 protein antigen are immobilized onto the well surface and/or then contacted with the anti-enolase 1 antibodies of the embodiments. After binding and/or washing to remove non-specifically bound immune complexes, the bound anti-enolase 1 antibodies are detected and quantified. Where the initial anti-enolase 1 antibodies are linked to a detectable label, the immune complexes may be detected directly. Again, the immune complexes may be detected using a second antibody that has binding affinity for the first anti-enolase 1 antibody, with the second antibody being linked to a detectable label.

In some embodiments, the enolase 1 proteins, polypeptides and/or peptides are immobilized. In some embodiments, ELISA involves the use of antibody competition in the detection. In this ELISA, labeled antibodies against a enolase 1 antigen are added to the wells, allowed to bind, and/or detected by means of their label. The amount of wild type or mutant enolase 1 antigen in an unknown sample is then determined by mixing the sample with the labeled antibodies against the antigen before and/or during incubation with coated wells. The presence of a enolase 1 antigen in the sample acts to reduce the amount of antibody against wild type or mutant protein available for binding to the well and thus reduces the ultimate signal. This is also appropriate for detecting antibodies against enolase 1 antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are steps are well known to a skilled artisan.

2. Immunohistochemistry

Anti-enolase 1 antibodies of the present embodiments may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections (e.g., vascular tissue sections) may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in 70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

3. Immunoelectron Microscopy

Antibodies of the present embodiments may also be used in conjunction with electron microscopy to identify intracellular tissue components. Briefly, an electron-dense label is conjugated directly or indirectly to an anti-enolase 1 antibody. Examples of electron-dense labels according to the embodiments are ferritin and gold. The electron-dense label absorbs electrons and can be visualized by the electron microscope.

4. Immunodetection Kits

In some aspects, the present embodiments concern immunodetection kits for use with the immunodetection methods described above. As anti-enolase 1 antibodies are generally used to detect such antigens, the antibodies will preferably be included in the kit. However, kits including both such components may be provided. Immunodetection kits will thus comprise, in suitable container means, a first antibody that binds to a protein, polypeptide and/or peptide (e.g., an anti-enolase 1 antibody), and/or optionally, an immunodetection reagent and/or further optionally, a purified or recombinant protein, polypeptide and/or peptide.

In some embodiments, monoclonal antibodies will be used. In certain embodiments, the first antibody that binds to the antigenic protein, polypeptide and/or peptide may be pre-bound to a solid support, such as a column matrix and/or well of a microtitre plate.

Immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and/or all such labels may be employed in connection with the present embodiments.

Kits in accordance with the present embodiments may further comprise a suitably aliquoted composition of the enolase 1 antigen, whether labeled and/or unlabeled, as may be used to prepare a standard curve for a detection assay. Provided kits may contain antibody-label conjugates either in fully conjugated form, in the form of intermediates, and/or as separate moieties to be conjugated by the user of the kit. The components of the kits may be packaged either in aqueous media and/or in lyophilized form.

The container means of the kits will generally include at least one vial, test tube, flask, bottle, syringe and/or other container means, into which the antibody may be placed, and/or preferably, suitably aliquoted. The kits of the present embodiments will also typically include a means for containing the antibody, antigen, and/or any other reagent containers in close confinement for commercial sale. Such containers may include injection and/or blow-molded plastic containers into which the desired vials are retained.

V. Inhibitors

An inhibitor is a compound that decreases the expression or activity of a redundant homologue of an essential housekeeping gene. A decrease in expression or activity is defined by a reduction of a biological function of the redundant homologue of the essential housekeeping gene. Inhibitors are known in the art or are identified using methods described herein. Housekeeping gene activity is measured by methods known in the art.

Exemplary, inhibitors for useful in the methods of the invention are described in Table 1. Other suitable inhibitors are readily identifiable by those skilled in the art by known methods.

For example, when the housekeeping gene is enolase the inhibitor is phosphonoacetohydroxamate. When the housekeeping gene is hexose-6-phosphate dehydrogenase (H6PD) and the redundant homologue is glucose-6 dehydrogenase (G6PD), the inhibitor can comprise, for example, dehyroepiandosterone.

When the housekeeping gene is nicotinamide nucleotide adenylyl transferase 1 (NMNAT1) and the redundant homologue is Nicotinamide nucleotide adenylyl transferase 2 (NMNAT2) or nicotinamide nucleotide adenylyl transferase 3 (NMNAT3), the inhibitor is for example; Np3AD, Np4As And Nap4AD. When the housekeeping gene is aconitse 1 (ACO1) and the redundant homologue is aconitase 2 (ACO2) or aconitase 3(ACO3), the inhibitor is for example, fluorocitrate. When the housekeeping gene is pantothenate kinase 1 (PANK1) and the redundant homologue is pantothenate kinase 3 (PANK3), the inhibitor is for example hopantenate.

A. Glycoloysis Inhibitors

Embodiments of the present invention relate to compositions and methods aimed at effectively treating cancer cells with inhibitors of glycolysis. For example, a glycolysis inhibitor can be an inhibitor of a pyruvate kinase (e.g., PKLR1 or PKM2), enolase (e.g., ENO1, ENO2 or ENO3), phosphoglycerate mutase (e.g., PGM1, PGM2, PGM2L1, PGM3 or PGM5), phosphoglycerate kinase (e.g., PGK1 or PGK2), glyceraldehydes phosphate dehydrogenase (GAPDH), triosephosphate isomerase (TPI), fructose biphosphate aldolase (e.g., Aldoa, Aldob or Aldoc), phosphofructokinase (PFK1), phosphoglucose isomerase (GPI) or hexokinase (e.g., HK1, HK2 or HK3).

In some aspects, the glycolysis inhibitor is a nucleic acid or polypeptide inhibitor. For example, the inhibitor can be a an antibody or fragment thereof that binding to a glycolytic enzyme, such as a pyruvate kinase, enolase, phosphoglycerate mutase, phosphoglycerate kinase, GAPDH, TPI, fructose biphosphate aldolase, phosphofructokinase, GPI or hexokinase. In further aspects, the inhibitor can be an inhibitory nucleic acid that binds to all or part of a nucleic acid molecule encoding a glycolytic enzyme. For example, the inhibitory nucleic acid can be an RNA complementary to all or part of an mRNA encoding PKLR1 PKM2, ENO1, ENO2, ENO3, PGM1, PGM2, PGM2L1, PGM3, PGM5 PGK1, PGK2, GAPDH, TPI, Aldoa, Aldob, Aldoc, PFK1, GP1, HK1, HK2 or HK3.

In still further aspects, the glycolysis inhibitor is a small molecule inhibitor or a prodrug thereof. For example, the small molecule inhibitor can be an inhibitor of a pyruvate kinase, enolase, phosphoglycerate mutase, phosphoglycerate kinase, GAPDH, TPI, fructose biphosphate aldolase, phosphofructokinase, GPI or hexokinase. Example, glycolysis inhibitor compounds include, without limitation, 2-deoxyglucose, 6-aminonicotinamide, tetrose diphosphate, koningic acid and MJE3. Further, exemplary glycolysis inhibitors include compositions related to pyruvate. For example, pyruvate derivates are described in U.S. Patent Application Publications US 2003/0013656, US 2003/0013847, US 2003/0013657, and US 2003/0013846.

In some preferred aspects, the glycolysis inhibitor is an enolase inhibitor. Examples of such enolase inhibitors include, without limitation, D-tartronate semialdehyde phosphate; 3-aminoenolpyruvate-2-phosphate; phosphonoacetohydroxamate (PhAH); 2-fluoro-2-phosphonoacetohydroxamate; (3-hydroxy-2-nitropropyl) phosphonate; (nitroethyl) phosphonate; d-(phosphonoethyl)nitrolate, fluorides and prodrugs and derivatives thereof.

B. ARS Inhibitors

In certain embodiments the invention concerns ARS inhibitors and the administration thereof for use in treating cancers having a heterozygous inactivation of the one or more ARS gene(s). In some aspects, the ARS inhibitor preferentially inhibits eukaryotic aminoacyl tRNA. For example, the ARS inhibitor can be an agent that inhibits a prolyl tRNA synthetase, a cysteinyl tRNA synthetase, a glycyl tRNA synthetase, an alanyl tRNA synthetase, an aspartyl tRNA synthetase, a glutamyl tRNA synthetase, an asparagyl tRNA synthetase, a glutaminyl tRNA synthetase, a seryl tRNA synthetase, an arginyl tRNA synthetase, a histidyl tRNA synthetase, a tyrosyl tRNA synthetase, or a glutamyl-prolyl-tRNA synthetase (e.g., halofuginone). Examples of ARS inhibitors include, without limitation, the TARS inhibitor, Borrelidin, as well as anti-microbial ARS inhibitors (and derivatives thereof) such as Mupirocin; SB-234764; Indolmycin; AN-2690; CB-432; Icofungipen; REP8839; Cispentacin; Chuangxinmycin; Microcin C (or precessed Microcin C); Phosmidosin; Ascamycin; Agrocin; SB-217452; or Albomycin. Additional inhibitors that can be used in accordance with methods of the instant embodiments are provided in U.S. Patent Publn. 20120058133, incorporated herein by reference.

C. Prodrugs

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. In general, such prodrugs will be functional derivatives of the glycolysis inhibitors of the embodiments, which are readily convertible in vivo into the active glycolysis inhibitor. Conventional procedures for the selection and preparation of suitable prodrug derivatives are described, for example, in "Design of Prodrugs", ed. H. Bundgaard, Elsevier, 1985; Huttunen et al., 2011; and Hsieh et al., 2009, each of which is incorporated herein by reference in its entirety.

A prodrug may be a pharmacologically inactive derivative of a biologically active glycolysis inhibitor (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality. Thus, prodrugs of the compounds employed in the embodiments may be prepared by modifying functional groups present in the compound in such a way that the modifications are cleaved, either in routine manipulation or in vivo, to the parent compound. Prodrugs include, for example, compounds described herein in which a hydroxy, amino, or carboxy group is bonded to any group that, when the prodrug is administered to a subject, cleaves to form a hydroxy, amino, or carboxylic acid, respectively. Thus, the invention contemplates prodrugs of compounds of the present invention as well as methods of delivering prodrugs.

VI. Combination Therapies

In order to increase the effectiveness of a glycolysis inhibitor of the present embodiments, it may be desirable to combine these compositions with other agents effective in the treatment of cancer. As a non-limiting example, the treatment of cancer may be implemented with glycolysis inhibitor along with other anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This may be achieved by contacting the cell (or administering a subject) with a single composition or pharmacological formulation that includes both agents, or by contacting the cell with two distinct compositions or formulations, at the same time, wherein one composition includes the glycolysis inhibitor and the other includes the second agent(s).

Treatment with the glycolysis inhibitor may precede or follow the other agent or treatment by intervals ranging from minutes to weeks. In embodiments where the other agent and the glycolysis inhibitor are applied separately to the cell, one would generally ensure that a significant period of time did not expire between the time of each delivery, such that the agent and the glycolysis inhibitor would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6 or 7 days) to several weeks (e.g., 1, 2, 3, 4, 5, 6, 7 or 8 weeks) lapse between the respective administrations.

Various combinations may be employed, where the glycolysis inhibitor therapy is "A" and the secondary agent or treatment, such as radiotherapy, chemotherapy or mitochondrial electron transport inhibitor, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

In certain embodiments, administration of the glycolysis inhibitor therapy of the present embodiments to a patient will follow general protocols for the administration of chemotherapeutics, taking into account the toxicity, if any, of the inhibitor. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of combination therapies. In some aspects, a glycolysis inhibitor of the embodiments is administered (or formulated) in conjunction with a chemotherapeutic agent. Combination chemotherapies include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above. In certain embodiments, the compositions provided herein may be used in combination with gefitinib. In other embodiments, the present embodiments may be practiced in combination with Gleevac (e.g., from about 400 to about 800 mg/day of Gleevac may be administered to a patient). In certain embodiments, one or more chemotherapeutic may be used in combination with the compositions provided herein.

B. Radiotherapy

Other factors effective for cancer therapy and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with a glycolysis inhibitor therapy of the present embodiments. The general approach for combined therapy is discussed below. Generally, the tumor cell must bear some marker that is amenable to targeting, i.e., is not present on the majority of other cells. Many tumor markers exist and any of these may be suitable for targeting in the context of the present embodiments. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Gene Therapy

In yet another embodiment, the secondary treatment is a gene therapy in which a therapeutic polynucleotide is administered before, after, or at the same time as the therapeutic composition. Viral vectors for the expression of a gene product are well known in the art, and include such eukaryotic expression systems as adenoviruses, adeno-associated viruses, retroviruses, herpesviruses, lentiviruses, poxviruses including vaccinia viruses, and papiloma viruses, including SV40. Alternatively, the administration of expression constructs can be accomplished with lipid based vectors such as liposomes or DOTAP:cholesterol vesicles. All of these method are well known in the art (see, e.g. Sambrook et al., 1989; Ausubel et al., 1998; Ausubel, 1996).

Delivery of a vector encoding one of the following gene products will have a combined anti-hyperproliferative effect on target tissues. A variety of proteins are encompassed within the present embodiments, some of which are described below.

1. Inhibitors of Cellular Proliferation

As noted above, the tumor suppressor oncogenes function to inhibit excessive cellular proliferation. The inactivation of these genes destroys their inhibitory activity, resulting in unregulated proliferation.

Genes that may be employed as secondary treatment in accordance with the present embodiments include p53, p16, Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors), MCC and other genes listed in Table IV.

2. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatments provided herein, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present embodiments may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the compositions provided herein to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the compositions provided herein by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the compositions provided herein to improve the anti-hyperproliferative efficacy of the treatments Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the compositions provided herein to improve the treatment efficacy.

In certain embodiments, hormonal therapy may also be used in conjunction with the present embodiments or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VII. Therapeutic Methods

The growth of cells is inhibited, e.g. reduced or cell death is induced by contacting a cell with a composition containing an inhibitor. By inhibition of cell growth is meant the cell proliferates at a lower rate or has decreased viability compared to a cell not exposed to the composition. Cell growth is measured by methods know in the art such as, crystal violet, trypan blue, or measurement of ATP, NADH, Capases, LDH or MTT.

Cells are directly contacted with an inhibitor. Alternatively, the inhibitor is administered systemically. Inhibitors are administered in an amount sufficient to decrease (e.g., inhibit) cell proliferation or induce a cell death.

Optionally, the cell in contacted with a chemotherapeutic compound. In particular the chemotherapeutic compound targets a metabolic pathway of the housekeeping gene. For example, the chemptherapuetic compound targets DNA homeostasis. Exemplary chemotherapeutic compounds include gemcitabine.

The cell is a tumor cell such as a carcinoma, adenocarcinoma, blastoma, leukemia, myeloma, or sarcoma. In particular, the cancer is a glioblastoma.

In various aspects the cell has a homozygous deletion of one or more housekeeping genes which has a redundant homologue. Homozygous deletions are identified by methods known in the art.

The methods are useful to alleviate the symptoms of a variety of cancers. Any cancer containing homozygous deletion in a housekeeping gene which has a redundant homologue is amendable to treatment by the methods of the invention. In some aspects he subject is suffering from gliolastoma.

Treatment is efficacious if the treatment leads to clinical benefit such as, a decrease in size, prevalence, or metastatic potential of the tumor in the subject. When treatment is applied prophylactically, "efficacious" means that the treatment retards or prevents tumors from forming or prevents or alleviates a symptom of clinical symptom of the tumor. Efficaciousness is determined in association with any known method for diagnosing or treating the particular tumor type.

Also included in the invention are methods of determining the efficacy of treatment by the therapeutic methods of the invention. Efficaciousness of treatment is determined by measuring the level of one or more metabolites of the metabolic pathway of the housekeeping gene in a sample from the subject. Stalling a pathway in cells will lead to an accumulation of metabolites that precede the produce of the housekeeping gene. This an accumulation of the metabolite indicates that the treatment is efficacious.

For example upon inhibition of enolase 2, stalling of the glycolytic pathway in cells will lead to accumulation of metabolites that precede the product of enoalse, most immediately, 2-phosphoglycerate. Tumors treated effectively are expected to release these metabolites in the bloodstream at a rate that correlates with the rate of enolase inhibition effectiveness. Measuring serum levels of these metabolites will allow us to monitor tumor targeting effectiveness. We will also perform metabolonic profiling of cell lines treated with the specific inhibitor, to determine what additional metabolites build up and may be most usable in serum profiling or further refining treatment.

VIII. Therapeutic Administration

The invention includes administering to a subject a composition comprising an inhibitor.

An effective amount of a therapeutic compound is preferably from about 0.1 mg/kg to about 150 mg/kg. Effective doses vary, as recognized by those skilled in the art, depending on route of administration, excipient usage, and coadministration with other therapeutic treatments including use of other anti-proliferative agents or therapeutic agents for treating, preventing or alleviating a symptom of a cancer. A therapeutic regimen is carried out by identifying a mammal, e.g., a human patient suffering from a cancer that has a homozygous deletion of a essential housekeeping gene using standard methods.

The pharmaceutical compound is administered to such an individual using methods known in the art. Preferably, the compound is administered orally, rectally, nasally, topically or parenterally, e.g., subcutaneously, intraperitoneally, intramuscularly, and intravenously. The inhibitors are optionally formulated as a component of a cocktail of therapeutic drugs to treat cancers. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, the therapeutic compounds are formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, conventional filler, and a tableting agent. Other formulations include an ointment, suppository, paste, spray, patch, cream, gel, resorbable sponge, or foam. Such formulations are produced using methods well known in the art.

Therapeutic compounds are effective upon direct contact of the compound with the affected tissue. Accordingly, the compound is administered topically. Alternatively, the therapeutic compounds are administered systemically. For example, the compounds are administered by inhalation. The compounds are delivered in the form of an aerosol spray from pressured container or dispenser which contains a suitable propellant, e.g., a gas such as carbon dioxide, or a nebulizer.

Additionally, compounds can be administered by implanting (either directly into an organ or subcutaneously) a solid or resorbable matrix which slowly releases the compound into adjacent and surrounding tissues of the subject.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Targeting Housekeeping Genes in Cancer Cells with Homozygous Deletions Results in Cancer Cell Death Cancer cell proliferation and or death is induced where the cancer has a homozygous deletion in a housekeeping gene and the housekeeping gene has a functionally redundant homologue by administering to the subject or contacting a cell with an inhibitor of the redundant homologue in an amount sufficient to inhibit the activity of the redundant homologue.

General Methods

Cell Culture

Cell lines having the homozxygous deletion are cultures using know methods. (1p36 For comparative purposes, cell lines U87, LN319, SW1088, U343, U373 and A1207 are grown under the same conditions.

shRNA Knockdown of Housekeeping Gene Expression

Hairpins targeting the houskeping gene are prepared and screened for their ability to reduce protein levels of the housekeeping gene.

The hairpin in the GIPZ vector was cloned into the TRIPZ vector using a protocol provided by the manufacturer. The TRIPZ vector is a doxycycline inducible system with a Red fluorescent protein reporter which is only expressed upon doxycycline induction. Recombinant lentivirus is produced by transient transfection of 293T cells following a standard protocol. Briefly, 72 µg of the shRNA plasmid, 54 µg of Delta 8.9 and 18 µg of VSVG plasmids are transfected using Fugene® (Roche, Indianapolis, Ind.) into 293T cells plated in 245 $mm^2$ dishes. Viral supernatant is collected 72 hours after transfection, concentrated by centrifugation at 23,000 rpm and resuspended in cell growth medium. For transduction, viral solutions are added to cell culture medium containing 4 µg/mL polybrene; 48 hours after infection cells are selected using 2 µg/mL puromycin and tested for housekeeping gene knockdown by western blot.

Generation of an shRNA Resistant Housekeeping Gene Construct

The rescue of the phenotypic effects of knocking the housekeeping gene in the cell is performed by overexpressing an shRNA-resistant form of the housekeeping gene. Briefly, 6 silent mutations are introduced in the housekeeping gene coding region targeted by shRNA, using site-directed mutagenesis according to QuickChange Kit (Stratagene, La Jolla, Calif., USA). The shRNA-resistant housekeeping gene coding region is cloned into the pHAGE-CMV lentiviral vector and overexpressed in the cell line carrying shRNA in the presence or absence of doxycycline. As a control, the same cell line is infected by a lentiviral vector carrying the GFP gene.

Proliferation Assays

Cell growth of shRNA or PhAH treated cell lines is assayed either through crystal violet staining or using the Promega Cell Titer Glo® proliferation kit (Roche, Indianapolis, Ind.). For crystal violet assays, 10,000 cells are seeded in a 6-well plate for each time point. At the indicated time point, cells are fixed with 10% formalin and stained with crystal violet solution for 1 hour. Dye extraction is performed using 10% acetic acid solution and absorbance was read at 590 nm. Cell titer Glo® experiments are performed as indicated by the manufacturer. 1000 cells/well are plated in a 96 well plate for each time point and luminescence readings are taken every 24 hours. All experiments are performed in triplicate.

Housekeeping Gene Activity Assay

Activity of the housekeeping gene is measured using methods known in the art.

Western Blot

After 2 PBS washes, cells are incubated in RIPA buffer for 15 min with gentle shaking Lysates are then collected, sonicated and centrifuged at 14000 RPM for 10 min at 4° C. SDS-PAGE and Western blots are the performed as previously (Maser et al., 2007).

Example 2

Inhibition of ENO2 activity induces cell death in cell lines with a homozygous deletion of ENO1

General Methods

Cell Culture

Cell lines D423-MG (1p36 homozygous deleted including ENO1) and

D502-MG (1p36 homozygously deleted, but excluding ENO1) were obtained and cultured in DMEM medium with 20% FBS (Duncan et al., 2010; D423 and D502 are referred to as H423 and H502 in Duncan et al., but as D423-MG and D502-MG in the Sanger database, the nomenclature adopt here). For comparative purposes, cell lines U87, LN319, SW1088, U343, U373 and A1207 were grown under the same conditions. Normal embryonic human astrocytes obtained from ScienCell (Carlsbad, Calif.) were grown in media provided by the manufacturer.

shRNA Knockdown of ENO2 Expression 22 hairpins targeting enolase 2 were screened and 4 independent ones found that yielded a reduction in protein levels >50%. Two of these hairpins were in the pLKO.1 vector (ShENO2-1 and shENO2-2) and the remaining two were in the Expression Arrest GIPZ (shENO2-3) and TRIPZ (shENO2-4) shRNAmir vectors (Open Biosystems, Huntsville, Ala.). The hairpin in the GIPZ vector was cloned into the TRIPZ vector using a protocol provided by the manufacturer. The TRIPZ vector is a doxycycline inducible system with a Red fluorescent protein reporter which is only expressed upon doxycycline induction. Recombinant lentivirus was produced by transient transfection of 293T cells following a standard protocol. Briefly, 72 µg of the shRNA plasmid, 54 µg of Delta 8.9 and 18 µg of VSVG plasmids were transfected using Fugene® (Roche, Indianapolis, Ind.) into 293T cells plated in 245 mm2 dishes. Viral supernatant was collected 72 hours after transfection, concentrated by centrifugation at 23,000 rpm and resuspended in cell growth medium. For transduction, viral solutions were added to cell culture medium containing 4 µg/mL polybrene; 48 hours after infection cells were selected using 2 µg/mL puromycin and tested for ENO2 knockdown by western blot.

Generation of a shRNA Resistant ENO2 Construct

The rescue of the phenotypic effects of knocking ENO2 in the cell line D423-MG was performed by overexpressing a shRNA-resistant form of ENO2. Briefly, 6 silent mutations were introduced in the ENO2 coding region targeted by shENO2-4, using site-directed mutagenesis according to QuickChange Kit (Stratagene, La Jolla, Calif., USA). The shRNA-resistant ENO2 coding region was cloned into the pHAGE-CMV lentiviral vector and overexpressed in the D423-MG cell line carrying shENO2-4, in the presence or absence of doxycycline. As a control, the same cell line was infected by a lentiviral vector carrying the GFP gene.

Proliferation Assays

Cell growth of shRNA or PhAH treated cell lines was assayed either through crystal violet staining or using the Promega Cell Titer Glo® proliferation kit (Roche, Indianapolis, Ind.). For crystal violet assays, 10,000 cells were seeded in a 6-well plate for each time point. At the indicated time point, cells were fixed with 10% formalin and stained with crystal violet solution for 1 hour. Dye extraction was performed using 10% acetic acid solution and absorbance was read at 590 nm. Cell titer Glo® experiments were performed as indicated by the manufacturer. 1000 cells/well were plated in a 96 well plate for each time point and luminescence readings were taken every 24 hours. All experiments were performed in triplicate.

Soft Agar Colonly Formation Assay

Anchorage-independent growth assays were performed in duplicate or triplicate in 6 well plates. $10^4$ of indicated cells per well were seeded in DMEM+10% FBS containing 0.4% low-melting agarose on the top of bottom agar containing 1% low-melting agarose DMEM+10% FBS. After 14-21 days, colonies were stained with iodonitrotetrazoliumchloride (Sigma-Aldrich) and counted.

The Orthotopic Tumorigenesis Assays

Injection of D423-MG cells was performed as previously described (in Zheng et al., 2008) SCID mice (Charles River) aged 6-12 weeks were placed into stereotactic apparatus equipped with a Z axis (Stoelting). A hole was bored in the skull 0.5 mm anterior and 3.0 mm lateral to the bregma using a dental drill. One hundred thousand cells in Hanks Buffered Salt Solution were injected into the right caudate nucleus 3 mm below the surface of the brain using a 10-µl Hamilton syringe with an unbeveled 30 gauge needle. The scalp was closed using a 9-mm Autoclip Applier. Animals were followed daily for the development of neurological deficits.

Animals were followed daily for development of neurological deficits. All mice experiments were performed with the approval of the Harvard and Dana-Farber Cancer Institute Institutional Animal Care and Use Committee.

Enolase Activity Assay enolase activity was measured following NADH oxidation in a pyruvate kinase-lactate dehydrogenase coupled assay as previously described in Joseph et al., 1996. Briefly, cells were lysed in 20 mM Tris HCL, 1 mM EDTA and 1 mM beta-mercaptoethanol pH 7.4 and homogenized using a polytron homogenizer three times for a period of 10 seconds followed by sonication. Enolase activity was recorded by measuring oxidation of NADH either spectrophotometrically by absorbance at 340 nm or fluorescently by excitation at 340 nm emission at 460 nm.

Western Blot

After 2 PBS washes, cells were incubated in RIPA buffer for 15 min with gentle shaking Lysates were then collected, sonicated and centrifuged at 14,000 RPM for 10 min at 4° C. SDS-PAGE and Western blots were the performed as previously Maser et al., 2007. The following antibodies were used: Enolase 1 CST#3810; Enolase 2 #9536; GAPDH CST#3683 from Cell signaling Technologies (Danvers, Mass.) and Vinculin from Sigma-Aldrich (St Louis, Mo.).

Inhibitor Studies

Phosphonoacetohydroaxamate Lithium salt (PhAH) was custom synthesized by TCRS LLC (Bristol, Pa.), following the protocol of Anderson et al., 1984. Structure and purity were verified by NMR. PhAH was dissolved in PBS at 50 mM stock and stored frozen at −80° C. until use. Given the instability of the compound, media was replaced every 5 days and fresh inhibitor added with fresh media. Rapamycin, sorafenib, lapatinib and PHA665752 were obtained from LC Labs (Woburn, Mass.) and Tocris (Ellisville, Mo.), respectively.

Results

Figure 1B:
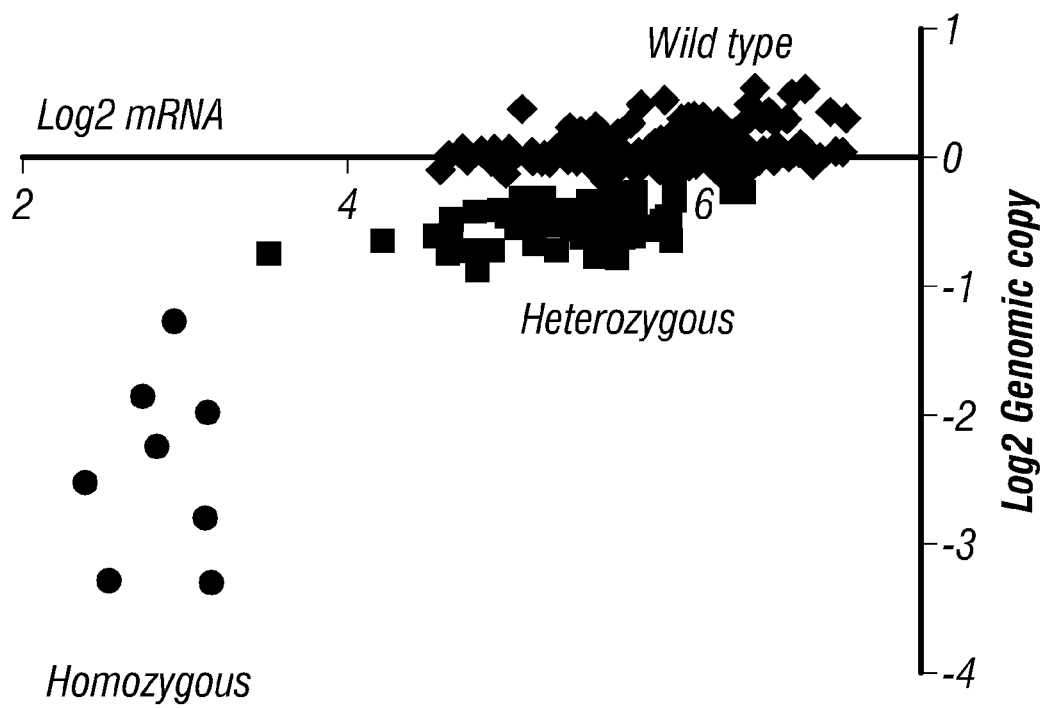
Figure 1C:
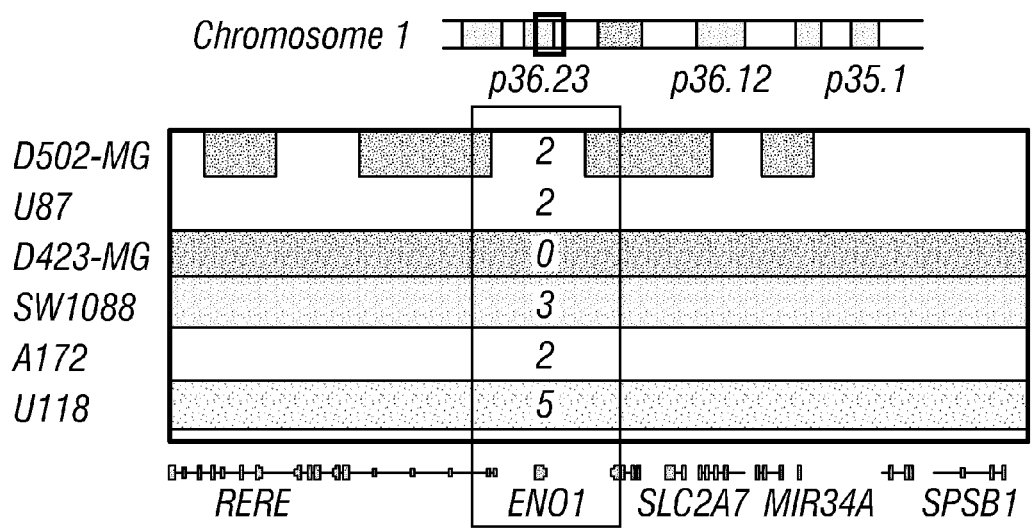
Figure 1D:
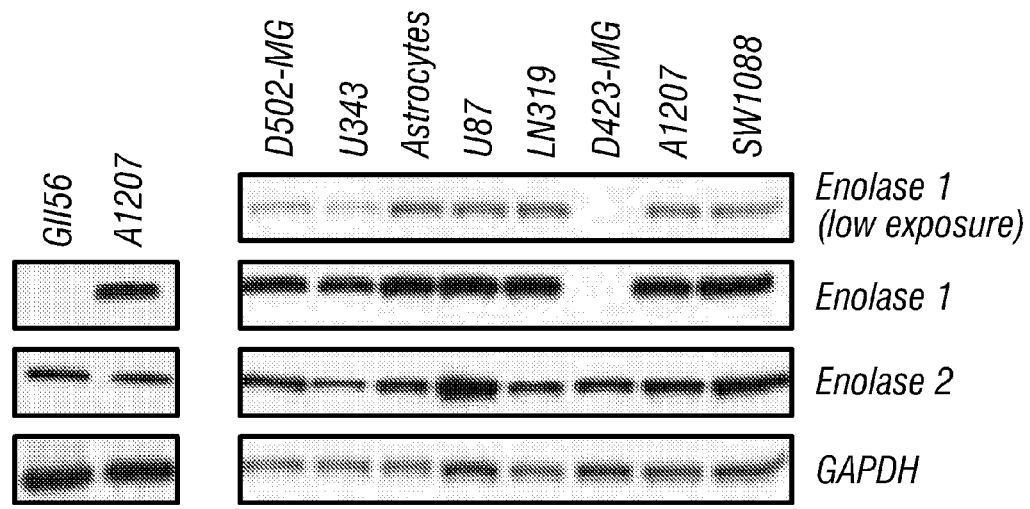

Analysis of the TCGA Agilent SNP array data and Affymetrix array CGH data database (The Cancer Genome Atlas Research Network, 2008) reveals 5/359 GBM samples with homozygous deletion of ENO1; Other genomic datasets show ENO1 homozygous deletion frequencies of up to 5% 16, 19, 20. Gene expression analysis shows near complete absence of enolase 1 expression in these samples (FIG. 1b, FIG. 18). A GBM cell line, D423-MG20, was identified with a 1p36.23 homozygous deletion spanning CAMTA1, VAMP3, PER3, UTS2, TNFRSF9, PARK7, ERRFI1, SLC45A1, RERE, ENO1, CA6, SLC2A5, GPR157, MIR34A, H6PD, SPSB1, and SLC25A33 genes. A second GBM cell line, D502-MG, also incurs homozygous deletion of this locus yet leaves intact ENO1 through SLC25A33 genes (FIG. 1c). Western blot analysis of these lines shows loss of enolase 1 protein and normal expression of enolase 2 in D423-MG and presence of both proteins in D502-MG and all other glial/glioma cell lines tested (FIG. 1d).

Figure 2B:
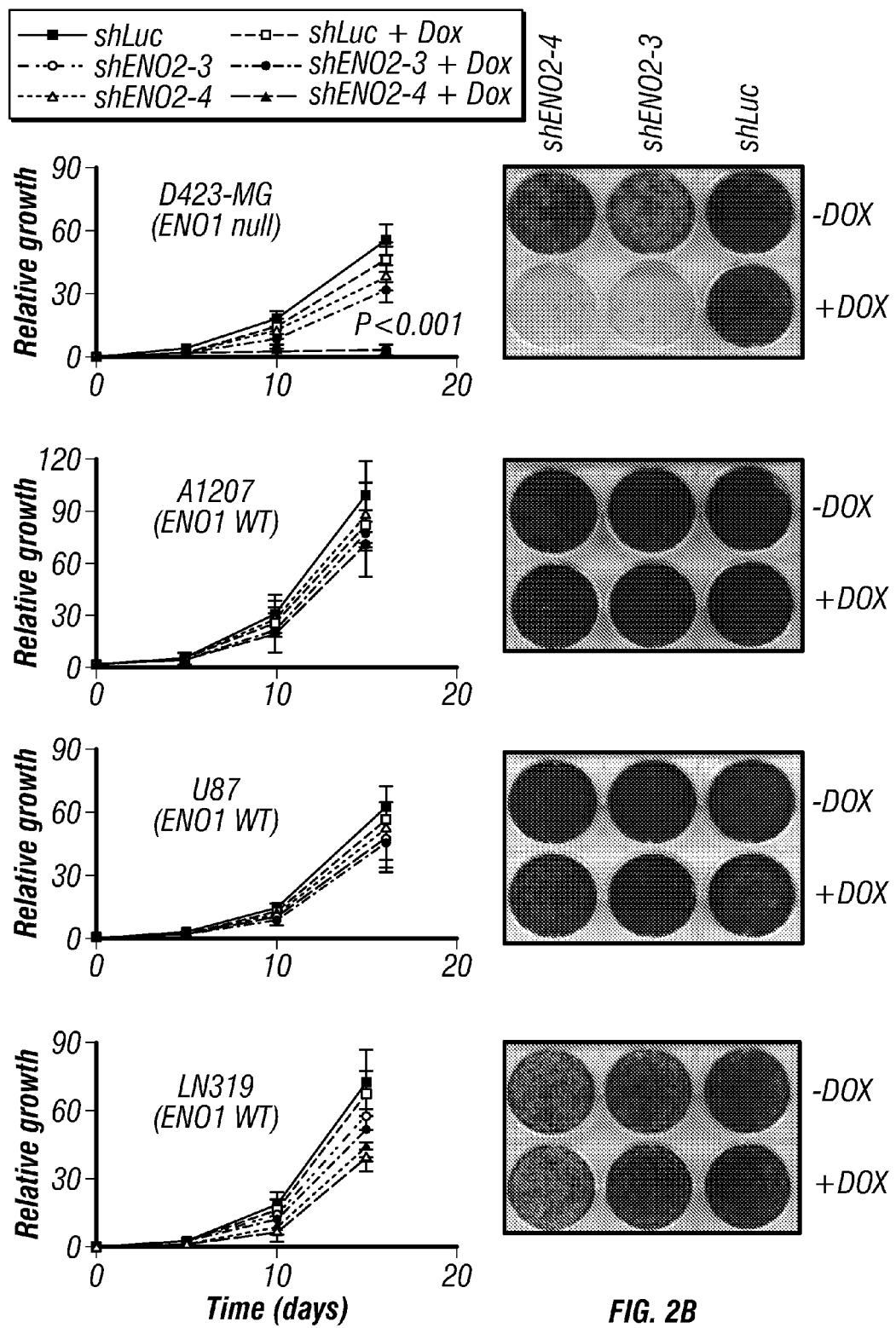

These two cell lines, along with other ENO1 intact controls (U87, A1207, LN319) were used to assess the impact of shRNA-mediated knockdown of enolase 2 in a wild type or null ENO1 context. Using a doxycycline-inducible system, two independent shRNAs were effective in producing >70% reduction of enolase 2 protein (FIG. 2a) and showed no effect on enolase 1 levels. This ablation of ENO2 resulted in a profound inhibition of cell proliferation only in the ENO1 null D423-MG (FIG. 2b). The same result was obtained using two additional independent enolase 2 shRNAs in a non-inducible system (FIG. 5). It was further shown that expression of a hairpin resistant ENO2 construct completely reverses the deleterious effects of the shENO2 hairpin (FIG. 7), indicating that the effect of the hairpin was indeed specific to downregulation of ENO2 expression.

Figure 3B:
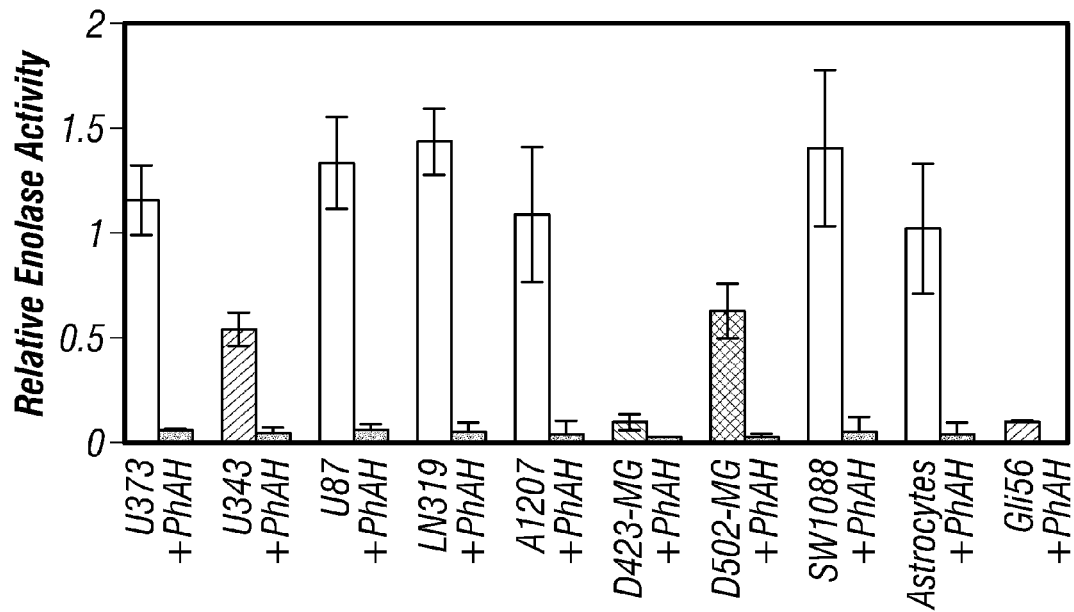
Figure 3C:
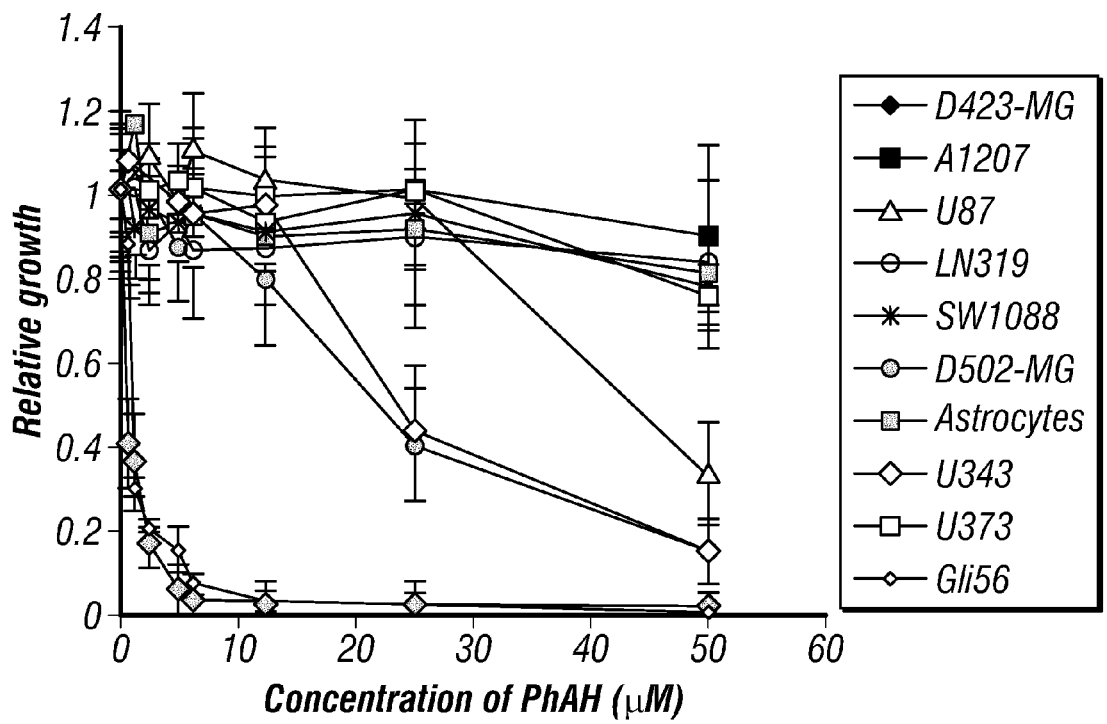
Figure 3D:
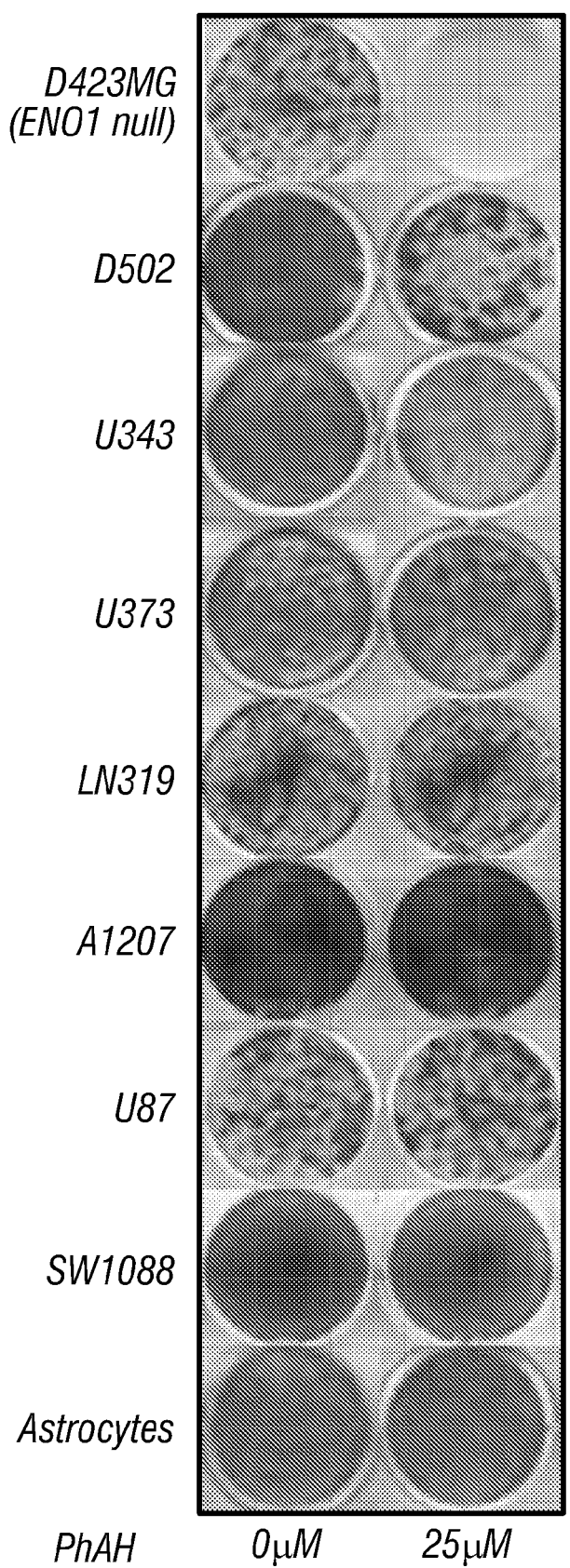
Figure 5A:
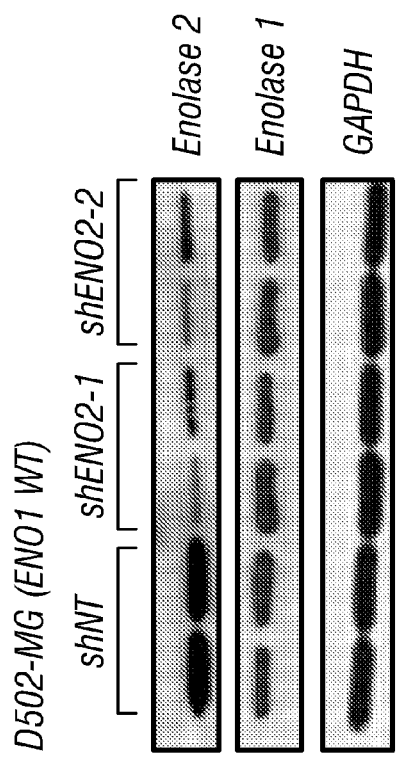
FIGS. 5A-D: Knockdown of ENO2 stalls the growth of ENO1-null GBM cells but does not affect the growth of ENO1 WT GBM cells. a, Two independent hairpins lentivirally delivered through the pLKO.1 vector are effective at reducing enolase 2 protein levels by >80% compared with a non-targeting hairpin (shNT) in D423-MG, an ENO1-null GBM cell line. b, A similar level of ENO2 knockdown is achieved using the same two hairpins in D502-MG, an ENO1 WT GBM cell line. The two hairpins are selective at targeting enolase 2 and do not reduce enolase 1 protein levels. c, Cell proliferation data obtained using a luminescence viability assay for 100 h indicate that knocking down ENO2 using both independent hairpins significantly slows the growth of ENO1-null cells compared with shNT. d, ENO1 WT cells treated with the same hairpins and cultured under the same conditions proliferate at a similar rate with and without ENO2 knockdown.
Figure 5C:
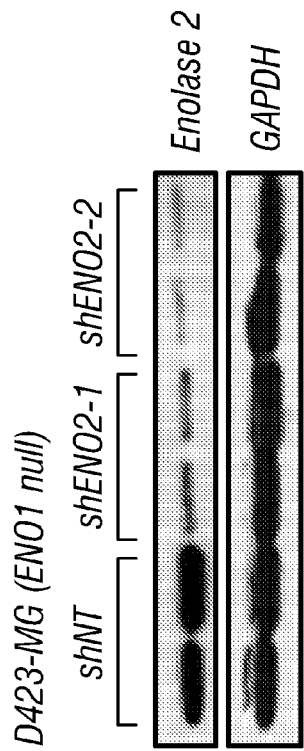
Figure 5B:
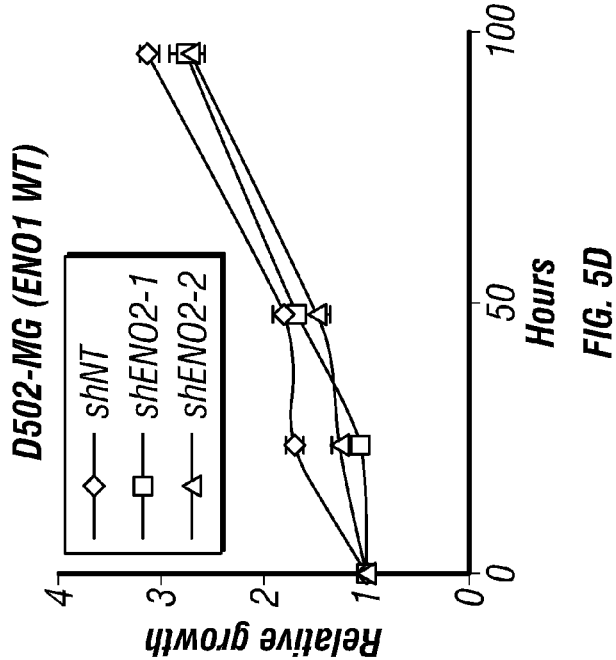
Figure 5D:
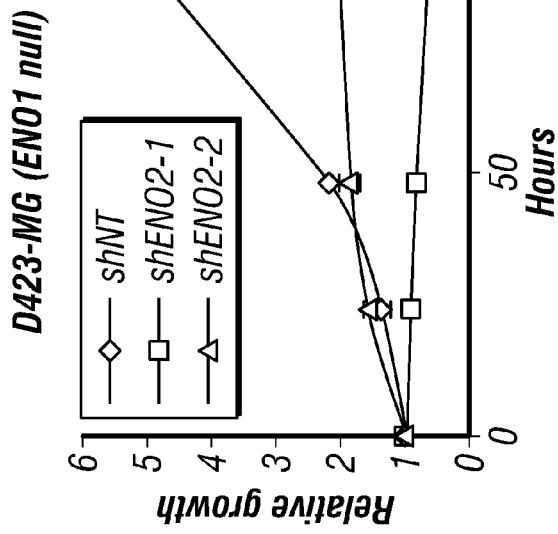
Figure 10:
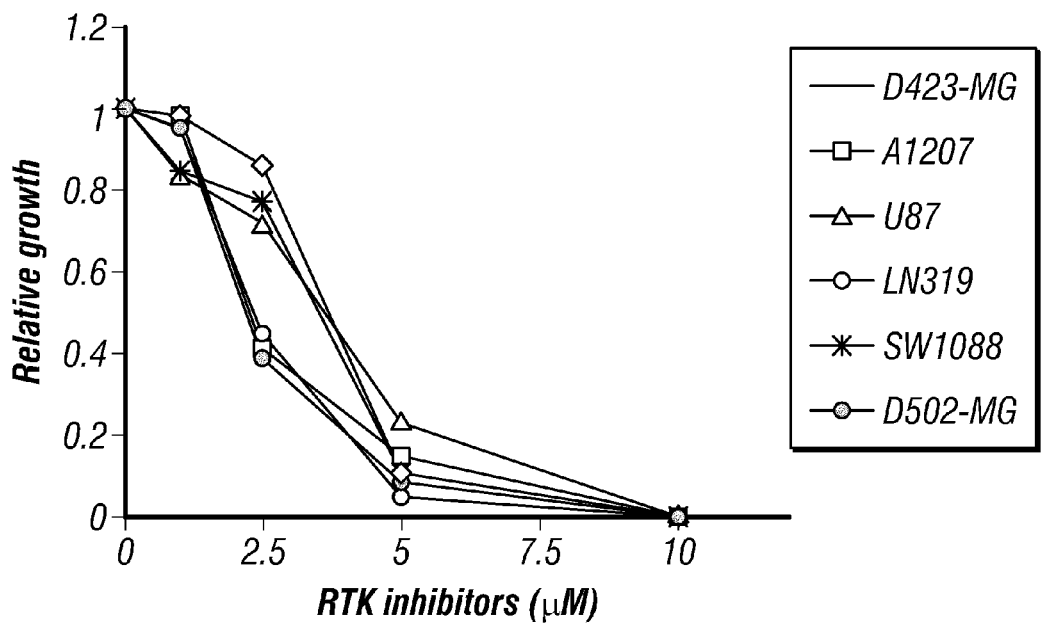
FIG. 10: 1p36 homozygously deleted ENO1-null cells are not sensitive to receptor tyrosine kinase inhibitors. Relative growth of each cell line in the presence of different concentrations of a combination of the receptor tyrosine kinase (RTK) inhibitors sorafenib, lapatinib, and PHA665752 was assayed in parallel with PhAH experiments (FIG. 4). ENO1-null D423-MG cells (red line and markers) were no more sensitive to the combination of RTK inhibitors than were ENO1 WT GBM cell lines.

Next, we assessed the pharmacological impact of inhibition of enolase activity in ENO1 wild type and null cells. Prior studies have focused on the pharmacologic inhibition of enolase, in particular for antibacterial and antiparasitic purposes (Guha-Chowdhury et al., 1997; de, A. S, N. M. V. et al., 2007) and many compounds have been characterized, most of which act as reaction intermediate analogues (Table 4). The most potent enolase inhibitor is the compound phosphonoacetohydroxamate (PhAH; Anderson et al., 1984) which is thought to act as a transition state analogue with an inhibitory constant of 15 pM. While PhAH has not been tested on human enolases, previous work demonstrated inhibitory effects on enolases from distantly related organisms (Anderson et al., 1984; de, A. S, N. M. V. et al., 2007) suggesting its potential use over a large phylogenetic distance. PhAH potently inhibited Enolase in vitro in native lysates of glioma cell lines (FIG. 3b). Employing PhAH in concentrations ranging from 0.625 to 50 µM, we observed significant toxicity in ENO1 null cells (FIG. 3a, c, d) and minimal impact on the ENO1 intact controls which show at least 10-fold greater enolase activity relative to the ENO1 null cells (FIG. 3B; ENO1 is the major Enolase isoform in GBM, accounting for 75 to 90% of cellular Enolase activity; Joseph et al., 1996). Notably, ENO1 null cells do not show any greater sensitivity to other molecular targeted therapies such as receptor tyrosine kinase inhibitors (Stommel et al., 2007) (lapatinib, sorafenib, PHA665752) (FIG. 10). These data indicate that D423-MG cells are not broadly susceptible to other anti-cancer agents and that PhAH selectively targets ENO1 null GBM cells. It is worth noting that D502-MG cells with homozygous deletion of 1p36 yet retention of the ENO1 gene are much more resistant to PhAH than ENO1 null D423-MG cells. In addition, U343 and D502 cells showing intermediate levels of enolase activity show intermediate levels of sensitivity to PhAH, suggesting relative sensitivity to enolase inhibition. Finally, elevating ENO2 activity by re-expressing of hairpin resistant ENO2 completely reversed the PhAH sensitivity of ENO1 null D423-MG cells (FIG. 7).

TABLE 1

| HOMOZY-GOUSLY DELETED GENE | CHROMO-SOMAL LOCUS | TSG | Fraction of cases in GBM TCGA | TARGET HOMO-LOGUE | EXPERI-MENTAL EVIDENCE FOR COMBINED LETHALITY | Pathway | POTENTIAL SMALL MOLECULE INHIBITORS | CELL LINES | Knockout mouse phenotype of target homologue | TCGA GBM case ID with genetic event |
|---|---|---|---|---|---|---|---|---|---|---|
| ENO1 | 1p36.2 | ? | 5/539 | ENO2 | SGD, FB, WB | Glycolysis and Gluconeo-genesis | Phosphonoaceto-hydroxamate | Gli56, H423-MG, H527-MG, H892-MG | Viable & Fertile | 06-0137, 06-0879, 02-0290, 08-0531, 12-0656 |
| H6PD | 1p36.2 | ? | 5/359 | G6PD | No | Pentose Phosphate Shunt | Dehydroepian-drosterone | Gli56, H423- MG, H527-MG, H892-MG | NA | 06-0137, 06-0879, 02-0290, 08-0531, 08-0375 |
| KIF1B | 1p36.2 | ? | 1/359 | KIF1A/C | No | Chromosomal Seggregation | "Drugable" | NB1 | Post natal lethal/Viable | 06-0879 |
| NMNAT1 | 1p36.2 | ? | 2/359 | NMNAT2/3 | SGD | NAD+ Biosynthesis | Np3AD, Np4AD, and Nap4AD | Gli56, H527-MG | NA | 06-0879, 06-0137 |
| UBE4B | 1p36.2 | ? | 2/359 | UBE4A | No | Polyubiquitin dependent degradation | NA | Gli56, H527-MG, NB1 | NA | 06-0879, 06-0137 |
| ACO1 | 9p21.1 | INK/ARF | 2/359 | ACO2/ACO3 | SGD, MGI | Regulation of Iron Metabolism/ Citric acid cycle | Fluorocitrate | TS561 | NA/late-age neuro-degeneration | 06-0127, 06-1802 |
| KLHL9 | 9p22 | INK/ARF | 56/359 | KLHL13 | No | Chromosomal segregation | Not "Drugable" | Several established lines, e.g SW1088 | NA | 06-0148, 02-290, 06-125 and many others |

TABLE 1-continued

| HOMOZY-GOUSLY DELETED GENE | CHROMO-SOMAL LOCUS | TSG | Fraction of cases in GBM TCGA | TARGET HOMO-LOGUE | EXPERI-MENTAL EVIDENCE FOR COMBINED LETHALITY | Pathway | POTENTIAL SMALL MOLECULE INHIBITORS | CELL LINES | Knockout mouse phenotype of target homologue | TCGA GBM case ID with genetic event |
|---|---|---|---|---|---|---|---|---|---|---|
| PANK1 | 10q23.31 | PTEN | 5/359 | PANK3 | FB, SGD, WB | Acetyl-CoA Biosynthesis | Hopantenate | TB673, TB637, TB/TS586 | Viable & Fertile | 06-1087, 14-1825, 19-1786, 08-0386, 19-0963 |
| KIF20B | 10q23.31 | PTEN | 5/359 | KIF20A | FB | Chromosomal segregation/cytokinesis | Paprotrain | TB673, TB637, TB/TS586 | NA | 06-1087, 14-1825, 19-0963, 08-0386, 19-1786 |

TABLE 2

Distribution and loss-of-function phenotypes of ENO homologues.

| | Location | Expression | Knockout mouse phenotype | Associated Human Genetic Disease |
|---|---|---|---|---|
| ENO1 | 1p36 | Ubiquitous | Lethal E10 | Hemolytic Anemia |
| ENO2 | 12p13 | CNS | Viable, Fertile | None Described |
| ENO3 | 17p11 | Muscle | N/A | Glycogen storage disorder |

TABLE 4

General properties of known enolase inhibitors.

| Inhibitor | Ki (M) | Mode of action |
|---|---|---|
| D-tartronate semialdehyde phosphate | $10^{-5}$ | Substrate analogue, competitive inhibitor |
| 3-aminoenolpyruvate-2-phosphate | $10^{-7}$ | Substrate analogue, competitive inhibitor |
| Phosphonoacetohydroxamate | $1.5 \times 10^{-11}$ | Intermediate analogue |
| 2-fluoro-2-phosphonoacetohydroxamate | N/A | Intermediate analogue |

TABLE 3

| Deleted gene | Affected pathway | Possible synergistic agents | Affected pathway | Reason |
|---|---|---|---|---|
| ENO1 | Glycolysis and Gluconeogenesis | Nucleotide analogues (cytarabine, 5-FU, gemcitabine, mercaptopurine, tioguanine) Anthracyclines (e.g. doxorubicin) | Nucleic acid synthesis | Glycolytic intermediates used for nucleic acid synthesis |
| | | Other antiglycolytics (e.g. 3-bromopyruvate, 2-DG, lonidamide) | Glycolysis | Synergistic effect on glycolysis |
| | | Mitochondrial Respiratory Inhibitors (Antimycin A, Oligomycin, Rotenone) | Mitochondrial Respiratory Chain | Combined inhibition of the two major energy generating pathways in the cell |
| H6PD | Pentose Phosphate Shunt | Nucleotide analogues (cytarabine, 5-FU, gemcitabine, mercaptopurine, tioguanine) Anthracyclines (e.g. doxorubicin) | Nucleic acid synthesis | PPP is essential for synthesis of sugars for nucleic acids |
| KIF1B | Chromosomal Segregation | Vinca alkaloids (vincristine, vinblastine) | Microtubule assembly | Both act on cell division pathway |
| | | Paclitaxel, docetaxel | Block microtubule disassembly | |
| NMNAT1 | NAD+ Biosynthesis | FK 866 | NAD+ Biosynthesis inhibitor | Synergistic effects on NAD+ biosynthesis |
| UBE4B | Polyubiquitin dependent degradation | Proteosome inhibitors (Bortezomid) | Ubiquitin dependent protein degradation | Both act to prevent proper protein degradation |
| ACO1 | Regulation of Iron Metabolism/Citric acid cycle | | | |
| KLHL9 | Chromosomal segregation | Vinca alkaloids (vincristine, vinblastine) | Microtubule assembly | Both act on cell division pathway |
| | | Paclitaxel, docetaxel | Block microtubule disassembly | |
| PANK1 | Acetyl-CoA Biosynthesis | Fatty acid synthase inhibitors | Synthesis of Lipids and Fatty acids | Synergistic inhibitory effect on fatty acid biosynthesis |
| KIF20B | Chromosomal segregation/cytokinesis | Vinca alkaloids (vincristine, vinblastine) | Microtubule assembly | Both act on cell division pathway |
| | | Paclitaxel, docetaxel | Block microtubule disassembly | |

TABLE 4-continued

General properties of known enolase inhibitors.

| Inhibitor | Ki (M) | Mode of action |
|---|---|---|
| (3-hydroxy-2-nitropropyl)phosphonate | $10^{-9}$ | Intermediate analogue |
| (nitroethyl)phosphonate | $10^{-6}$ | Intermediate analogue |
| d-(phosphonoethyl)nitrolate | $1.4 \times 10^{-8}$ | Intermediate analogue |
| Fluoride | Varied depending on other ion concentrations | Inhibits subunit cooperativity |

Example 3

Deletion of ENO1 Renders Cells Susceptible to Glycolysis Inhibitors

Cancer genomes are characterized by numerous copy number amplifications and deletions, which target driver oncogenes and tumor suppressor genes, respectively. Often, these genomic alterations are large regional events, affecting many other genes in addition to the intended target(s). The fact that such broad genomic alterations are not negatively selected against in cancer cells implies that, on their own, the copy number alterations of these neighboring passengers must not carry any detrimental biological consequence. That said, it is conceivable that these passenger genomic events can create unintended (collateral) vulnerabilities unique to those cells; such as when a passenger being co-deleted is a member of a redundant multi-gene family serving an essential housekeeping function. A large body of genetic interaction studies in invertebrates as well as mice indicates that many essential cellular housekeeping functions are carried out by multiple homologous genes that encode overlapping functions; this redundancy enables cell viability upon loss of one homologue but causes lethality upon loss of multiple homologues (Vavouri et al., 2008; Costanzo et al., 2008; Deutscher et al., 2006). In this conceptual framework, it was hypothesized that the homozygous deletion of redundant essential housekeeping genes could create cancer-specific vulnerabilities whereby pharmacological inactivation of the second, non-deleted homologue would result in complete loss of activity in tumor cells carrying the deletion, without compromising the health of normal cells, in which both genes are intact and expressed.

By examining the Cancer Genome Atlas (TCGA) GBM data set for homozygous deletions targeting genes involved in essential cell activities (Cancer Genome Atlas Research Network, 2008), the ENO1 gene was identified as a candidate, which resides at the 1p36 tumor suppressor locus. Enolase, which is encoded by three homologous genes, is an essential enzyme that catalyzes the second to last step of glycolysis, converting 2-phosphoglyceric acid into phosphoenolpyruvate. In mammals, enolase activity is encoded by three genes: ENO1, which is ubiquitously expressed (Joseph et al., 1996; Stefanini, 1972); ENO2, which is expressed exclusively in neural tissues (Joseph et al., 1996; Kobayakawa et al., 2007); and ENO3, which is expressed in muscle tissues (Comi et al., 2001). ENO1 is the major enolase isoform in GBM, accounting for 75-90% of cellular enolase activity (Joseph et al., 1996). Given the critical importance of glycolysis for energy generation and anabolic processes in normal and especially tumor cells (Wise and Thompson, 2010), GBM tumors homozygous null for ENO1 would be predicted to be highly sensitive to inhibition of enolase 2, whereas normal neural tissues should not be affected because of the functional redundancy of enolase 1. Correspondingly, ENO2 knockout mice are viable and fertile, suggesting that pharmacological inhibition of enolase 2 is likely to be well tolerated at the organism level. Moreover, Saccharomyces cerevisiae, which possesses several enolase homologues, shows weak phenotypes with single mutants and incurs cell lethality only when all homologues are deleted (Costanzo et al., 2008; Deutscher et al., 2006); whereas, Caenorhabditis elegans and Drosophila possess only one gene encoding enolase activity, and its deletion is lethal (Sonnichsen et al., 2005).

The 1p36 locus, which contains several candidate tumor suppressor genes (Bagchi and Mills, 2008), sustains frequent deletion in GBM (FIG. 1a) (Joseph et al., 1996). The 1p36 locus is homozygously deleted in 1-5% of GBMs (Cancer Genome Atlas Research Network, 2008; Duncan et al., 2010) (as well as oligodendrogliomas (Kotliarov et al., 2006) and large-cell neuroendocrine lung tumors (Peng et al., 2005)) and ENO1 is often included in the deletion. By examining the TCGA copy number aberrations (single nucleotide polymorphism [SNP] and array comparative genomic hybridization [aCGH] data) (Cancer Genome Atlas Research Network, 2008) and expression profiles, 5/359 GBM samples were identified with homozygous deletion of ENO1 and associated near-complete absence of its expression (FIG. 1b and FIG. 4). Two GBM cell lines, D423-MG (Duncan et al., 2010) and Gli56 (Mueller et al., 2007), were identified with homozygous deletions at the 1p36 locus spanning ENO1. A third GBM cell line, D502-MG (Duncan et al., 2010), also incurs homozygous deletion of many genes in this locus yet leaves ENO1 intact and thus serves as an excellent control (FIG. 1c). Western blot analysis confirmed the loss of enolase 1 and the retention of enolase 2 protein in D423-MG and Gli56, whereas both proteins were present in D502-MG and in all other glioma and normal glial cell lines tested (FIG. 1d).

Figure 6A:
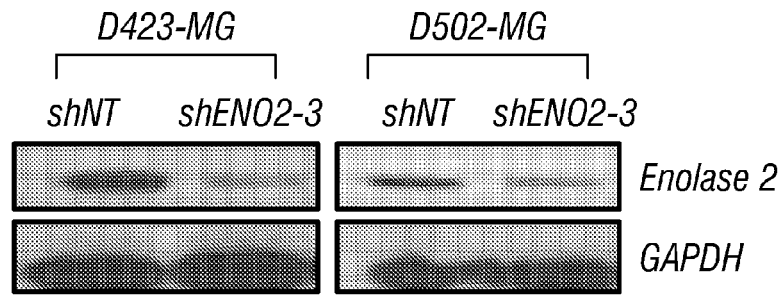
FIGS. 6A-C: Knockdown of ENO2 stalls the growth of ENO1-null GBM cells and decreases both in vitro and in vivo tumorigenic potential. a, A hairpin that was lentivirally delivered through the pGIPZ vector (shENO2-3) reduced the expression of ENO2 by >70% compared with a non-targeting hairpin (shNT) in the cell lines D423-MG (ENO1-null) and D502-MG (ENO1 WT). b, Cell proliferation was dramatically slowed only in the context of ENO1 genomic deletion. c, Soft agar colony formation (c) and in vivo tumorigenic properties were also dramatically decreased in D423-MG ENO1-null cells by shENO2-3 as compared with shNT. No soft agar colony formation or in vivo tumorigenic properties could be collected for ENO2 ablation in D502-MG cells because the parent cell line was unable to form soft agar colonies or intracranial tumors.
Figure 6B:
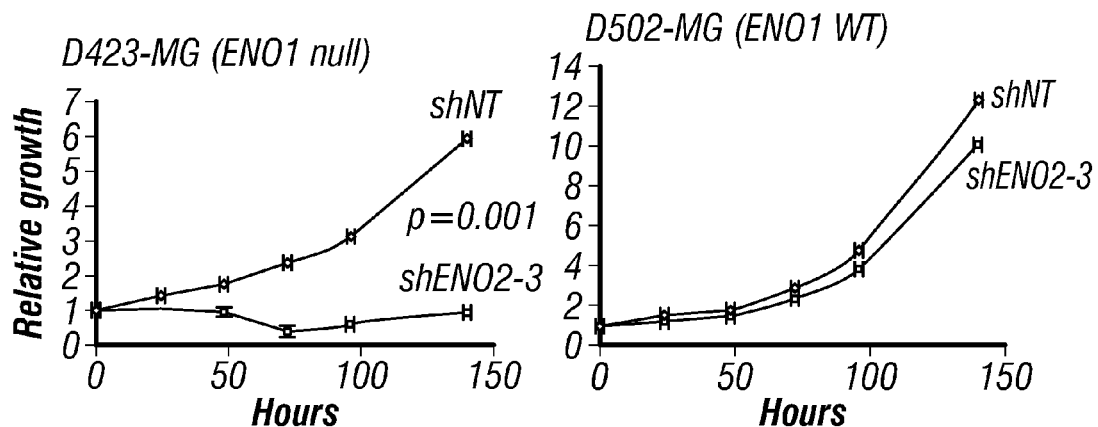
Figure 6C:
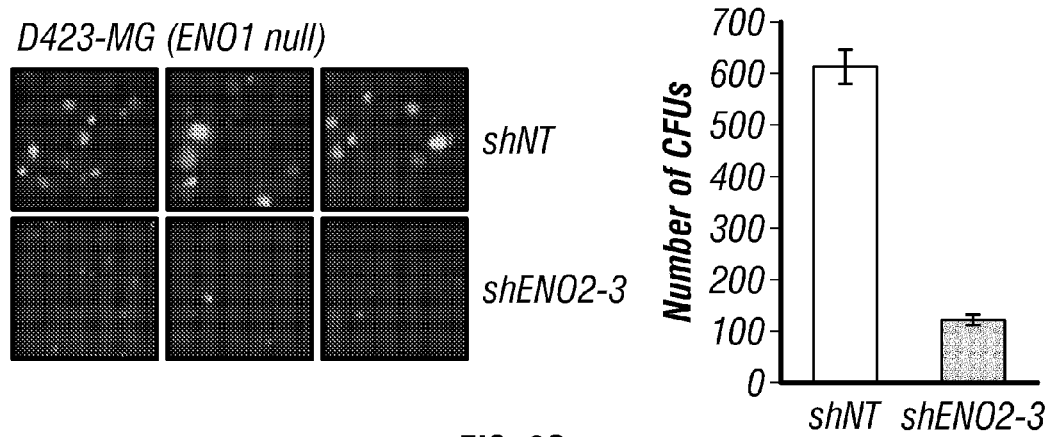
Figure 8A:
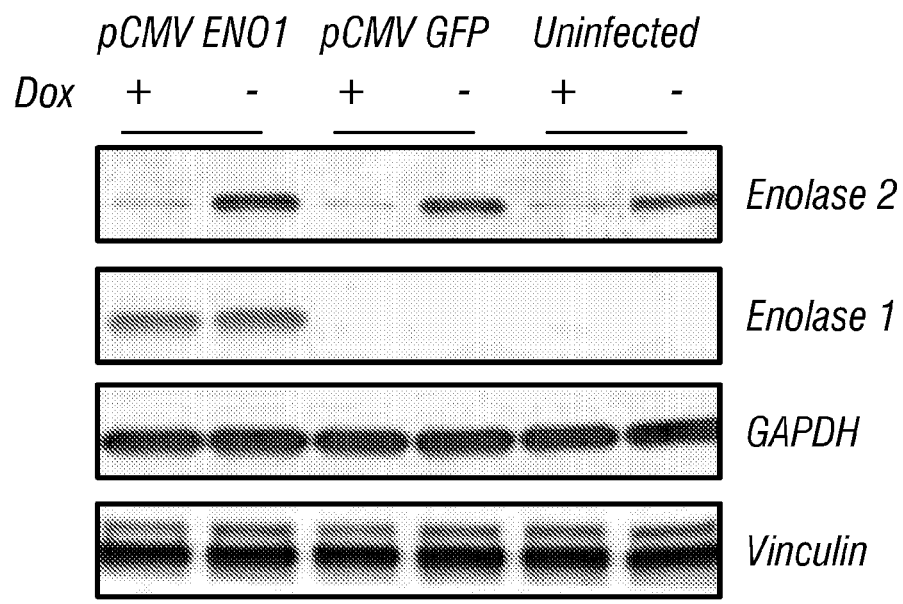
FIGS. 8A-C: Ectopic expression of enolase 1 in ENO1 null cell line D423-MG prevents the toxic effects of enolase 2 knock down. a, pCMV lentiviral constructs expressing ENO1 or GFP were used to infect D423-MG cells already expressing two pTRIPZ doxycycline inducible shRNAs targeting enolase 2 (shENO2-3+4). Doxycycline induction of shENO2-3+4 led to a decrease in enolase 2 protein levels of approximately 80%. b, c, Ectopic expression of ENO1 but not GFP prevents the toxic effects caused by doxycycline-mediated induction of the shRNAs. b, crystal violet stains of saturated plates with each treatment group in quadruplicate. c, IncuCyte live growth curves showing average confluence (quadruplicates +/−S.E.M.).
Figure 8B:
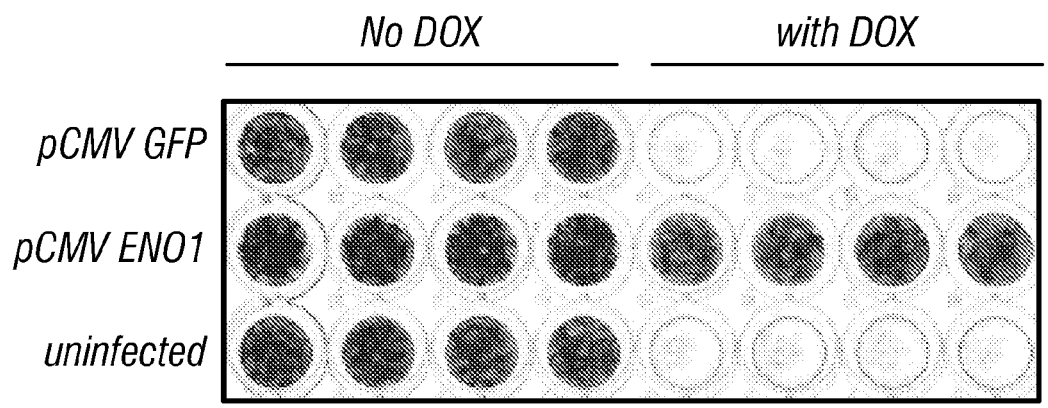
Figure 8C:
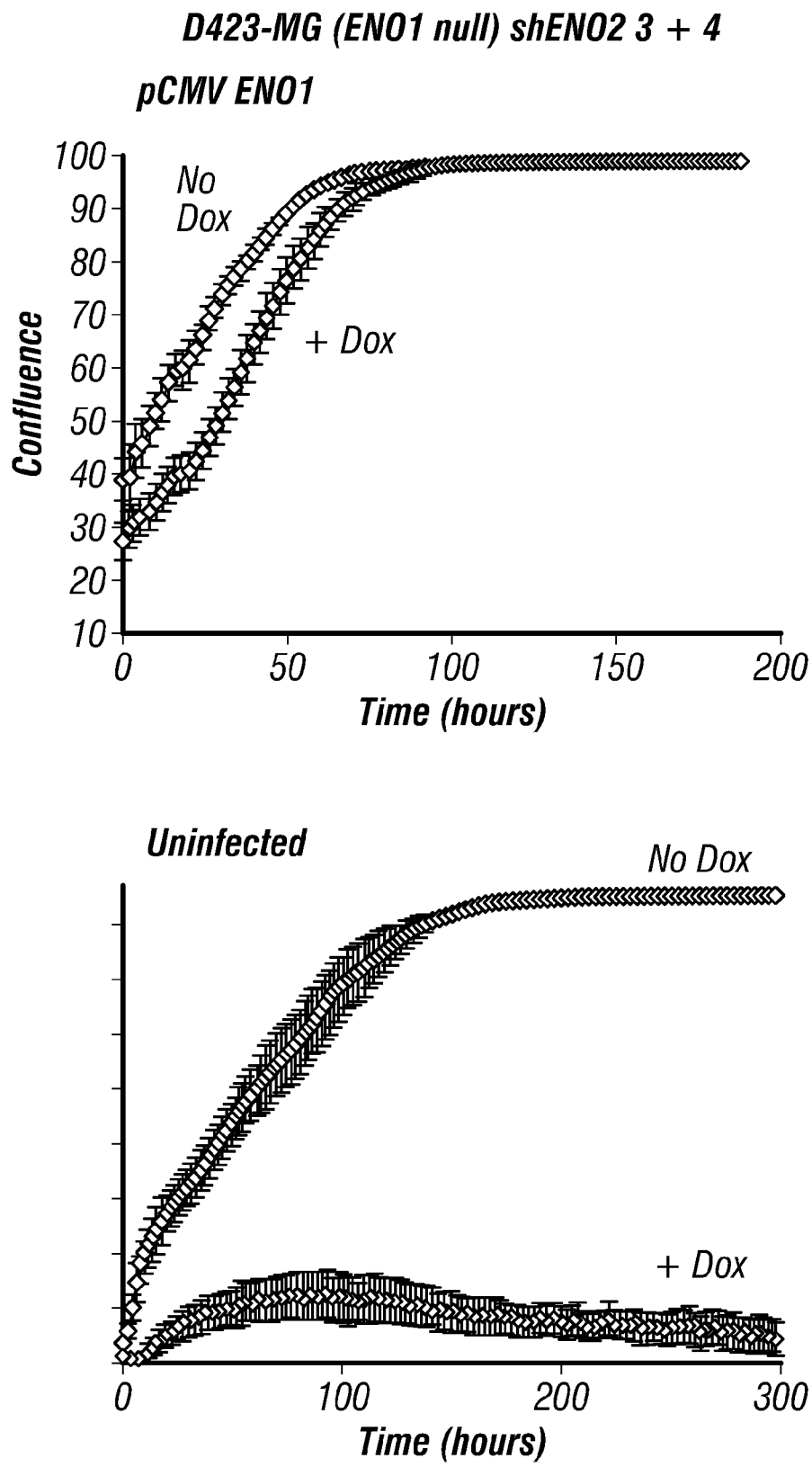
Figure 8C:
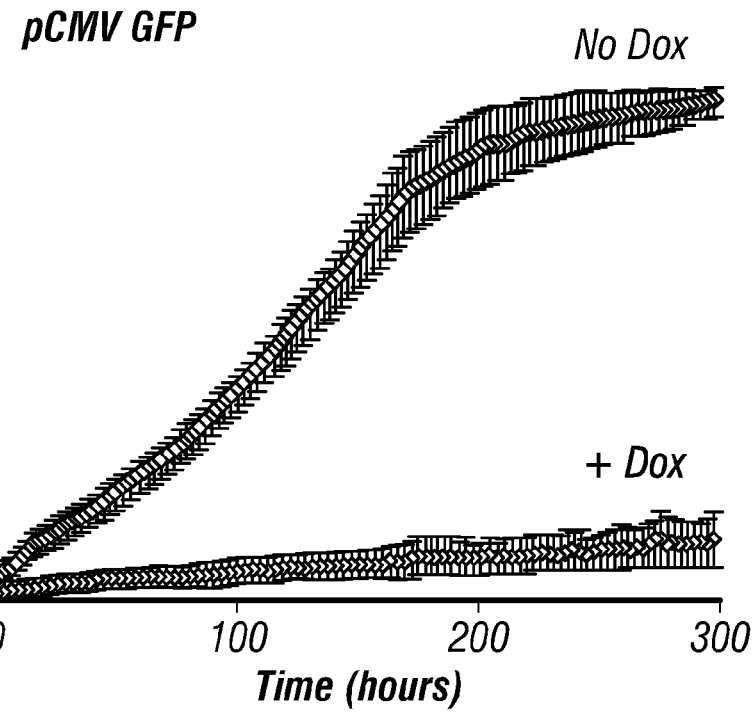
Figure 9A:
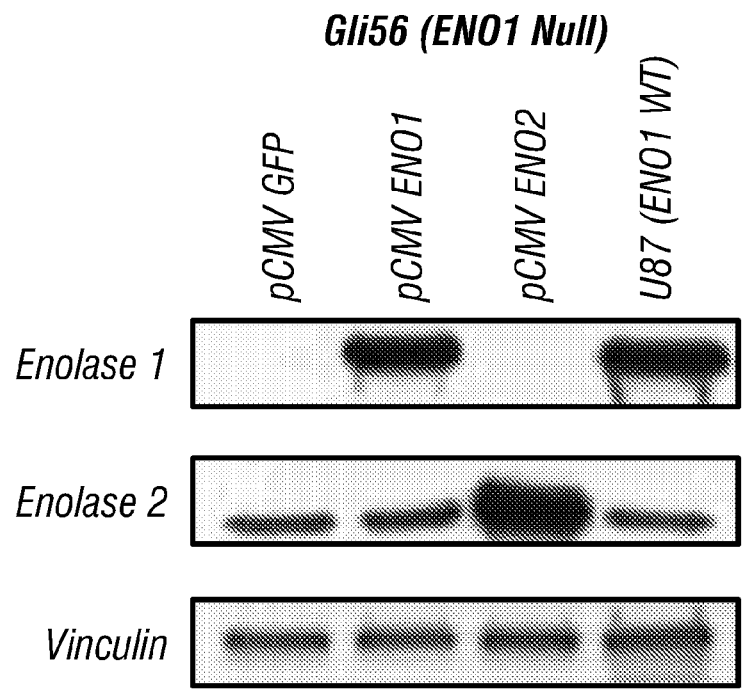
FIGS. 9A-D: Dose-dependent rescue of PhAH toxicity by ectopic expression of ENO1 and ENO2 in ENO1-null cell lines. a, Gli56 ENO1-null cells were infected with pCMV lentiviral constructs contain GFP, ENO1 or ENO2 which yielded ENO1 expression comparable to levels shown in GBM lines (U87) and strong overexpression of ENO2. b, Expression of enolase 1 and overexpression of enolase 2 significantly protected Gli56 cells from the deleterious effects of PhAH. c, The same experiment was performed in D423-MG ENO1-null line, with varying levels of viral titer. Six different titers of pCMV ENO1 and two different titers of pCMV ENO2 yielded graded levels of enolase expression and activity. d, Introduction of enolase 1 protected these cells from the toxic effects of PhAH and the concentration of inhibitor required to achieve lethality (after 14 days incubation) increased directly in proportion with the level of enolase 1 expression and enzymatic activity. The same pattern was obtained for the 2 levels of enolase 2 overexpression.
Figure 9B:
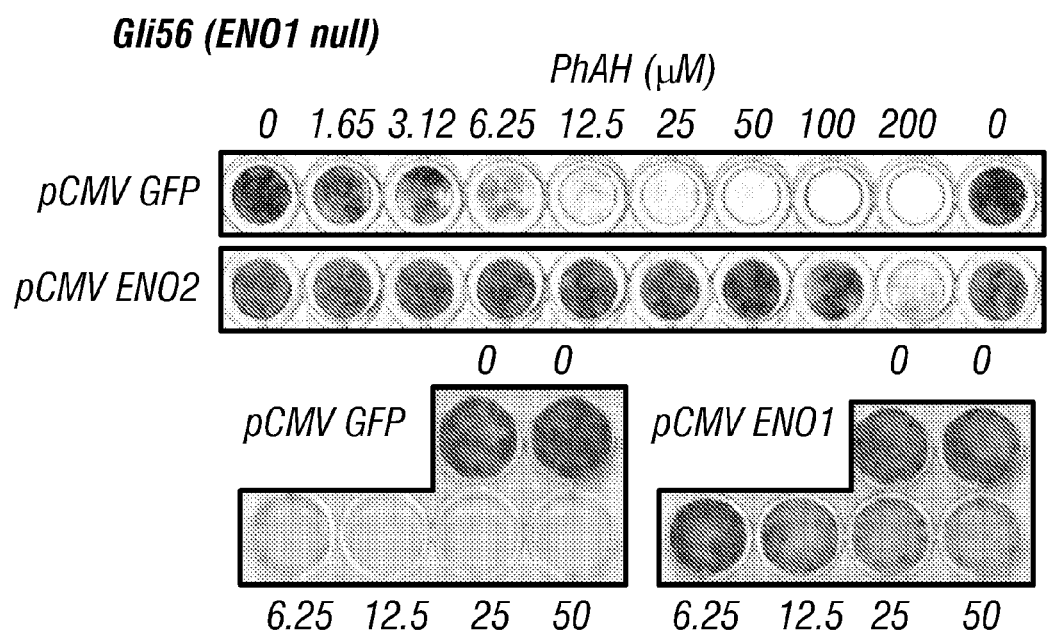
Figure 9C:
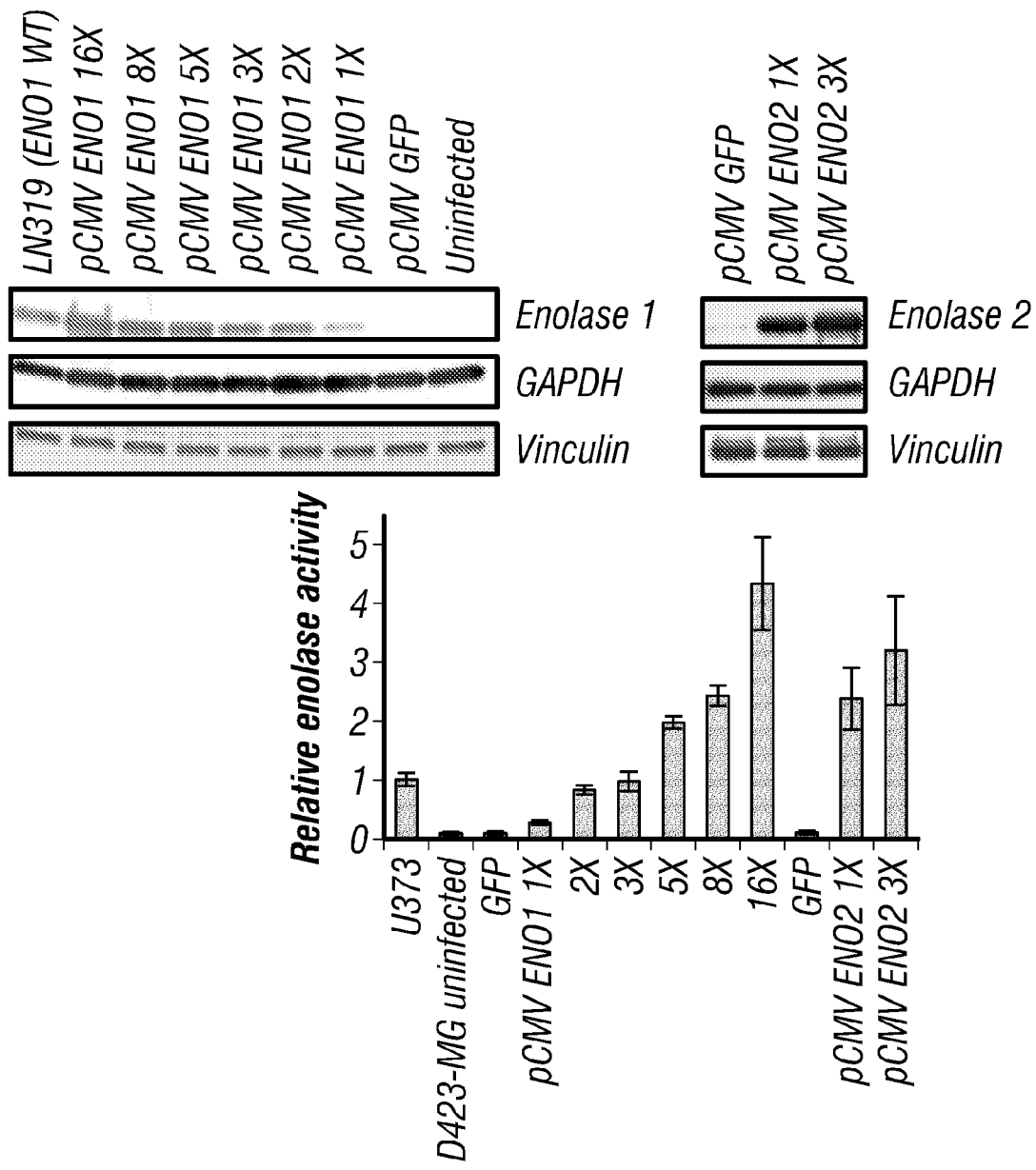
Figure 9D:
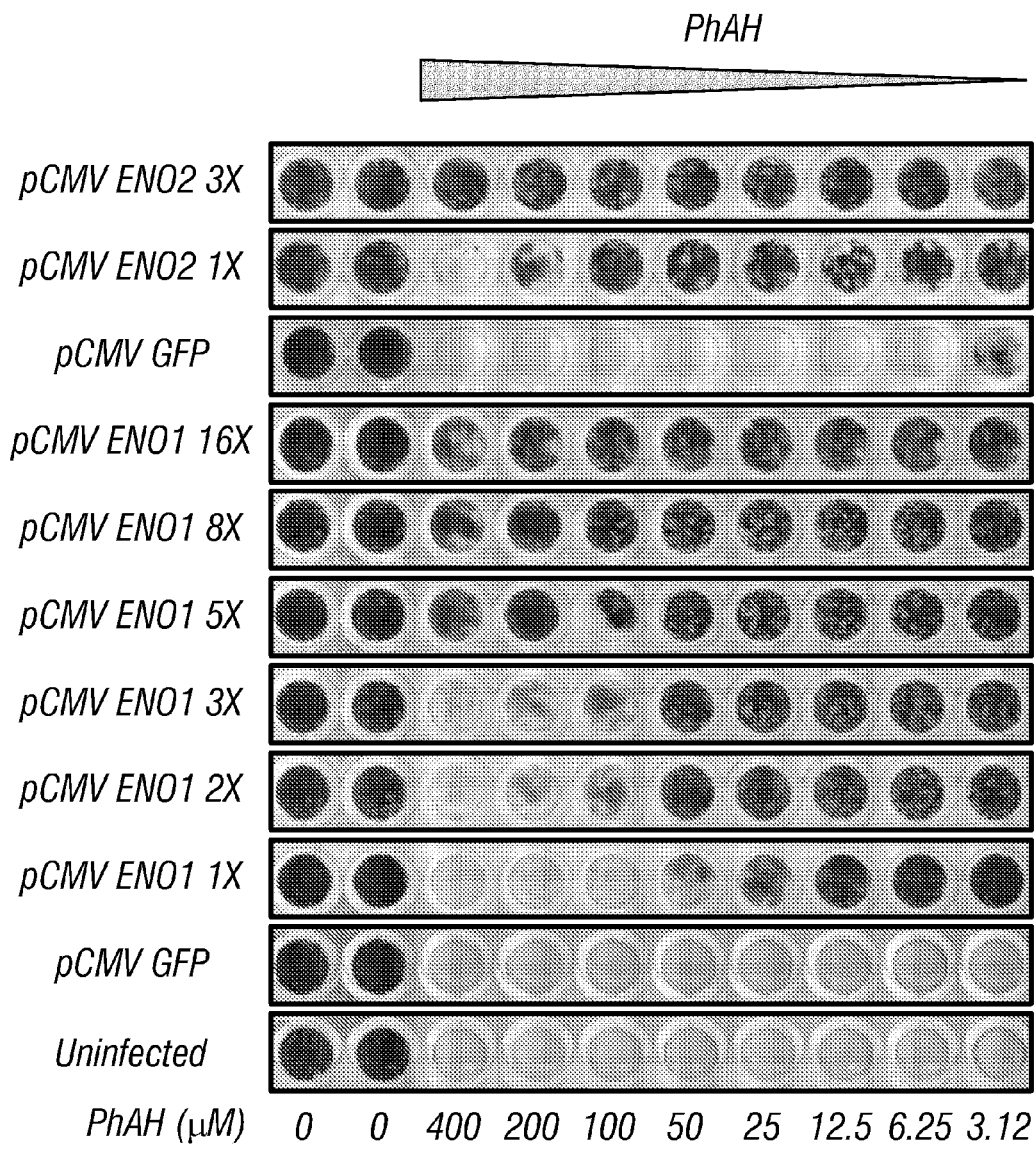

The D502-MG (ENO1 wild-type [WT]) and D423-MG (ENO1-null) cell lineswere used to assess the impact of shRNA-mediated knockdown of ENO2 in an ENO1 WT or null context. Two independent ENO2 shRNAs (pLKO.1 vector) resulted in robust protein reduction and led to a profound inhibition of cell growth only in the context of ENO1 genomic deletion (FIG. 5). The same result was obtained using an additional, independent ENO2 shRNA (pGIPZ vector) (FIG. 6a,b). Furthermore, shRNA ablation of ENO2 in ENO1-null cells also resulted in decreased soft agar colony formation and blocked the in vivo tumorigenic potential of intracranially injected cells (FIG. 1e and FIG. 6c). Finally, the selective toxicity of ENO2 ablation to ENO1-null cells was demonstrated in an isogenic context using the doxycycline-inducible TRIPZ vector. When this doxycycline-inducible system was used in ENO1 WT cell lines (U87, A1207, LN319), two independent shRNAs reduced enolase 2 protein levels by >70% (FIG. 2a) with no impact on enolase 1 levels (data not shown). This ablation of ENO2 resulted in a profound inhibition of cell proliferation only in the ENO1-null D423-MG cell line (FIG. 2b). Furthermore, enforced expression of hairpin-resistant ENO2 cDNA fully reversed the deleterious effects of the shENO2 hairpin (FIG. 7), showing that the inhibitory effect of the hairpin was indeed specific to diminished ENO2 expression and was not an off-target effect. Finally, when ENO1 was ectopically re-expressed in D423-MG (ENO1 null) cell lines at levels similar to those observed in ENO1-WT GBM lines, the deleterious effect of shRNA ablation of ENO2 was completely abrogated (FIG. 8).

Next, the impact of pharmacological inhibition of enolase activity was assessed in ENO1 WT and null cells. Previous studies have focused on the pharmacological inhibition of enolase, in particular for antiparasitic purposes (Navarro et al., 2007) and many compounds have been characterized, most of which act as reaction-intermediate analogues (Table 5).

TABLE 5

General properties of published enolase inhibitors. A large panel of pan-enolase inhibitors has been synthesized in the past as tool to study the mechanism of the enzyme, with PhAH showing the most potency. Most inhibitors are thought to act as transition state analogues, showing intermediate configurations of the reactant (2-phosphoglycerate) and the product (phosphoenolpyruvate). It should be noted that the effective IC50 of these inhibitors are lower than these listed in the table since it is the ionized forms that act as inhibitors and the pKas vary from 8 to 12. For PhAH, the pKa is 10.2, such that at physiological pH, the IC50 is expected to be around 15 nM (Navarro et al., 2007).

| Inhibitor | Ki (M) | pKa | Mode of action | Ref. |
|---|---|---|---|---|
| D-tartronate semialdehyde phosphate | $10^{-5}$ | pH independent | Substrate analogue, competitive inhibitor | Hill et al., 2000 |
| 3-aminoenolpyruvate-2-phosphate | $10^{-7}$ | N/A | Substrate analogue, competitive inhibitor | Hill et al., 2000 |
| Phosphonoacetohydroxamate | $1.5 \times 10^{-11}$ | 10.2 | Intermediate analogue | Hill et al., 2000, Moore et al., 1994 |
| 2-fluoro-2-phosphonoacetohydroxamate | $1.4 \times 10^{-6}$ | 8.1 | Intermediate analogue | Moore et al., 1994 |
| (3-hydroxy-2-nitropropyl)phosphonate | $6 \times 10^{-9}$ | 8.1 | Intermediate analogue | Hill et al., 2000 |
| (nitroethyl)phosphonate | $10^{-6}$ | 8.5 | Intermediate analogue | Hill et al., 2000 |
| d-(phosphonoethyl)nitrolate | $1.4 \times 10^{-8}$ | N/A | Intermediate analogue | Hill et al., 2000 |
| Fluoride | Varied depending on other ion concentrations | | Inhibits subunit cooperativity | Smith et al., 2006 |

The most potent enolase inhibitor is PhAH (Anderson et al., 1984), which is thought to act as a transition-state analogue with an inhibitory constant of 15 pM on yeast enolase. Although PhAH has not been tested on human enolases, previous work demonstrated inhibitory effects on enolases from distantly related organisms (Navarro et al. 2007; Anderson et al., 1984; Duncan et al., 2010) suggesting its potential use over a large phylogenetic distance. PhAH was indeed capable of potent inhibition of enolase in vitro in native lysates of human GBM cell lines, with an $IC_{50}$ of around 20 nM (FIG. 3b). PhAH was used in concentrations ranging from 0.625 µM to 50 µM and observed marked toxicity in ENO1-null cells (FIG. 3a, c, d and FIG. 9) and minimal impact on the ENO1-WT controls, which show at least 10-times greater enolase activity relative to the ENO1-null cells (because ENO1 accounts for 90% of total cellular enolase activity (Joseph et al., 1996), FIG. 3b). Although the IC50 of PhAH is similar for ENO1 and ENO2 in vitro (data not shown) the greater toxicity of the inhibitor to ENO1 null cells (Gli56, D423-MG) derives from the fact that in these cells enolase activity is already 90% lower (in effect, 90% "pre-inhibited") as compared to ENO1-WT cell lines and consequently, a much lower dose is required to decrease total enolase activity below toxicity threshold. Further data indicate a direct relationship between the levels of enolase activity and the sensitivity to PhAH across different cell lines and in the same cell line with different levels of enforced enolase expression. First, U343 and D502-MG cells, which have intermediate levels of enolase activity (and enolase 1 protein expression, FIG. 1d) compared with the other cell lines, have intermediate levels of sensitivity to PhAH (FIG. 3), which in the case of U343 can be rescued by ectopic overexpression of ENO1 or ENO2 (data not shown). A systematic titration of PhAH in D423-MG cell lines with varying levels of enforced ENO1 or ENO2 expression, shows a direct relationship between the level of enolase expression/activity and the ensuing resistance to PhAH (FIG. 9). PhAH toxicity was also abrogated in Gli56 ENO1-null cells by ectopic expression of physiological levels of ENO1 or overexpression of ENO2 (FIG. 9). Regarding the mechanism of toxicity, cell cycle and apoptosis analysis demonstrated that PhAH treatment for 48 h induced a marked decrease of S-phase followed by a marked increase of apoptosis in D423-MG but not in ENO1 WT U373 cells. This effect was completely rescued by ENO2 overexpression. The fact that this growth inhibition and subsequent apoptosis is due to energy crisis is substantiated by a strong induction of phosphorylated AMPK (Thr172), which was observed in D423-MG but not ENO1 WT cell lines (data not shown). It is tempting to speculate that this energy stress response exerts a protective effect and thus concomitant addition of an AMPK inhibitor with PhAH would result in further toxicity. Finally, it is worth noting that ENO1-null cells do not show any greater sensitivity to other molecular targeted therapies, such as a combination of receptor tyrosine kinase inhibitors (Stomme et al., 2007) (lapatinib, sorafenib, and PHA665752) (FIG. 10) and rapamycin compared to ENO1 WT cells. These data indicate that D423-MG cells are not broadly susceptible to other anticancer agents and that PhAH selectively targets ENO1-null GBM cells.

Together, these genetic and pharmacological results demonstrate that enolase 2 inhibition is lethal in cells with 1p36 homozygous deletion with collateral loss of ENO1, whereas ENO1-intact cells can rely on enolase 1 to undergo glycolysis and support survival. These findings are in agreement with genetic data from invertebrates (Costanzo et al., 2008; Deutscher et al., 2006). Given that several homozygously deleted housekeeping genes can occur in the same deletion on 1p36 (e.g., H6PD), it may be possible to further increase the effectiveness and cancer-cell-specific killing by combining the inhibition of ENO2 with that of another homologue of a simultaneously deleted housekeeping gene.

Furthermore, the studies show that cells, such as U343, which are heterozygous at the ENO1 locus, are more sensitive to toxicity by an enolase inhibitor such as phosphonoacetohydroxamate than wild type glioblastoma cell lines and normal astrocytes. FIGS. 1, 3 and 11 highlight these data. FIG. 1d shows that both the D502-MG and U343 cells show reduce expression of enolase 1 corresponding to a heterozygous deletion of ENO1. As shown by the dose response studies in FIGS. 3 and 11 these cells are significantly more sensitive to the toxic effects of PhAH than the wild type cell lines. This effect was found to be partially reversible by overexpression of ENO1 or ENO2 in the cells. Interesting the heterozygous cells were also further sensitized to the effects of PhAH by treatment with oligomycin. Accordingly, ENO1 heterzygous cancer cells are promising targets for glycolysis inhibitor-based therapies.

Example 4

Materials and Methods for Example 3

Cells were cultured using standard techniques in Dulbecco Modified Eagle's Medium with 20% fetal bovine serum. shRNA experiments were conducted by lentiviral production through transient transfection of 293T cells followed by transduction in medium containing 4 µg/mL polybrene and selection with 2 µg/mL puromycin. shRNA expression was induced with 1 µg/mL doxycycline and knock down was tested by western blot. The shRNA-resistant ENO2 clone was created by introducing silent mutations with the QuickChange site directed mutagenesis kit from Stratagene and then cloning into the pHAGE-CMV lentiviral vector. Cell proliferation experiments were performed using crystal violet staining, the CellTiter-Glo assay (Roche) and by measuring confluence using IncuCyte (Essen Bioscience). Orthotopic intracranial injections of D-423MG cells with and without ENO2 knockdown in SCID mice were performed as previously described (Zheng et al., 2008). Soft agar colony formation assay of the above cells was performed using standard technique by seeding $10^4$ cells in 6 well plates. For the inhibitor studies, PhAH lithium salt was custom synthesized by TCRS, following the protocol of Anderson et al. (1984). For the enolase activity assay, NADH oxidation was measured in a pyruvate kinase-lactate dehydrogenase coupled reaction as previously described (Joseph et al., 1996). For cell cycle studies, cells were incubated with or without PhAH for 48 hours, stained with propidium iodide and sorted via flow cytometric analysis. For Annexin V/7-AAD assay cells were treated with or without PhAH for 96 hours, stained with Annexin V-PE and 7-AAD, and evaluated for apoptosis by flow cytometry according to the manufacturer's protocol (Biovision).

Cell Culture

The cell lines D423-MG is 1p36 homozygously deleted, including ENO1 and D502-MG is 1p36 homozygously deleted, excluding ENO1 (Duncan et al., 2010). Cells D423 and D502 are referred to as H423 and H502 in Duncan et al. but as D423-MG and D502-MG in the Wellcome Trust Sanger Institute database, the nomenclature adopted here (on the world wide web at sanger.ac.uk). Gli56 was described in Mueller et al. (2007). The deletion in D423-MG spans the CAMTA1, VAMP3, PER3, UTS2, TNFRSF9, PARK7, ERRFI1, SLC45A1, RERE, ENO1, CA6, SLC2A5, GPR157, MIR34A, H6PD, SPSB1, and SLC25A33 genes while the deletion in Gli56 spans the UTS2, TNFRSF9, PARK7, ERRFI1, SLC45A1, RERE, ENO1, CA6, SLC2A5, GPR157, MIR34A, H6PD, SPSB1, SLC25A33, TMEM201, C1orf200, PIK3CD, CLSTN1, CTNNBIP1, LZIC, NMNAT1, RBP7 and UBE4B loci. Cells were cultured in Dulbecco's modified Eagle's medium (DMEM) with 20% fetal bovine serum (FBS). For comparison, the cell lines U87, LN319, SW1088, U343, U373, and A1207 were grown under the same conditions. Normal human astrocytes were obtained from ScienCell.

shRNA Knockdown of ENO2 Expression 22 hairpins targeting ENO2 were screened and 4 independent ones found that reduced protein levels by <50%. Two of these hairpins were in the pLKO.1 vector (shENO2-1 and shENO2-2), and the remaining two were in the Expression Arrest GIPZ (shENO2-3) and TRIPZ (shENO2-4) shRNAmir vectors (Open Biosystems). The ENO2 shRNA sequences were as follows:

```
shENO2-1:
                              (SEQ ID NO: 1)
5'-CAAGGGAGTCATCAAGGACAA-3';

shENO2-2:
                              (SEQ ID NO: 2)
5'-CGCCTGGCTAATAAGGCTTTA-3';

shENO2-3:
                              (SEQ ID NO: 3)
5'-CGGCCTTCAACGTGATCAA-3';

shENO2-4:
                              (SEQ ID NO: 4)
5'-GGGACTGAGAACAAATCCA-3'.
```

The hairpin in the GIPZ vector was cloned into the TRIPZ vector using a protocol provided by the manufacturer. The TRIPZ vector is a doxycycline-inducible system with a red fluorescent protein reporter that is expressed only upon doxycycline induction. Recombinant lentiviral particles were produced by transient transfection of 293T cells following a standard protocol. Briefly, 72 µg of the shRNA plasmid, 54 µg of delta 8.9 plasmid, and 18 µg of VSVG plasmid were transfected using FuGene (Roche) into 293T cells plated in 245 mm² dishes. Viral supernatant was collected 72 h after transfection, concentrated by centrifugation at 23,000 rpm, and resuspended in cell growth medium. For transduction, viral solutions were added to cell culture medium containing 4 µg/mL polybrene; 48 h after infection, cells were selected using 2 µg/mL puromycin and tested for ENO2 knockdown by western blotting.

Ectopic Expression of ENO1, ENO2 and shRNA-Resistant ENO2

Rescue of the phenotypic effects of knocking down ENO2 in the cell line D423-MG was performed by overexpressing an shRNA-resistant form of ENO2. Briefly, 6 silent mutations were introduced into the ENO2 coding region targeted by shENO2-4, using the QuikChange site-directed mutagenesis kit (Stratagene). The shRNA-resistant ENO2 coding region was cloned into the pHAGE-CMV lentiviral vector (a generous gift of D.N. Kotton) and overexpressed in the D423-MG cell line carrying shENO2-4, in the presence or absence of doxycycline. As a control, the same cell line was infected with a lentiviral vector carrying the green fluorescent protein (GFP) gene. For the ectopic re-expression of ENO1 or ENO2, sequenced verified cDNA clones were gateway cloned into the pHAGE-CMV lentiviral vector and lentivirally transduced into glioma cell lines as described above.

Proliferation Assays and Anchorage-Independent Growth

Cell growth of shRNA- or PhAH-treated cell lines was assayed either through crystal violet staining or using the Promega CellTiter-Glo proliferation kit (Roche) or alternatively, in vivo, by measuring confluence with the IncuCyte (Essen BioScience). Growth curves using the IncuCyte were generated by imaging every 2 hours with quadruplicate replicates. For crystal violet assays, $10^4$ cells were seeded in a 6-well plate for each time point. At the indicated time point, cells were fixed with 10% formalin and stained with crystal violet solution for 1 h. Dye extraction was performed using 10% acetic acid solution, and absorbance was read at 590 nm. CellTiter-Glo experiments were performed according to the manufacturer's instructions; $10^3$ cells/well were plated in a 96-well plate for each time point, and luminescence readings were taken every 24 h. All experiments were performed in triplicate. Soft agar (anchorage-independent) growth was monitored in 6-well plates seeded with $10^4$ cells of the indicated genotype. The medium contained DMEM with 10% FBS; the top agar contained 0.4% low melting agarose, while the bottom agar contained 1% low melting agarose. Growth was monitored by fluorescence (GFP) and after 28 days colonies were stained with iodonitrotetrazolium chloride (Sigma-Aldrich) and counted.

Orthotopic Brain Tumor Formation

The in vivo tumorigenic potential of D423-MG cells transduced with non-targeting hairpin or shENO2-3 delivered through pGIPZ was determined as previously described (Zheng et al., 2008). SCID mice (Charles River) under deep anesthesia were placed into a stereotactic apparatus equipped with a z axis (Stoelting). Then, $3 \times 10^5$ cells were injected intracranially into the right caudate nucleus 3 mm below the surface of the brain, using a 10-μl Hamilton syringe. The animals were followed daily for development of neurological deficits. All mice experiments were performed with the approval of the Harvard Cancer Center and Dana-Farber Cancer Institute Institutional Animal Care and Use Committee.

Enolase Activity Assay

Enolase activity was measured via NADH oxidation in a pyruvate kinase-lactate dehydrogenase coupled assay as previously described (Joseph et al., 1996). Briefly, cells were lysed in 20 mM Tris HCl, 1 mM EDTA, and 1 mM β-mercaptoethanol (pH 7.4) and homogenized using a Polytron homogenizer three times for a period of 10 s followed by sonication. Enolase activity was recorded by measuring oxidation of NADH either spectrophotometrically by absorbance at 340 nm or fluorescently by excitation at 340 nm and emission at 460 nm.

Western Blotting

After two washes with phosphate-buffered saline (PBS), cells were incubated in RIPA buffer for 15 min with gentle shaking. Lysates were then collected, sonicated, and centrifuged at 14,000 rpm for 10 min at 4° C. SDS-PAGE and western blotting were performed as described previously (Taniuchi et al., 2005). The following antibodies were used: enolase 1, CST#3810; enolase 2, #9536; and GAPDH CST#3683; phosphor-AMPK Thr172 CST#2535 from Cell Signaling Technologies and vinculin from Sigma-Aldrich.

Inhibitor Studies

PhAH lithium salt was custom synthesized by TCRS, following the protocol of Anderson et al. (1984). Structure and purity were verified by NMR. PhAH was dissolved in PBS at 50 mM stock and stored frozen at −80° C. until use. Given the instability of the compound, the medium was replaced every 5 days and fresh inhibitor added with fresh medium. Rapamycin, sorafenib, lapatinib, and PHA665752 were obtained from LC Laboratories and Tocris Bioscience, respectively.

Cell Cycle Analysis

The D423-MG and U373 cell lines were treated for 48 h in the presence or absence of PhAH (25 μM) and fixed in 75% ethanol at −20° C. overnight. The following day, the cells were washed with cold PBS, treated with 100 μg of RNase A (Qiagen), and stained with 50 μg of propidium iodide (Roche). Flow cytometric acquisition was performed using a three-color FACScan flow cytometer and CellQuest software (Becton Dickinson). For each sample, $10^4$ events were gated. Data analysis was performed using ModFit LT (Verity Software House).

Annexin V/7-AAD Assay for Apoptosis

The D423-MG and U373 cell lines were treated for 96 h in the presence or absence of PhAH (25 μM). For Annexin V/7-AAD assay cells were stained with Annexin V-PE and 7-AAD, and evaluated for apoptosis by flow cytometry according to the manufacturer's protocol (Biovision). The apoptotic cells were determined using a Becton-Dickinson FACScan cytometer. Both early apoptotic (annexin V-positive, 7-AAD-negative) and late apoptotic (annexin V-positive and 7-AAD-positive) cells were included in cell death determinations.

Example 5

Threonyl-tRNA Synthetase (TARS) Heterozygous Deletion Sensitizes Cells to TARS Inhibitors The inventor's undertook studies to determine the effect of TARS deficiency on the sensitivity of cells to the TARS inhibitor Borrelidin. First, analyses were performed to define the correlation between the genomic copy number and the expression of TARS (FIG. 19). The TARS gene copy number was determined in several cell lines (FIG. 19a), and these data were plotted against the mRNA expression level of TARS is the same cell lines (FIG. 19b). Among melanoma cell lines, SK-MEL-2 cells were identified as having a heterozygous deletion for TARS, 451 Lu cells were identified as being TARS deficient, and SK-MEL-5 and HEML cells were identified as being wild-type for TARS (FIG. 20a). To confirm that the expression level of TARS protein corresponded with the expect level based upon gene copy number and mRNA expression level, western blotting was performed (FIG. 20c).

The effect of Borrelidin treatment on the growth of SK-MEL-2, 451 Lu, SK-MEL-5, and HMEL cells was determined. At low concentrations, Borrelidin treatment had minimal to no effect on the growth of HMEL and SK-MEL-5 cells, which are wild-type for TARS (FIG. 20b). In contrast, equivalently low concentrations of Borrelidin stalled the growth of SK-MEL-2 cells. The TARS-deficient 451 Lu cell line showed intermediate sensitivity to Borrelidin treatment.

The effect of various concentrations of Borrelidin on the growth of the four melanoma cells lines over time was also studied (FIG. 21). The HMEL cell line was found to be resistant to Borrelidin treatment even at the highest tested concentration, 62.5 nM. The SK-MEL-2 cell line, which is also wild-type for TARS, was partially sensitive to 62.5 nM Borrelidin but largely resistant to concentrations less than 31.25 nM. Growth of the TARS heterozygous SK-MEL-2 cell line was completely inhibited by 31.25 nM Borrelidin and was at least partially sensitive to concentrations as low as 3.9 nM. Growth of the TARS deficient 451 Lu cell line was nearly inhibited by 62.5 nM Borrelidin and was consistently intermediate between the TARS heterozygous SK-MEL-2 cells and the TARS wild-type cells at all concentrations tested.

Seeing that the highest concentration of Borrelidin tested in the growth assays completely inhibited growth of the SK-MEL-2 cell line prompted the inventors to test for the cytotoxic effect of Borrelidin on SK-MEL-2 cells. To this end, the inventors ran the same live growth assay, except starting with a high confluence of SK-MEL-2 cells at time zero. Under these conditions it became apparent that concentrations of Borrelidin at or above 15 nM are cytotoxic to SK-MEL-2 cells, while lower concentrations are growth inhibitory (FIG. 22).

Figure 23A:
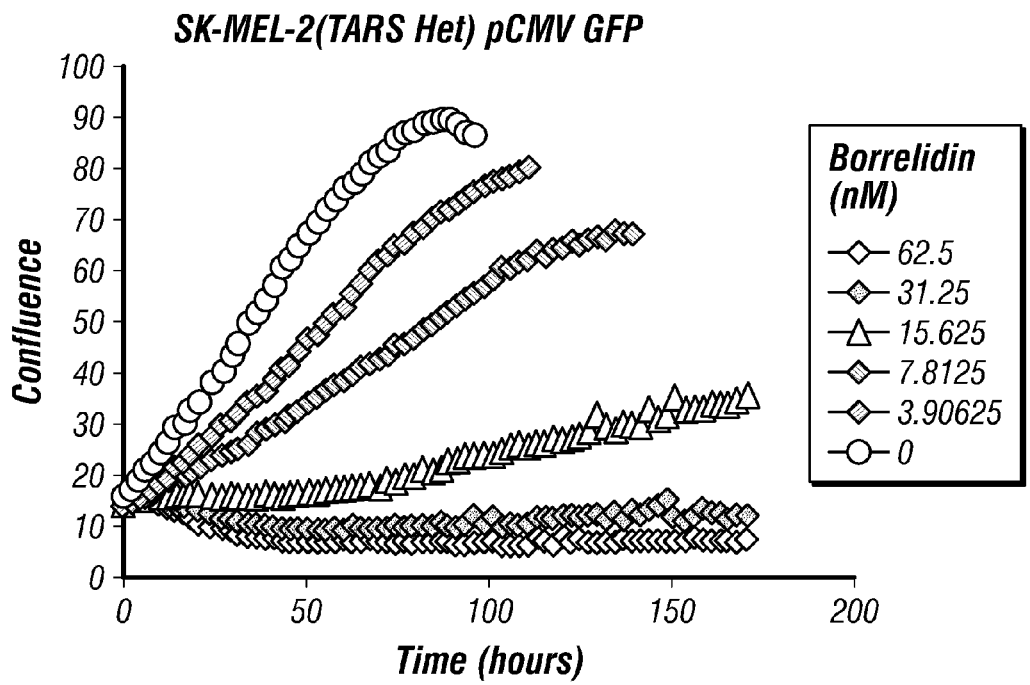
Figure 23B:
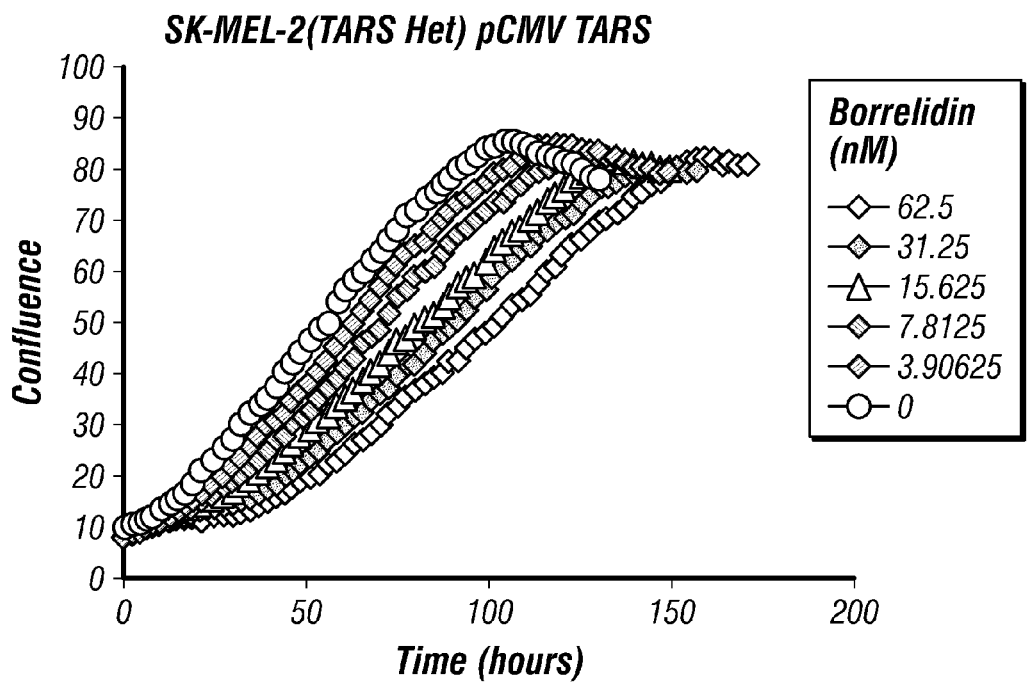
Figure 23C:
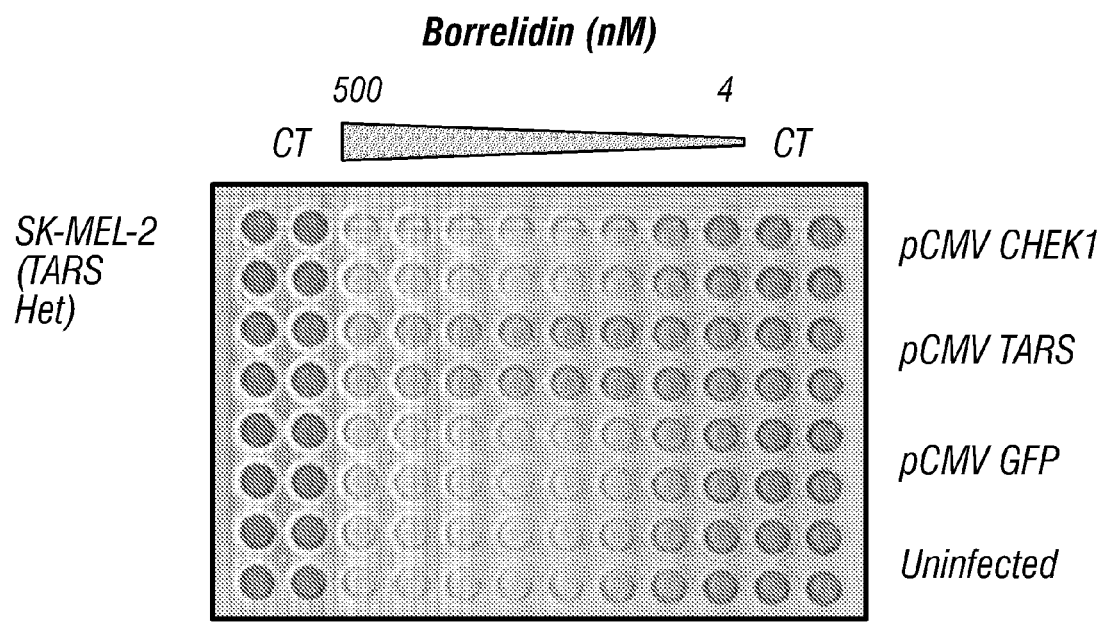
Figure 23D:
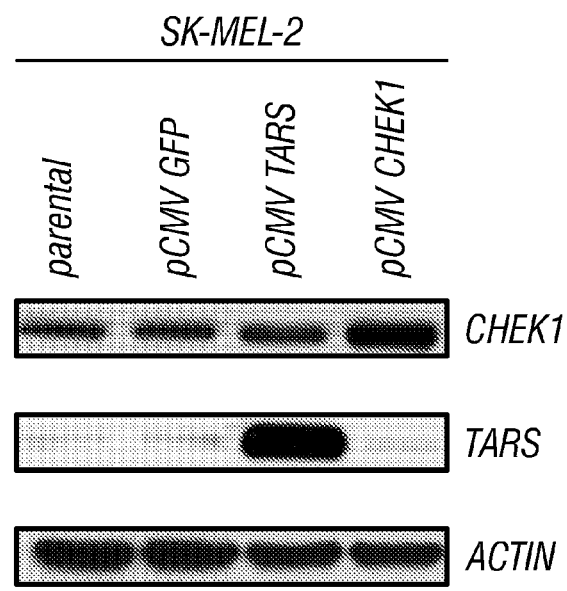

To confirm that the differential effect of Borrelidin on the four melanoma cell lines is in fact due to the relative expression levels of TARS, the inventors ectopically expressed TARS in SK-MEL-2 cells using a lentiviral pCMV vector. Cells were also transduced with GFP- and CHEK1-expressing pCMV vectors as controls, and TARS protein expression levels in the transduced were confirmed by western blotting (FIG. 23d). The effect of Borrelidin on the growth of SK-MEL-2 cells was found to be reversed by expression of exogenous TARS in SK-MEL-2 cells (FIG. 23b,c), while the expression of GFP or CHEK1 had no effect on the response of SK-MEL-2 cells to Borrelidin (FIG. 23a,c). Studies shown in FIG. 24 further establish that TARS gene copy number and mRNA expression level directly correlate with borrelidin sensitivity in cells.

Finally, additional ARS genes were studies to determine whether expression levels correlated with DNA gene copy number. As shown in FIG. 25, significant correlation was noted in the case of AARS, HARS, LARS and KARS expression indicating that ARS genes in general are excellent targets and biomarkers for antic-cancer therapies.

Example 6

Immunohistochemistry can be Used to Accurately Detect Homozygous ENO1 Inactivation Studies were undertaken to confirm whether ENO1 homozygous inactivations (e.g., deletions) could be detected using antibodies binding studies. Briefly, Human cancerous cell lines either ENO1 homozygously deleted (D423-MG) or WT (U87) were injected into the brain of nude mice and allowed to form tumors. Following standard histopathology procedures, tumor-baring brains were fixed and paraffin sections were cut. D423-MG ENO1 null tumor cells stained with Hematoxylin/Eosin could readily be detected by morphology which was verified by staining with an antibody against NUMA (S2825 from Epitomics), which labels only human, not mouse cells. Staining with an antibody against ENO1 (11204-1-AP from Protein Tech), showed strong immunoreactivity in the normal mouse brain, as expected from a widely expressed housekeeping gene. As expected, no staining was seen in D423-MG ENO1 null tumors while strong staining was seen in U87 ENO1 WT tumors. These results show that it is possible to identify ENO1 null tumors by immunohistochemistry directed against ENO1 protein and that this approach could be used to screen for patients that would benefit from e.g., an ENO2 inhibitor.

Example 7

Figure 26A:
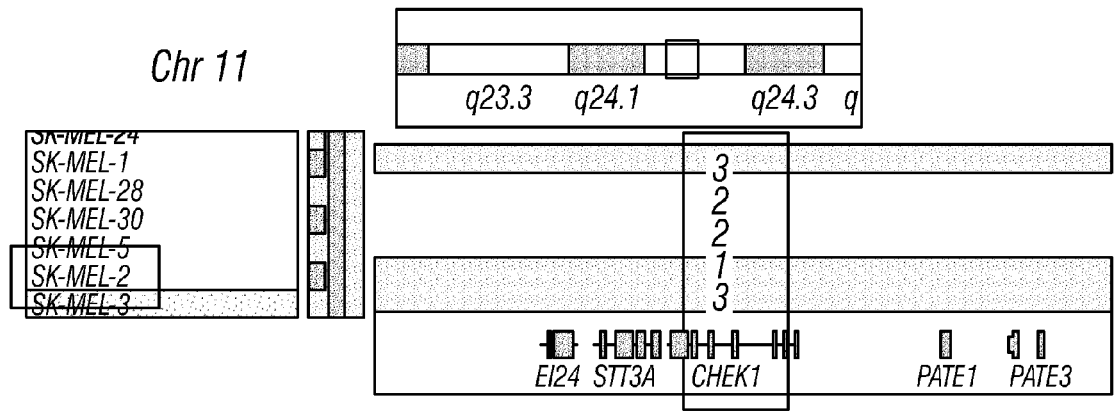
Figure 26B:
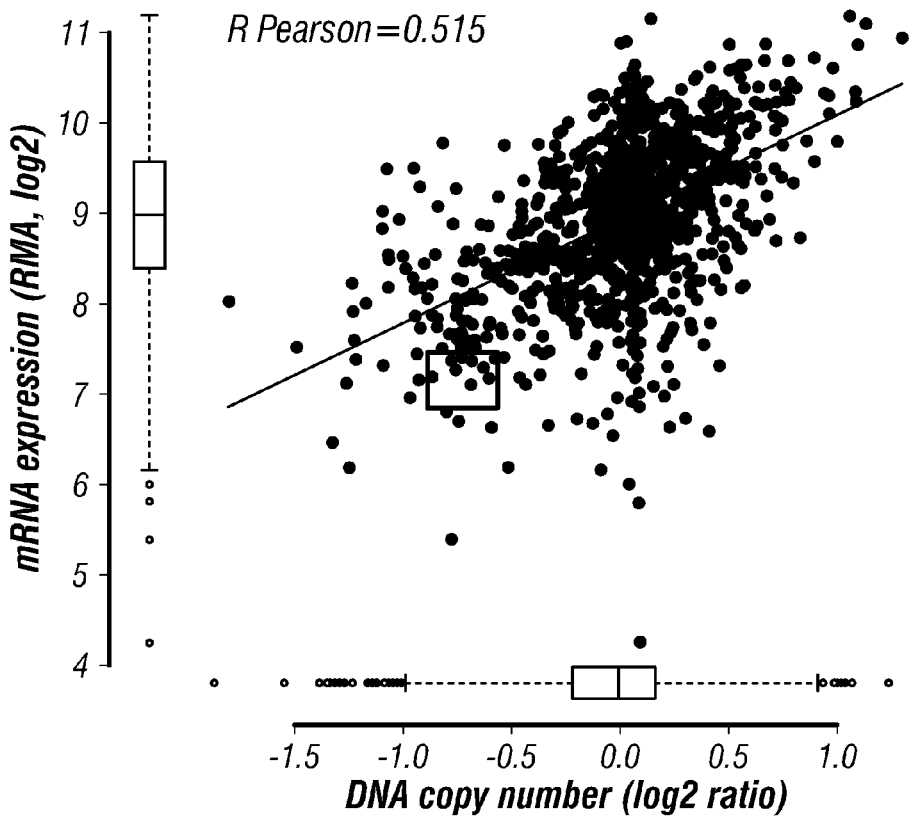
Figure 26C:
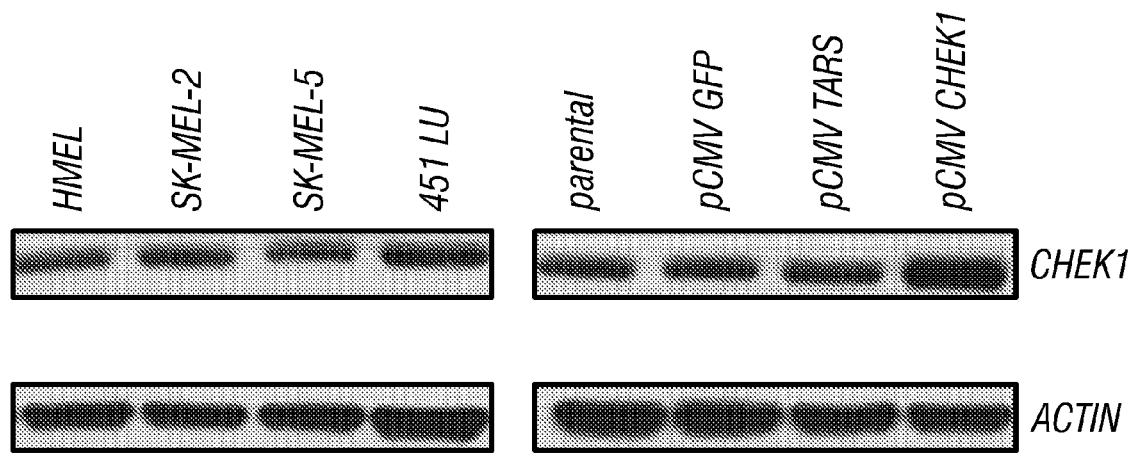
Figure 26D:
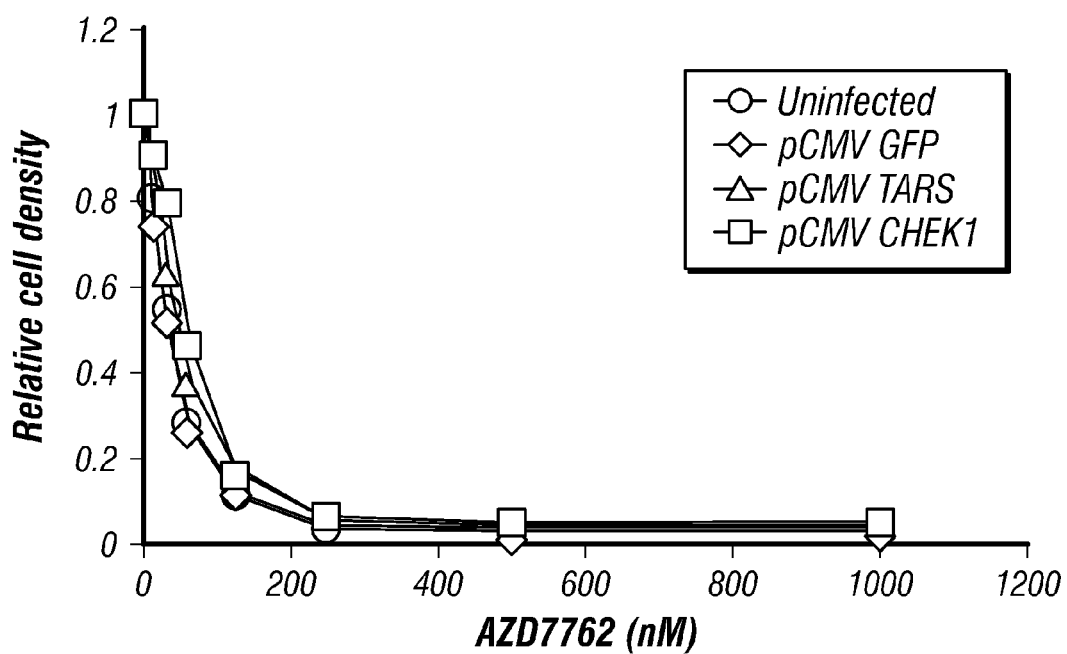

CHEK1 Protein Expression does not Correlate with Genomic Copy Number and Overexpression of CHEK1 does not Confer Resistance to a CHEK1 Inhibitor In contrast to the results for ARS genes and enolase genes shown above, studies indicate that CHEK1 protein expression does not correlate with genomic copy number. Genomic copy number from COMIC (Sanger Center) shows that CHEK1 on chromosome 11 has only one copy in the cell line SK-MEL-2 (FIG. 26A). Indeed, microarray expression and array CGH copy number data show a good correlation between mRNA levels and genomic copy of CHEK1 (FIG. 26B). Nonetheless, SK-MEL-2 cells do not express lower levels of CHEK1 protein by western blot (FIG. 26C). Likewise, overexpression of CHEK1 in SK-MEL-2 cells does not confer resistance to AZD7762, a CHEK1 inhibitor (FIG. 26D). These results may indicate that primary expression control of CHEK1 is a post transcriptional event and that loss of heterozygosity at the CHEK1 locus is insufficient to significantly reduce expression of CHEK1 protein.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,279,721
U.S. Patent Publn. US 2003/0013656
U.S. Patent Publn. US 2003/0013657
U.S. Patent Publn. US 2003/0013846
U.S. Patent Publn. US 2003/0013847
Abaza et al. M phase phosphoprotein 1 is a human plus-end-directed kinesin-related protein required for cytokinesis. *J. Biol. Chem.* 278, 27844-27852, (2003).
Abbondanzo et al., *Breast Cancer Res. Treat.*, 16:182(151), 1990.
Allred et al., *Breast Cancer Res. Treat.*, 16:182(149), 1990.
Anderson et al., *Biochemistry*, 23:2779-2786, 1984.
Anderson, V. E., Weiss, P. M. & Cleland, W. W. Reaction intermediate analogues for enolase. Biochemistry 23, 2779-2786 (1984).
Ausubel et al., *Current Protocols in Molecular Biology*, Greene Publishing Associates and Wiley Interscience, N.Y., 1996.
Ausubel et al., *In: Current Protocols in Molecular Biology*, John, Wiley & Sons, Inc, New York, 1998.
Bagchi, A. & Mills, A. A. The quest for the 1p36 tumor suppressor. *Cancer Res.* 68, 2551-2556, (2008).
Bakhshi et al., *Cell*, 41(3):899-906, 1985.
Bignell et al., *Nature*, 463:893-898, 2010.
Brookfield, Genetic redundancy. Adv Genet 36, 137-155 (1997).
Brown et al. *Immunol. Ser.*, 53:69-82, 1990.

Bulteau et al. Reversible redox-dependent modulation of mitochondrial aconitase and proteolytic activity during in vivo cardiac ischemia/reperfusion *Proc Natl Acad Sci USA*. 2005 Apr. 26; 102(17): 5987-5991.

Buszczak et al. The carnegie protein trap library: a versatile tool for *Drosophila* developmental studies. *Genetics* 175, 1505-1531, (2007).

Cancer Genome Atlas Research Network, In: *Comprehensive genomic characterization defines human glioblastoma genes and core pathways. Nature,* 455:1061-1068, 2008.

Chen et al. Serum and urine metabolite profiling reveals potential biomarkers of human hepatocellular carcinoma. *Molecular and cellular proteomics* 10: M110.004945

Cho et al., Dephosphorylation of 2,3-bisphosphoglycerate by MIPP expands the regulatory capacity of the Rapoport-Luebering glycolytic shunt. *Proc Natl Acad Sci USA* 105, 5998-6003, (2008).

Clarke et al., *Arch. Biochem. Biophys.* 415: 229-234, 2003.

Cleary and Sklar, *Proc. Natl. Acad. Sci. USA,* 82(21):7439-7443, 1985.

Cleary et al., *J. Exp. Med.,* 164(1):315-320, 1986.

Comi et al., *Ann. Neurol.,* 50:202-207, 2001.

Costanzo et al., The genetic landscape of a cell. *Science,* 327:425-431, 2008.

Cox et al. A survey of homozygous deletions in human cancer genomes. *Proc Natl Acad Sci USA* 102, 4542-4547, (2005).

de, A. S, N. M. V. et al. Structural flexibility in *Trypanosoma brucei* enolase revealed by X-ray crystallography and molecular dynamics. *FEBS J.* 274, 5077-5089, (2007).

De Jager et al., *Semin. Nucl. Med.,* 23(2):165-179, 1993.

DeLuna et al. Exposing the fitness contribution of duplicated genes. *Nat. Genet.* 40, 676-681, (2008).

De Soto et al., PARP-1 inhibitors: are they the long-sought genetically specific drugs for BRCA1/2-associated breast cancers? *Int J Med Sci* 3, 117-123 (2006).

Deutscher et al., *Nat. Genet.,* 38:993-998, 2006.

*Design of Prodrugs* (ed. H. Bundgaard), Elsevier Science Publishers BV, Amsterdam, 1985.

Doolittle and Ben-Zeev, *Methods Mol, Biol,* 109:215-237, 1999.

Druker, Translation of the Philadelphia chromosome into therapy for CML. *Blood* 112, 4808-4817, (2008).

Duncan, C. G. et al. Integrated genomic analyses identify ERRFI1 and TACC3 as glioblastoma-targeted genes. *Oncotarget* 1, 265-277 (2010).

Guha PARP inhibitors stumble in breast cancer. *Nat. Biotechnol.* 29, 373-374, (2011).

Guha-Chowdhury et al., Inhibition of purified enolases from oral bacteria by fluoride. *Oral Microbiol. Immunol.* 12, 91-97 (1997).

Gulbis and Galand, *Hum. Pathol.* 24(12), 1271-1285, 1993.

Henrich et al. CAMTA1, a 1p36 tumor suppressor candidate, inhibits growth and activates differentiation programs in neuroblastoma cells. *Cancer Res.* 71, 3142-3151, (2011).

Hill et al., The Rab6-binding kinesin, Rab6-KIFL, is required for cytokinesis. *EMBO J.* 19, 5711-5719 (2000).

Huttunen et al., *Pharmacol. Rev.,* 63(3):750-71, 2011.

Hsieh et al., *Curr. Pharm. Des.,* 15(19):2236-50, 2009.

Joseph et al., Enolase activity and isoenzyme distribution in human brain regions and tumors. *J. Neurochem.* 66, 2484-2490 (1996).

Keller et al., Halofuginone and other febrifugine derivatives inhibit prolyl-tRNA synthetase. *Nat. Chem. Biol.* 8(3): 311-7, 2012.

Kerr et al., *Br. J. Cancer,* 26(4):239-257, 1972.

Kobayakawa et al., *Nature,* 450:503-508, 2007.

Kotliarov, Y. et al. High-resolution global genomic survey of 178 gliomas reveals novel regions of copy number alteration and allelic imbalances. *Cancer Res* 66, 9428-9436, (2006).

Law Perfusion and MRS for brain tumor diagnosis. *Clinical MR.* Chapter 43: 1215-1243.

Leonardi et al., Pantothenate kinase 1 is required to support the metabolic transition from the fed to the fasted state. *PLoS One* 5, e11107, (2010a).

Leonardi et al. Modulation of pantothenate kinase 3 activity by small molecules that interact with the substrate/allosteric regulatory domain. *Chem. Biol.* 17, 892-902, (2010b).

Leonardi et al. Activation of human mitochondrial pantothenate kinase 2 by palmitoylcarnitine *PNAS* 2007: 1494-1499.

Maser et al. Chromosomally unstable mouse tumours have genomic alterations similar to diverse human cancers. *Nature* 447, 966-971, (2007).

Moller-Hartmann et al. Clinical application of proton magnetic resonance spectroscopy in the diagnosis of intracranial mass lesions. *Neuroradiology* 44: 371-381

Moore et al., Double or nothing: a *Drosophila* mutation affecting meiotic chromosome segregation in both females and males. *Genetics* 136, 953-964 (1994).

Mueller et al., *Oncogene,* 26:583-593, 2007.

Nakamura et al., In: *Handbook of Experimental Immunology* ($4^{th}$ Ed.), Weir et al. (Eds.), 1:27, Blackwell Scientific Publ., Oxford, 1987.

Navarro et al., *FEBS J.,* 274:5077-5089, 2007.

Nelson Multivoxel Magnetic Resonance Spectrosopy of brain tumors. *Molecular Cancer Therapeutics* 2, 497-507

Nijhawan et al., *Cell,* 150:842-854, 2012.

Odunsi Detection of epithelial ovarian cancer using 1H-NMR-based metabolomics. *Int. J. of Cancer* 2005: 782-788.

Parrish et al. Novel ATP-competitive kinesin spindle protein inhibitors. *J. Med. Chem.* 50, 4939-4952, (2007).

Peng et al. Array-based comparative genomic hybridization analysis of high-grade neuroendocrine tumors of the lung. *Cancer Sci.* 96, 661-667, (2005).

Possemato et al. Functional genomics reveal that the serine synthesis pathway is essential in breast cancer. *Nature* 476, 346-350, (2011).

Poyner et al., Structure of the bis divalent cation complex with phosphonoacetohydroxamate at the active site of enolase. *Biochemistry* 31, 7166-7173 (1992).

Raj et al. Selective killing of cancer cells by a small molecule targeting the stress response to ROS. *Nature* 475, 231-234, (2011).

Sambrook et al., Molecular Cloning: A Laboratory Manual, 3rd Edition, Cold Spring Harbor Laboratory, N.Y., 1989.

Smith et al., Complete loss of iron regulatory proteins 1 and 2 prevents viability of murine zygotes beyond the blastocyst stage of embryonic development. *Blood Cells Mol. Dis.* 36, 283-287, (2006).

Sonnichsen et al. Full-genome RNAi profiling of early embryogenesis in *Caenorhabditis elegans. Nature* 434, 462-469, (2005).

Spratlin et al. Clinical applications of metabolonics in oncology: a review. *Clinical cancer research* 15: 431-440.

Stefanini, *Am. J. Clin. Pathol.,* 58:408-414, 1972.

Stommel et al. Coactivation of receptor tyrosine kinases affects the response of tumor cells to targeted therapies. *Science* 318, 287-290, (2007).

Sundrud et al., Halofuginone inhibits TH17 cell differentiation by activating the amino acid starvation response. *Science,* 324(5932):1334-8, 2009.

Taniuchi et al. Down-regulation of RAB6KIFL/KIF20A, a kinesin involved with membrane trafficking of discs large homologue 5, can attenuate growth of pancreatic cancer cell. *Cancer Res.* 65, 105-112, (2005).

Taylor et al. Integrative genomic profiling of human prostate cancer. *Cancer Cell* 18, 11-22, (2010).

Tcherniuk et al. Relocation of Aurora B and survivin from centromeres to the central spindle impaired by a kinesin-specific MKLP-2 inhibitor. Angew Chem Int Ed Engl 49, 8228-8231, (2010).

Tonon et al. High-resolution genomic profiles of human lung cancer. Proc Natl Acad Sci USA 102, 9625-9630, (2005).

Tsujimoto and Croce, *Proc. Natl. Acad. Sci. USA,* 83(14): 5214-5218, 1986.

Tsujimoto et al., *Nature,* 315:340-343, 1985.

Vavouri et al., Widespread conservation of genetic redundancy during a billion years of eukaryotic evolution. *Trends Genet.* 24, 485-488, (2008).

Wise et al., Glutamine addiction: a new therapeutic target in cancer. *Trends Biochem. Sci.* 35, 427-433, (2010).

Yin et al. High-resolution genomic copy number profiling of glioblastoma multiforme by single nucleotide polymorphism DNA microarray. *Mol. Cancer Res.* 7, 665-677, (2009).

Zhang et al. Chemical knockout of pantothenate kinase reveals the metabolic and genetic program responsible for hepatic coenzyme A homeostasis. *Chem. Biol.* 14, 291-302, (2007).

Zheng et al., *Nature,* 4551129-1133, 2008.

Zhou et al. A novel pantothenate kinase gene (PANK2) is defective in Hallervorden-Spatz syndrome. *Nat. Genet.* 28, 345-349, (2001).

---

What is claimed is:

1. A method of treating cancer in a subject, comprising administering to the subject an effective amount of an inhibitor of a functionally redundant homologue of a housekeeping gene, said cancer in the subject having been determined to have a homozygous deletion in the housekeeping gene.

2. The method of claim 1, wherein the inhibitor is a nucleic acid that inhibits the expression or activity of the redundant homologue, an antibody that specifically binds the redundant homologue or a small molecule inhibitor of the redundant homologue.

3. The method of claim 1, further comprising administering a chemotherapeutic agent to the subject.

4. The method of claim 3, wherein the chemotherapeutic agent interferes with DNA homeostasis.

5. The method of claim 1, wherein:
a) the housekeeping gene is enolase 1 (ENO1) and the redundant homologue is enolase 2 (ENO2);
b) the housekeeping gene is hexose-6-phosphate dehydrogenase (H6PD) and the redundant homologue is glucose-6 dehydrogenase (G6PD);
c) the housekeeping gene is kinesin family member 1B (KIF1B) and the redundant homologue is kinesin family member 1A (KIF1A) or kinesin family member 1C (KIF1C);
d) the housekeeping gene is Nicotinamide nucleotide adenylyl transferase 1 (NMNAT1) and the redundant homologue is Nicotinamide nucleotide adenylyl transferase 2 (NMNAT2) or nicotinamide nucleotide adenylyl transferase 3 (NMNAT3);
e) the housekeeping gene is ubiquitination factor E4B (UBE4B) and the redundant homologue is ubiquitination factor 4A (UBE4A);
f) the housekeeping gene is aconitase 1 (ACO1) and the redundant homologue is aconitase 2 (ACO2) or aconitase 3 (ACO3);
g) the housekeeping gene is kelch-like 9 (KLHL9) and the redundant homologue is kelch-like 13 (KLHL13);
h) the housekeeping gene is pantothenate kinase 1 (PANK1) and the redundant homologue is pantothenate kinase 3 (PANK3); or
i) the housekeeping gene is kinase family member 20B (KIF20B) and the redundant homologue is kinase family member 20A (KIF20A).

6. The method of claim 5, wherein the housekeeping gene is ENO1 and the redundant homologue is ENO2 and wherein the inhibitor is a glycolysis inhibitor.

7. The method of claim 6, wherein the glycolysis inhibitor is an enolase inhibitor.

8. The method of claim 7, the enolase inhibitor is a small molecule enolase inhibitor.

9. The method of claim 8, wherein the enolase inhibitor comprises D-tartronate semialdehyde phosphate; 3-aminoenolpyruvate-2-phosphate; phosphonoacetohydroaxamate (PhAH); 2-fluoro-2-phosphonoacetohydroxamate; (3-hydroxy-2-nitropropyl)phosphonate; (nitroethyl)phosphonate; d -(phosphonoethyl)nitrolate or a prodrug thereof.

10. The method of claim 7, wherein the glycolysis inhibitor is 2-deoxyglucose, 6-aminonicotinamide, tetrose diphosphate, koningic acid or MJE3 or a prodrug thereof.

11. The method of claim 5, wherein the housekeeping gene is H6PD and the redundant homologue is G6PD and wherein the inhibitor is dehydroepiandrosterone or a prodrug thereof.

12. The method of claim 5, wherein the housekeeping gene is NMNAT1 and the redundant homologue is NMNAT2 or NMNAT3 and wherein the inhibitor is Np2AD, Np4AD or Nap4AD or a prodrug thereof.

13. The method of claim 5, wherein the housekeeping gene is ACO1 and the redundant homologue is ACO2 or ACO3 and wherein the inhibitor is fluorocitrate or a prodrug thereof.

14. The method of claim 5, wherein the housekeeping gene is PANK1 and the redundant homologue is PANK3 and wherein the inhibitor is hopantenate or a prodrug thereof.

15. The method of claim 1, further comprising measuring the level of one or more metabolites of the metabolic pathway of the housekeeping gene in a sample from the subject, wherein an accumulation of the metabolite indicates that the treatment is efficacious.

16. The method of claim 15, wherein the housekeeping gene is enolase and the metabolite is glyerate.

17. The method of claim 1, wherein the cancer was determined to have a homozygous deletion in the housekeeping gene by DNA sequencing.

18. A method of treating a subject having a cancer comprising, administering an effective amount of a glycolysis inhibitor to the subject, said cancer in the subject having been previously determined to comprise a heterozygous mutation that inactivates one copy of the Enolase 1 (ENO1) gene.

19. The method of claim 18, wherein the glycolysis inhibitor comprises D-tartronate semialdehyde phosphate; 3-aminoenolpyruvate-2-phosphate; phosphonoacetohydroaxamate (PhAH); 2-fluoro-2-phosphonoacetohydroxamate; (3-hydroxy-2-nitropropyl)phosphonate; (nitroethyl) phosphonate; d-(phosphonoethyl)nitrolate or a prodrug thereof.

20. A method of treating a subject having a cancer comprising, administering an effective amount of an ARS inhibitor, or a prodrug thereof, to the subject, said cancer in the subject having been determined to comprise a heterozygous mutation that inactivates one copy of a tRNA synthetase (ARS) gene.

* * * * *